United States Patent
Smith

(10) Patent No.: US 11,939,344 B2
(45) Date of Patent: Mar. 26, 2024

(54) SPIROCYCLIC COMPOUNDS

(71) Applicant: ASTRAZENECA AB, Sodertalje (SE)

(72) Inventor: James Michael Smith, Cambridge (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 18/335,225

(22) Filed: Jun. 15, 2023

(65) Prior Publication Data
US 2023/0357279 A1    Nov. 9, 2023

Related U.S. Application Data

(63) Continuation of application No. 18/306,596, filed on Apr. 25, 2023, now abandoned, which is a continuation of application No. PCT/EP2022/075248, filed on Sep. 12, 2022.

(60) Provisional application No. 63/243,267, filed on Sep. 13, 2021.

(51) Int. Cl.
C07D 519/00    (2006.01)

(52) U.S. Cl.
CPC .................. *C07D 519/00* (2013.01)

(58) Field of Classification Search
CPC .................................................... C07D 519/00
USPC ........................................................... 546/15
See application file for complete search history.

(56) References Cited

U.S. PATENT DOCUMENTS

| | | | |
|---|---|---|---|
| 5,324,483 A | 6/1994 | Cody et al. | |
| 8,455,477 B2 * | 6/2013 | Katz | A61P 43/00 514/233.2 |
| 2019/0127387 A1 | 5/2019 | Wang et al. | |

FOREIGN PATENT DOCUMENTS

WO    2020076660 A    4/2020

OTHER PUBLICATIONS

Pesquet et al., "Access to 3-spiroindolizines containing an isoindole ring through intra-molecular arylation of spiro-N-acyliminium species: a new family of potent farnesyltransferase inhibitors", Organic & Biomolecular Chemistry, 2019, pp. 2798-2808, vol. 17, No. 10.
Chortani et al., "Aza-heterocyclic frameworks through intramolecular π-system trapping of spiro-N-acyliminiums generated from isoindolinone", New Journal of Chemistry, 2021, pp. 2393-2403, vol. 45, No. 5.
Wrobel J., et al., Novel Spirosuccinimides with Incorporated Isoindolone and Benzisothiazole 1,1-Dioxide Moieties as Aldose Reductase Inhibitors and Antihyperglycemic Agents, Journal of Medicinal Chemistry, 1992, vol. 35, No. 24, pp. 4613-4627. DOI: 10.1021/jm00102a016.
International Search Report and Written Opinion for international Application No. PCT/EP2022/075248, dated Jan. 24, 2023.

* cited by examiner

*Primary Examiner* — Kahsay Habte

(57) ABSTRACT

The specification relates to spirocyclic compounds of Formula (I) and pharmaceutically acceptable salts thereof. The specification also relates to processes and intermediates used for their preparation, pharmaceutical compositions containing them and their use in the treatment of cell proliferative disorders.

4 Claims, 1 Drawing Sheet

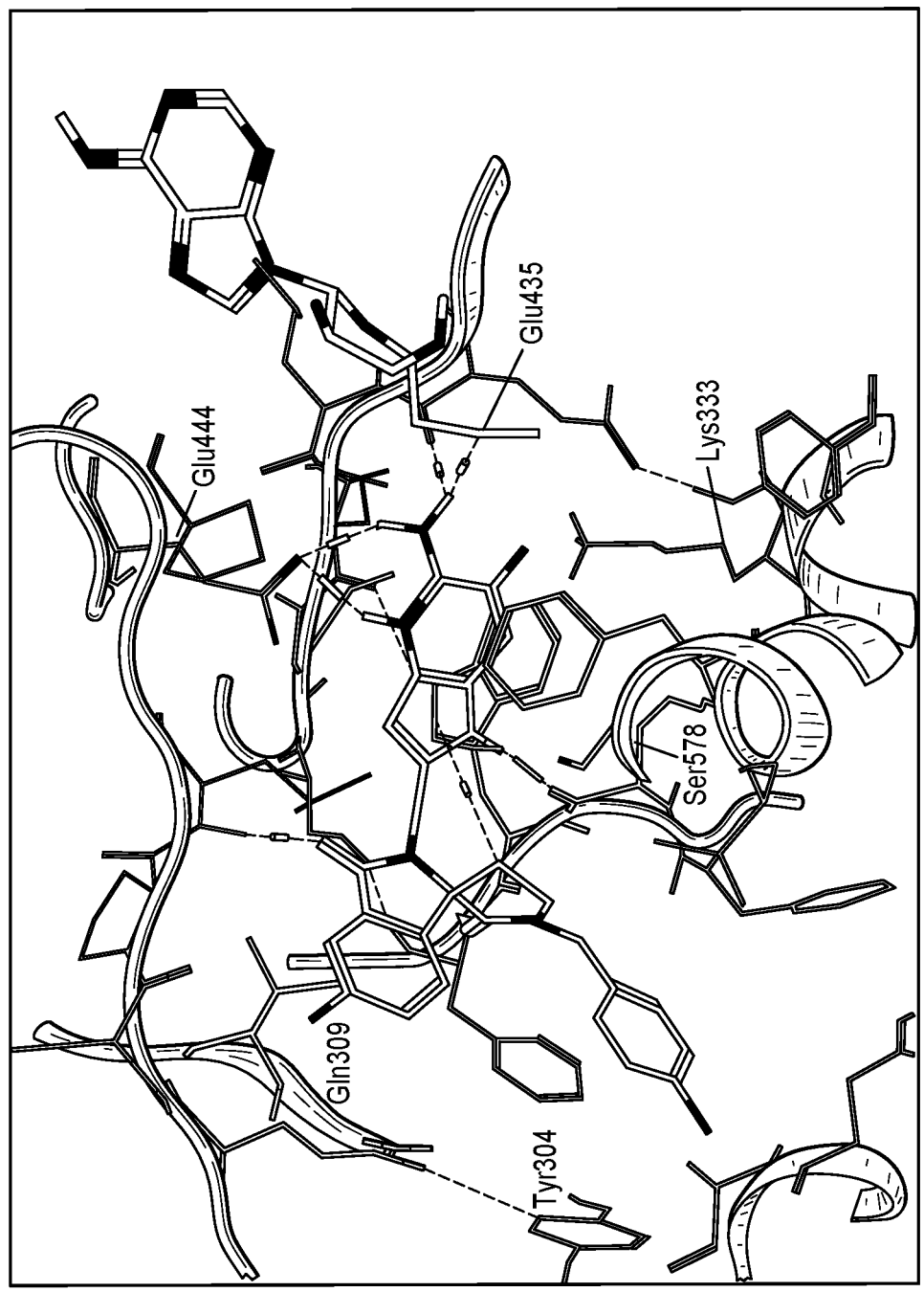

SPIROCYCLIC COMPOUNDS

This application is a continuation of U.S. patent application Ser. No. 18/306,596, filed on Apr. 25, 2023, which is a continuation of International Patent Application No. PCT/EP2022/075248 filed on Sep. 12, 2022, said Application No. PCT/EP2022/075248 claims benefit under 35 U.S.C. § 119 (e) of U.S. Provisional Application No. 63/243,267 filed Sep. 13, 2021. Each of the above listed applications is incorporated by reference herein in its entirety for all purposes.

This specification relates to certain spirocyclic compounds, and pharmaceutically acceptable salts thereof, that inhibit the protein arginine methyltransferase 5 (PRMT5) enzyme, and consequently exhibit anti-cancer activity. The specification also relates to the use of said spirocyclic compounds and pharmaceutically acceptable salts thereof in methods of treatment of the human or animal body, for example for the prevention or treatment of cancer. The specification also relates to processes and intermediate compounds involved in the preparation of said spirocyclic compounds and to pharmaceutical compositions containing them.

Protein arginine methyltransferase 5 (PRMT5) is a member of the PRMT family of arginine methyltransferase enzymes that catalyse the addition of methyl groups to the guanidine motif of arginine residues, using S-adenosyl-L-methionine (SAM) as methyl donor. PRMT5 is a type II arginine methyltransferase that symmetrically dimethylates the guanidine group of arginine residues thus converting a guanidine $NH_2$ group of arginine to a $NMe_2$ group. PRMT5 methylates a number of diverse substrates including histone and non-histone proteins, and in so doing regulates processes such as RNA splicing, cellular proliferation and DNA repair. Significantly, PRMT5 is overexpressed in a number of cancer types and has been identified as a candidate for therapeutic intervention through the development of small molecules that inhibit PRMT5 methyltransferase activity (see e.g. Kim et al., (2020) Cell Stress 4(8) 199-2151).

Cyclin dependent kinase inhibitor 2A (CDKN2A) is a tumour suppressor gene that is homozygously deleted in approximately 15% of cancers. Loss of the 9p21 chromosome locus results in the co-deletion of a number of additional genes including the gene encoding methylthioadenosine phosphorylase (MTAP). MTAP is a metabolic enzyme involved in methionine salvage and loss of MTAP results in increased concentrations of the MTAP substrate methylthioadenosine (MTA) in CDKN2A/MTAP deleted cancer cells. MTA itself acts as a weak PRMT5 inhibitor and MTA accumulation in CDKN2A/MTAP deleted cancer cell lines accordingly leads to a partial inhibition of PRMT5 activity. Compromised PRMT5 activity renders CDKN2A/MTAP deleted cancer cells susceptible to further targeting of PRMT5, for example using short hairpin RNA (shRNA). A "collateral vulnerability" in cancer, where CDKN2A/MTAP deleted tumours may be selectively targeted through PRMT5 inhibition, has been identified (see Marjon et al., (2016) Cell Reports 15, 574-587; Mavrakis et al., (2016) Science 11;351(6278):1208-13; Kryukov et al., (2016) Science 11;351(6278):1214-8).

There is a need for the development of "MTA-synergistic" PRMT5 inhibitors (i.e. inhibitors which bind to PRMT5 preferentially in the presence of MTA) for the treatment of cancer. This is because "MTA-synergistic" PRMT5 inhibitors exert a greater inhibitory effect on PRMT5 in environments where relatively high concentrations of MTA are present such as CDKN2A/MTAP deleted tumour cells and not in healthy tissues. Consequently, "MTA-synergistic" PRMT5 inhibitors should possess a high therapeutic index (and low off target toxicity) as their anti-proliferative activity will selectively manifest in the targeted, CDKN2A/MTAP deleted, tumour cells. To date no inhibitors of PRMT5, let alone "MTA-synergistic" PRMT5 inhibitors, have been approved for therapeutic use. Hence there is a need for new PRMT5 inhibitors, ideally PRMT5 inhibitors that are "MTA-synergistic" and that possess the required pharmaceutical properties to be suitable for clinical use, as they will provide new options for cancer treatment. The compounds of the specification have been found to possess anti-tumour activity, being useful in inhibiting the uncontrolled cellular proliferation which arises from malignant disease. The compounds of the specification provide an anti-tumour effect by, as a minimum, acting as inhibitors of PRMT5. Significantly, the PRMT5 inhibitors according to the specification are "MTA-synergistic" PRMT5 inhibitors and are expected to show enhanced clinical utility due to their unique activity profile that should deliver a high therapeutic index and low off target toxicity.

According to a first aspect of the specification there is provided a compound of Formula (I), or a pharmaceutically acceptable salt thereof:

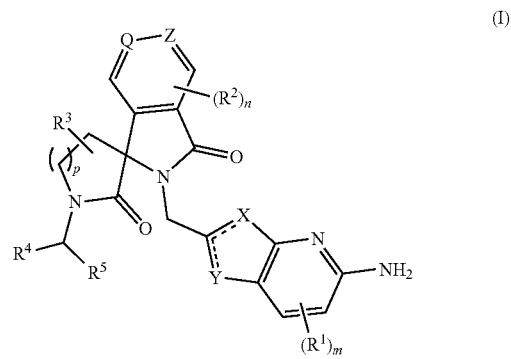

wherein:
the ring containing X and Y is a pyrrole and X is NH and Y is CH or X is CH and Y is NH;
Z is selected from CH, CF, CCl or, if Q is not N, N;
Q is selected from CH, CF, CCl or, if Z is not N, N;
m is 0, 1 or 2;
n is 0, 1 or 2;
p is 1 or 2;
$R^1$ is in each occurrence independently selected from F, Cl, CN, Me, $CF_3$, $C_1$-$C_3$ alkyl, cyclopropyl, $C_1$-$C_3$ fluoroalkyl, OMe or $C_1$-$C_3$ alkoxy;
$R^2$ is in each occurrence independently selected from F, Cl, Me, MeO and $CF_3$;
$R^3$ is H, Me, $C_1$-$C_3$ alkyl or $C_1$-$C_3$ fluoroalkyl;
$R^4$ is H, Me or $C_1$-$C_3$ alkyl;
$R^5$ is H, Me, $C_1$-$C_3$ alkyl, $C_1$-$C_3$ fluoroalkyl, $CH_2OMe$, $CH_2OCHF_2$, $CH_2OCF_3$, $CH_2O(C_1$-$C_3$ alkyl), $CH_2O(C_1$-$C_3$ fluoroalkyl), $C(CH_2CH_2)R^6$, $CCR^7$, $CH_2R^8$, $R^9$ or $CH_2R^{10}$;
$R^6$ is H, Me, $CH_2F$, $CHF_2$, $CF_3$, $CH_2OH$ or $CH_2OMe$;
$R^7$ is H, Me, cyclopropyl, $C_1$-$C_3$ alkyl, $C_1$-$C_3$ fluoroalkyl, $C_3$-$C_6$ cycloalkyl or a 5-membered heteroaryl group optionally substituted with Me, $C_1$-$C_3$ alkyl, F or Cl;
$R^8$ is a 5-membered heteroaryl optionally substituted with Me, $C_1$-$C_3$ alkyl, F or Cl;

R⁹ is an optionally substituted phenyl, 5- or 6-membered heteroaryl, or bicyclic heteroaryl group; and R¹⁰ is an optionally substituted phenyl, 5- or 6-membered heteroaryl, or bicyclic heteroaryl group.

In a further aspect there is provided a compound of Formula (I), or a pharmaceutical acceptable salt thereof, for use as a medicine.

In a further aspect there is provided a pharmaceutical composition comprising a compound of Formula (I), or a pharmaceutical acceptable salt thereof.

In a further aspect there is provided a method of treating cancer by administering to a patient in need thereof an effective amount of a compound of Formula (I), or a pharmaceutical acceptable salt thereof.

In a further aspect there is provided a compound of Formula (I), or a pharmaceutical acceptable salt thereof, for use in the treatment of cancer.

In a further aspect there is provided a compound of Formula (I), or a pharmaceutical acceptable salt thereof, for use in the manufacture of a medicament, for example a medicament for use in the treatment of cancer.

In a further aspect there is provided a kit comprising a pharmaceutical composition comprising a compound of Formula (I), or a pharmaceutical acceptable salt thereof, and instructions for its use in the treatment of cancer.

In a further aspect there is provided a method for the manufacture of a compound of Formula (I).

The compounds of Formula (I), feature a spirocyclic core in which a 2-pyrrolidinone ring (referred to in this paragraph and illustrated below as ring A) and a second ring (referred to in this paragraph and illustrated below as ring B), selected from 2-pyrrolidinone and 2-piperidinone, share a carbon atom through which they are connected and at which point a chiral centre is located. In addition, the nitrogen atom of ring A is connected to a 4- or -7-azaindole motif via a methylene (i.e. CH₂) linker. Ring A is also fused to a phenyl or a pyridine ring. The nitrogen atom of ring B is substituted with a group CHR⁴R⁵.

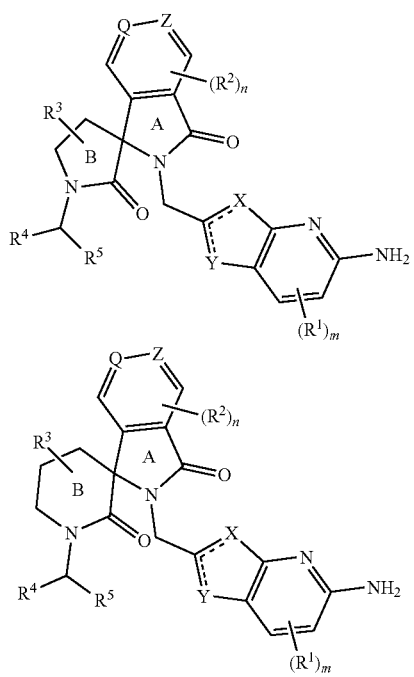

It has been found that the compounds of Formula (I) possess potent anti-tumour activity that derives from their ability to inhibit PRMT5. As already noted above, PRMT5 is an enzyme that uses SAM as a methyl donor for the symmetrical demethylation of the guanidine group of arginine thus playing an important role in the epigenetic modification of histone and non-histone substrates in cells. PRMT5 is implicated in tumour growth via promotion of histone tail modifications that repress miRNAs that target tumour promoting genes. Studies indicate that the MTAP gene is deleted in ca 15% of cancers and that such cancers are more dependent on PRMT5 enzyme activity than wild type cells without the MTAP gene deletion. This MTAP deletion is found in a significant proportion of cancers and creates a genetic vulnerability that can be exploited for their treatment. In addition, MTAP deletion causes cancer cells to accumulate MTA as its phosphorylation is blocked, with MTAP deleted cells consequently exhibiting high MTA concentrations relative to wild-type, MTAP expressing, cells.

In contrast to known PRMT5 inhibitors, compounds according to the specification advantageously bind, and inhibit, PRMT5 more effectively in the presence of MTA—they are "MTA-synergistic". This synergy with MTA is a particularly beneficial as the PRMT5 inhibition observed with compounds according to the specification is elevated in the MTAP deficient cancer cells, where MTA levels are characteristically high relative to normal wild type cells, relative to normal cells and thus undesirable off target toxicity is reduced. This profile should allow high levels of PRMT5 inhibition to be achieved in the target cells without unacceptable off target toxicity. Off target toxicity is a particular concern for PRMT5 inhibitors and has been dose limiting in the clinic with non MTA selective PRMT5 inhibitors such as GSK3326595. PRMT5 inhibitors according to the present specification consequently possess a larger therapeutic window than earlier, non-MTA selective, PRMT5 inhibitors that could well allow optimal levels of PRMT5 inhibition to be achieved and deliver enhanced therapeutic benefit.

Compounds according to the present specification possess good physicochemical properties that indicate that they will be suited to oral administration to humans to deliver a therapeutic effect. For example, in addition to their ability to inhibit PRMT5, compounds according to the specification possess good solubility profiles and relatively low molecular weight that indicate their suitability for oral administration. As described further herein, the stereochemical configurations of the compounds of the specification and, in particular, their chirality at the spirocyclic centre, are key determinants in their PRMT5 inhibitory activity.

Accordingly, the compounds of the present specification may be of value as anti-tumour agents. In particular, the compounds of the present specification may find application as selective inhibitors of the proliferation, survival, motility, dissemination and invasiveness of mammalian cancer cells that are MTAP deficient. Due to their ability to inhibit PRMT5, treatment of a subject with a compound according to the present specification may lead to inhibition of tumour growth, trigger tumour regression, and/or inhibit formation of metastases and/or metastatic tumour growth. Particularly, the compounds of the present specification may be of value as anti-proliferative and anti-invasive agents in the containment and/or treatment of solid tumour disease. Particularly, the compounds of the present specification may be useful in the prevention or treatment of those tumours which are sensitive to inhibition of PRMT5 and wherein PRMT5 activity is implicated in cell-signalling events that lead to the proliferation and survival of tumour cells.

Accordingly, there is also provided a method for providing a selective inhibitory effect on PRMT5 in MTAP deleted cells, that comprises administering an effective amount of a compound of the Formula (I), or a pharmaceutically acceptable salt thereof, as defined herein, to a patient in need thereof.

Described herein are compounds that can bind to PRMT5 in the presence of MTA. In biochemical and cell based assays the compounds of the present specification are shown to be potent PRMT5 binders in the presence of MTA and may therefore be useful in the treatment of disorders mediated by PRMT5, in particular in the treatment of cancers such as lung cancer (for example NSCLC), lymphomas (for example DLBCL) and gastric cancers. In particular, the compounds according to the specification can be used in the treatment of CDKN2A/MTAP deleted cancers, i.e. those cancers in which the tumour suppressor gene cyclin dependent kinase inhibitor 2A (CDKN2A) has been homozygously deleted. The compounds according to the specification may equally be used in methods of treatment of patients that have a CDKN2A/MTAP deleted cancer.

The present specification also relates to processes for the manufacture of said compounds, to pharmaceutical compositions containing them, to methods of treatment comprising administering the said compounds to patients, for example humans, in need thereof, to use of compounds of formula (I) for the manufacture of medicaments, for example for use in the treatment of a patient suffering from a hyperproliferative disease such as cancer.

BRIEF DESCRIPTION OF DRAWINGS

In order that the invention can be better understood, reference is made herein to the following figure:

FIG. 1: A protein crystal structure of Example 1 and MTA bound to PRMT5. This protein crystal structure illustrates that the compounds of the present specification bind to PRMT5 together with MTA. Also visible is the stereochemistry of the spirocyclic ring system and key interactions of the inhibitor with residues such as Leu312, Glu435, Glu444, Ser578 and Phe580 of PRMT5.

Unless defined otherwise, all technical and scientific terms used herein have the same meaning as commonly understood by one of ordinary skill in the art to which this disclosure is related. For example, the *Concise Dictionary of Biomedicine and Molecular Biology*, Juo, Pei-Show, 2nd ed., 2002, CRC Press; *The Dictionary of Cell and Molecular Biology*, 3rd ed., 1999, Academic Press; and the Oxford *Dictionary of Biochemistry and Molecular Biology, Revised*, 2000, Oxford University Press, provide one of skill with a general dictionary of many of the terms used in this disclosure.

So that the present specification may be more readily understood, certain terms are explicitly defined below. In addition, definitions are set forth as appropriate throughout the specification.

Units, prefixes, and symbols are denoted in their Systeme International de Unites (SI) accepted form. Numeric ranges are inclusive of the numbers defining the range.

The term "pharmaceutical composition" refers to a preparation which is in such form as to permit the biological activity of the active ingredient to be expressed, and which contains no additional components which are unacceptably toxic to a subject to which the composition would be administered. Such compositions can be sterile. A pharmaceutical composition according to the present specification will comprise a compound of Formula (I), or a pharmaceutical acceptable salt thereof, and at least one pharmaceutically acceptable excipient.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a subject is successfully "treated" for cancer according to the methods of the present disclosure if the patient shows, e.g., total, partial, or transient remission of a certain type of cancer.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

As used herein the term "alkyl" refers to both straight and branched chain saturated hydrocarbon radicals having the specified number of carbon atoms. As used herein the term deuteroalkyl refers to an alkyl groups in which one or more, optionally all, hydrogens are replaced with deuterium atoms. As used herein the term haloalkyl refers to an alkyl groups in which one or more, optionally all, hydrogens are replaced with chlorine or fluorine atoms. As used herein the term fluoroalkyl refers to an alkyl groups in which one or more, optionally all, hydrogens are replaced with fluorine atoms. Example of preferred fluoroalkyl groups include $CH_2F$, $CHF_2$, $CF_3$, $CH_2CF_3$, $CF_2CH_3$ and $CF_2CF_3$. The term cycloalkyl refers to a saturated carbocycle, for example a cyclopropyl, cyclobutyl, cyclopentyl or cyclohexyl group.

The term acetylenyl refers to an ethynyl radical i.e. a —CCH group. The term alkynyl refers to a group containing a carbon-carbon triple bond.

In this specification the prefix $C_x$-$C_y$, as used in terms such as $C_x$-$C_y$ alkyl and the like where x and y are integers, indicates the numerical range of carbon atoms that are present in the group. For example, $C_1$-$C_4$ alkyl includes methyl, ethyl, n-propyl, i-propyl, n-butyl, s-butyl, i-butyl and t-butyl, while examples of $C_1$-$C_3$ alkyl groups include methyl, ethyl, n-propyl, and i-propyl. $C_1$-$C_4$ alkoxy groups include methoxy, ethoxy, n-propoxy, i-propoxy, n-butoxy, s-butoxy and t-butoxy. Examples of $C_1$-$C_3$ alkoxy groups include methoxy, ethoxy, n-propoxy and i-propoxy. Examples of $C_1$-$C_3$ fluoroalkyl groups include fluoromethyl, difluoromethyl, trifluoromethyl, 1,1-difluoroethyl and 2,2,2-trifluoroethyl. Examples of $C_1$-$C_3$ fluoroalkoxy groups include fluoromethoxy, difluoromethoxy, trifluoromethoxy and 2,2,2-trifluoroethoxy. A —O($C_1$-$C_3$deuterioalkyl) group is a partially or fully deuterated O-methyl, O-ethyl or O-n-propyl or O-i-propyl group. A $C_3$-$C_6$cycloalkyl group refers to a cyclopropyl, cyclobutyl, cyclopentyl or cyclohexyl group.

Unless specifically stated, the bonding of an atom or group may be any suitable atom of that group; for example, propyl includes prop-1-yl and prop-2-yl.

Heteroaryl as used herein refers to a [4n+2] aromatic ring containing at least one heteroatom selected from N, O or S. Examples of 5-membered heteroaryl groups include pyrrole, imidazole, pyrazole, 1,2,3-triazole, 1,2,4-triazole, oxazole, isoxazole, oxadiazole, thiazole, isothiazole, furan and thiazole. Examples of 6-membered heteroaryl groups include pyridine, pyridazine, pyrimidine and pyrazine.

Bicyclic heteroaryl as used herein refers to a [6,5] or [6,6] bicyclic heteroaryl group comprising one 6-membered ring fused to a 5- or 6-membered ring in which at least one of the two constituent rings contains at least one heteroatom selected from N, O or S and furthermore wherein a least one of the two constituent rings is a [4n+2] aromatic ring. A bicyclic heteroaryl group in this context is an aromatic group comprising two fused rings and containing 1, 2, 3 or 4 N atoms, or one O atom, or one S atom, or 1 N atom and one S atom, or 1 N atom and one O atom, or 2 N atoms and one S atom, or 2 N atoms and one O atom. Bicyclic heteroaryl groups include those groups where both fused rings are aromatic, or where one fused ring is aromatic and the other fused ring is partially or fully saturated. The said partially or fully saturated fused ring may also comprise a carbonyl group. The bicyclic heteroaryl groups may be a [6,5]-system in which a phenyl group or a 6-membered heteroaryl group is fused to a pyrrole, imidazole, pyrazole, 1,2,3-triazole, oxazole, isoxazole, oxadiazole, thiazole, isothiazole, furan and thiazole. Examples of bicyclic heteroaryl groups include indolyl, benzofuranyl, benzothienyl, benzoxazolyl, benzimidazolyl, benzotriazolyl, indazolyl, azaindolyl, azaindazolyl, pyrrolo[1,2-b]pyridazinyl, pyrrolo[2,3-b]pyridinyl, quinolinyl, isoquinolinyl, quinazolinyl, cinnolinyl, phthalazinyl, quinoxalinyl and naphthyridinyl.

As noted above Compounds of Formula (I) may possess a group $R^7$ that is a 5-membered heteroaryl group optionally substituted with Me, $C_1$-$C_3$ alkyl, F or Cl. In such cases the 5-membered heteroaryl group is preferably selected from optionally substituted pyrazole, pyrrole, imidazole, oxazole or thiazole, for example N-methyl pyrazole.

As noted above Compounds of Formula (I) may possess a group $R^8$ that is a 5-membered heteroaryl group optionally substituted with Me, $C_1$-$C_3$ alkyl, F or Cl. In such cases the 5-membered heteroaryl group is preferably selected from optionally substituted pyrazole, pyrrole, imidazole, oxazole or thiazole, for example methyl substituted thiazole.

As noted above Compounds of Formula (I) may possess a group $R^9$ or $R^{10}$ that is an optionally substituted phenyl, 5- or 6-membered heteroaryl, or bicyclic heteroaryl group. In such instances $R^9$ or $R^{10}$ may be substituted with 1, 2 or 3 substituents independently selected from F, Cl, Me, CN, $CF_3$, $C_1$-$C_3$ alkyl, $C_1$-$C_3$ fluoroalkyl or a 5-membered heteroaryl group.

For the avoidance of doubt, where multiple substituents are independently selected from a given group, the selected substituents may comprise the same substituents or different substituents from within the given group. By way of example only, where in the instance where $(R^1)_m$, and where m is 2, the two $R^1$ substituents could be the same, for instance both fluoro, or could be different, for instance one fluoro and one methyl.

For the further avoidance of doubt, the use of "z,900" in formulas of this specification denotes the point of attachment between different groups.

Where any embodiment within this specification includes a group which is said to be "optionally substituted", then a further embodiment will include that embodiment wherein the said group is unsubstituted. In the case where a group is optionally substituted the optional substituents may be selected from Me, $C_1$-$C_3$ alkyl, $C_3$-$C_6$ cycloalkyl, $C_1$-$C_3$ fluoroalkyl, F or Cl, OH, $OC_1$-$C_3$ alkoxy, OH, $NH_2$ and $N(C_1$-$C_3$ alkyl$)_2$.

Exemplary compounds of Formula I according to the specification are listed in Table 1 below

TABLE 1

Compounds of Formula (I)

| Example | Structure |
|---------|-----------|
| 1 | (S)-2-((5-Amino-6-fluoro-1H-pyrrolo[3,2-b]pyridin-2-yl)methyl)-5-fluoro-1'-(4-fluorobenzyl)spiro[isoindoline-1,3'-pyrrolidine]-2',3-dione |

TABLE 1-continued

Compounds of Formula (I)

| Example | Structure |
|---|---|
| 2 | 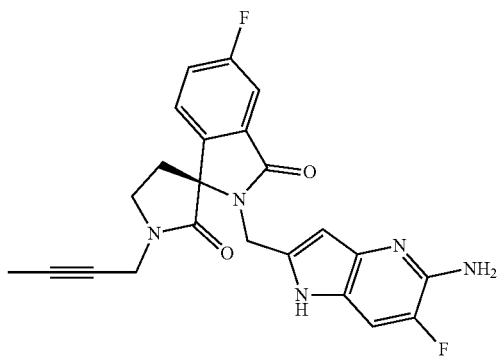 [SMILES: CC#CCN1CC[C@@]2(C1=O)c1ccc(F)cc1C(=O)N2Cc1cc2nc(N)c(F)cc2[nH]1]<br>(S)-2-((5-Amino-6-fluoro-1H-pyrrolo[3,2-b]pyridin-2-yl)methyl)-1'-(but-2-yn-1-yl)-5-fluorospiro[isoindoline-1,3'-pyrrolidine]-2',3-dione |
| 3 | 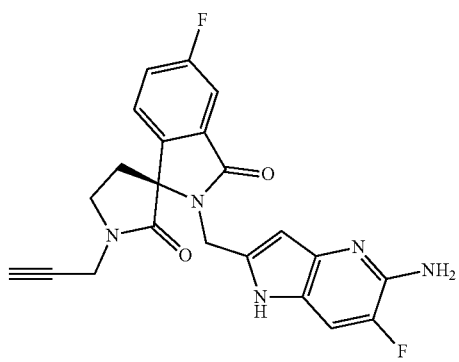 [SMILES: C#CCN1CC[C@@]2(C1=O)c1ccc(F)cc1C(=O)N2Cc1cc2nc(N)c(F)cc2[nH]1]<br>(S)-2-((5-Amino-6-fluoro-1H-pyrrolo[3,2-b]pyridin-2-yl)methyl)-5-fluoro-1'-(prop-2-yn-1-yl)spiro[isoindoline-1,3'-pyrrolidine]-2',3-dione |
| 4 | 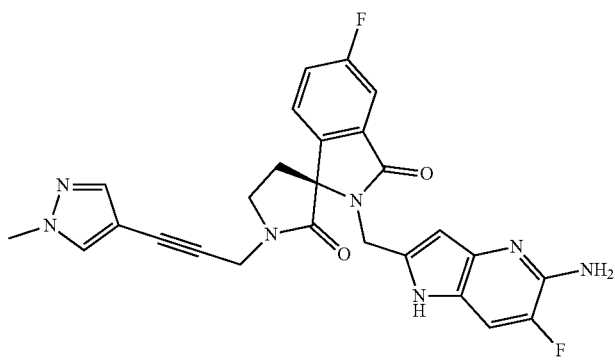 [SMILES: Cn1cc(C#CCN2CC[C@@]3(C2=O)c2ccc(F)cc2C(=O)N3Cc2cc3nc(N)c(F)cc3[nH]2)cn1]<br>(S)-2-((5-Amino-6-fluoro-1H-pyrrolo[3,2-b]pyridin-2-yl)methyl)-5-fluoro-1'-(3-(1-methyl-1H-pyrazol-4-yl)prop-2-yn-1-yl)spiro[isoindoline-1,3'-pyrrolidine]-2',3-dione |

TABLE 1-continued

Compounds of Formula (I)

| Example | Structure |
|---|---|
| 5 | 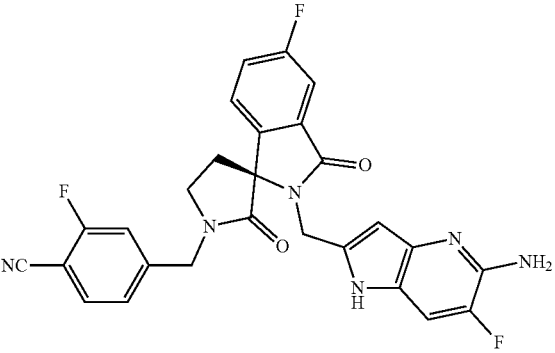 [SMILES: N#Cc1ccc(CN2CC[C@@]3(C2=O)c2ccc(F)cc2C(=O)N3Cc2cc3nc(N)c(F)cc3[nH]2)cc1F]<br>(S)-4-((2-((5-Amino-6-fluoro-1H-pyrrolo[3,2-b]pyridin-2-yl)methyl)-5-fluoro-2',3-dioxospiro[isoindoline-1,3'-pyrrolidin]-1'-yl)methyl)-2-fluorobenzonitrile |
| 6 | 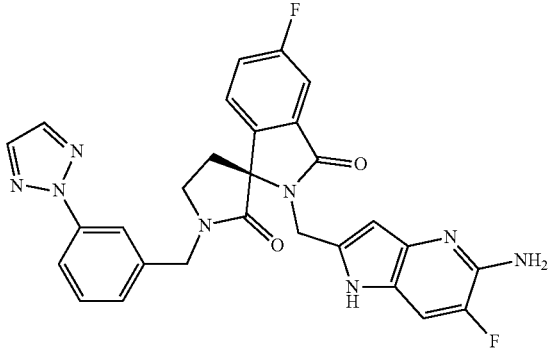 [SMILES: Nc1nc2cc(CN3C(=O)c4cc(F)ccc4[C@]34CCN(Cc3cccc(-n5nccn5)c3)C4=O)[nH]c2cc1F]<br>(S)-1'-(3-(2H-1,2,3-Triazol-2-yl)benzyl)-2-((5-amino-6-fluoro-1H-pyrrolo[3,2-b]pyridin-2-yl)methyl)-5-fluorospiro[isoindoline-1,3'-pyrrolidine]-2',3-dione |
| 7 | 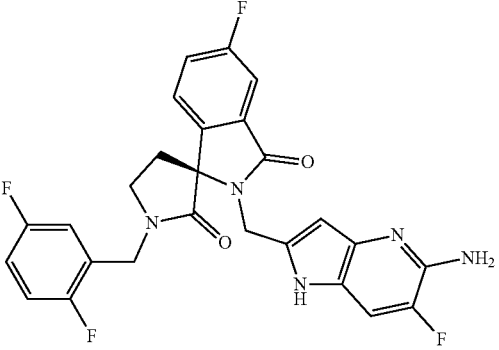 [SMILES: Nc1nc2cc(CN3C(=O)c4cc(F)ccc4[C@]34CCN(Cc3cc(F)ccc3F)C4=O)[nH]c2cc1F]<br>(S)-2-((5-Amino-6-fluoro-1H-pyrrolo[3,2-b]pyridin-2-yl)methyl)-1'-(2,5-difluorobenzyl)-5-fluorospiro[isoindoline-1,3'-pyrrolidine]-2',3-dione |

TABLE 1-continued

Compounds of Formula (I)

| Example | Structure |
|---|---|
| 8 | 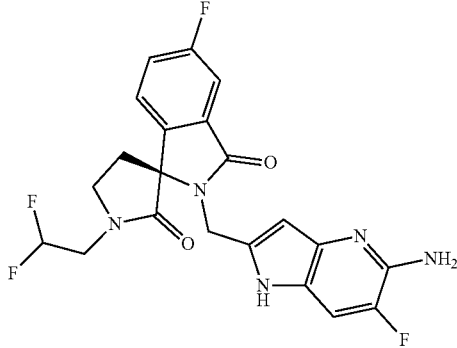 [SMILES: Nc1nc2cc(CN3C(=O)c4cc(F)ccc4[C@]34CCN(CC(F)F)C4=O)[nH]c2cc1F]<br>(S)-2-((5-Amino-6-fluoro-1H-pyrrolo[3,2-b]pyridin-2-yl)methyl)-1'-(2,2-difluoroethyl)-5-fluorospiro[isoindoline-1,3'-pyrrolidine]-2',3-dione |
| 9 | 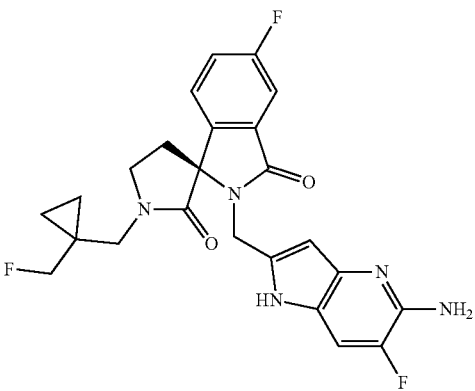 [SMILES: Nc1nc2cc(CN3C(=O)c4cc(F)ccc4[C@]34CCN(CC3(CF)CC3)C4=O)[nH]c2cc1F]<br>(S)-2-((5-Amino-6-fluoro-1H-pyrrolo[3,2-b]pyridin-2-yl)methyl)-5-fluoro-1'-((1-(fluoromethyl)cyclopropyl)methyl)spiro[isoindoline-1,3'-pyrrolidine]-2',3-dione |
| 10 | 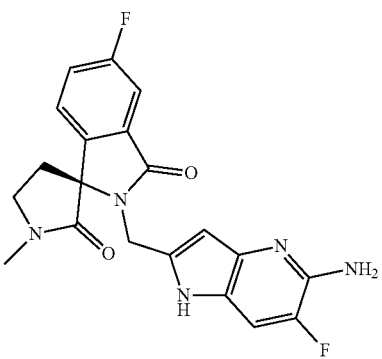 [SMILES: CN1CC[C@@]2(C1=O)c1ccc(F)cc1C(=O)N2Cc1cc2nc(N)c(F)cc2[nH]1]<br>(S)-2-((5-Amino-6-fluoro-1H-pyrrolo[3,2-b]pyridin-2-yl)methyl)-5-fluoro-1'-methylspiro[isoindoline-1,3'-pyrrolidine]-2',3-dione |

TABLE 1-continued

Compounds of Formula (I)

| Example | Structure |
|---|---|
| 11 | 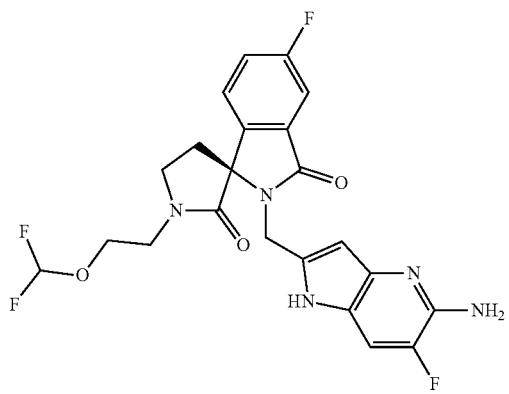 [SMILES: Nc1nc2cc(CN3C(=O)c4cc(F)ccc4[C@]34CCN(CCOC(F)F)C4=O)[nH]c2cc1F]<br>(S)-2-((5-Amino-6-fluoro-1H-pyrrolo[3,2-b]pyridin-2-yl)methyl)-1'-(2-(difluoromethoxy)ethyl)-5-fluorospiro[isoindoline-1,3'-pyrrolidine]-2',3-dione |
| 12 | 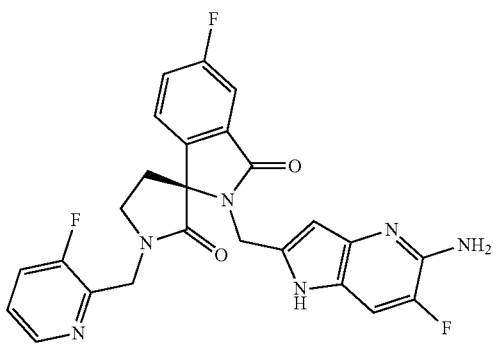 [SMILES: Nc1nc2cc(CN3C(=O)c4cc(F)ccc4[C@]34CCN(Cc3ncccc3F)C4=O)[nH]c2cc1F]<br>(S)-2-((5-Amino-6-fluoro-1H-pyrrolo[3,2-b]pyridin-2-yl)methyl)-5-fluoro-1'-((3-fluoropyridin-2-yl)methyl)spiro[isoindoline-1,3'-pyrrolidine]-2',3-dione |
| 13 | 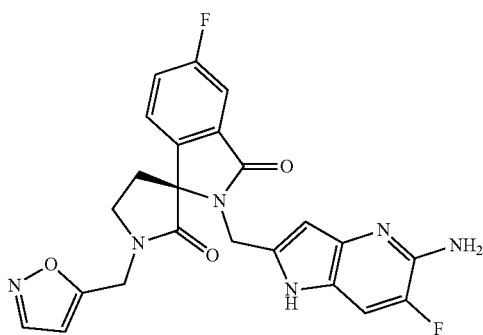 [SMILES: Nc1nc2cc(CN3C(=O)c4cc(F)ccc4[C@]34CCN(Cc3ccno3)C4=O)[nH]c2cc1F]<br>(S)-2-((5-Amino-6-fluoro-1H-pyrrolo[3,2-b]pyridin-2-yl)methyl)-5-fluoro-1'-(isoxazol-5-ylmethyl)spiro[isoindoline-1,3'-pyrrolidine]-2',3-dione |

TABLE 1-continued

Compounds of Formula (I)

| Example | Structure |
|---|---|
| 14 | 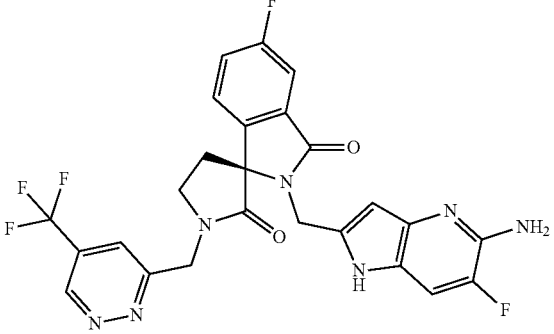<br>(S)-2-((5-Amino-6-fluoro-1H-pyrrolo[3,2-b]pyridin-2-yl)methyl)-5-fluoro-1'-((5-(trifluoromethyl)pyridazin-3-yl)methyl)spiro[isoindoline-1,3'-pyrrolidine]-2',3-dione |
| 15 | 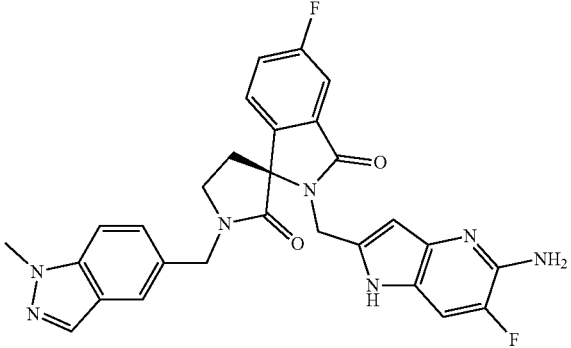 [SMILES: Cn1ncc2cc(CN3CC[C@@]4(C3=O)c3ccc(F)cc3C(=O)N4Cc3cc4nc(N)c(F)cc4[nH]3)ccc21]<br>(S)-2-((5-Amino-6-fluoro-1H-pyrrolo[3,2-b]pyridin-2-yl)methyl)-5-fluoro-1'-((1-methyl-1H-indazol-5-yl)methyl)spiro[isoindoline-1,3'-pyrrolidine]-2',3-dione |
| 16 | 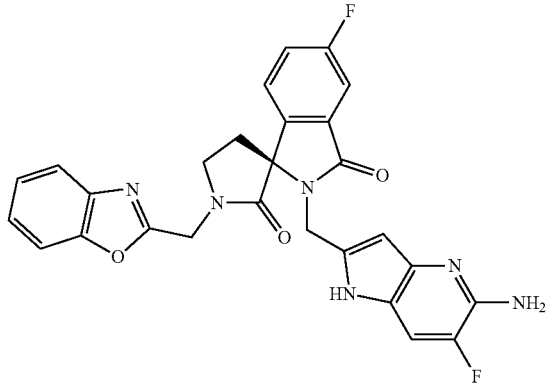 [SMILES: Nc1nc2cc(CN3C(=O)c4cc(F)ccc4[C@]34CCN(Cc3nc5ccccc5o3)C4=O)[nH]c2cc1F]<br>(S)-2-((5-Amino-6-fluoro-1H-pyrrolo[3,2-b]pyridin-2-yl)methyl)-1'-(benzo[d]oxazol-2-ylmethyl)-5-fluorospiro[isoindoline-1,3'-pyrrolidine]-2',3-dione |

TABLE 1-continued

Compounds of Formula (I)

| Example | Structure |
|---|---|
| 17 | 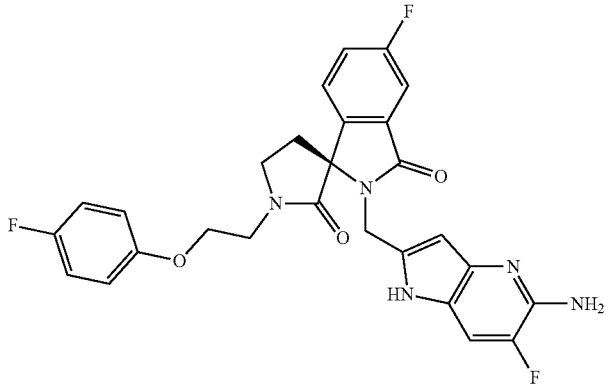 [SMILES: Nc1nc2cc(CN3C(=O)c4cc(F)ccc4[C@]34CCN(CCOc3ccc(F)cc3)C4=O)[nH]c2cc1F]<br>(S)-2-((5-Amino-6-fluoro-1H-pyrrolo[3,2-b]pyridin-2-yl)methyl)-5-fluoro-1'-(2-(4-fluorophenoxy)ethyl)spiro[isoindoline-1,3'-pyrrolidine]-2',3-dione |
| 18 | 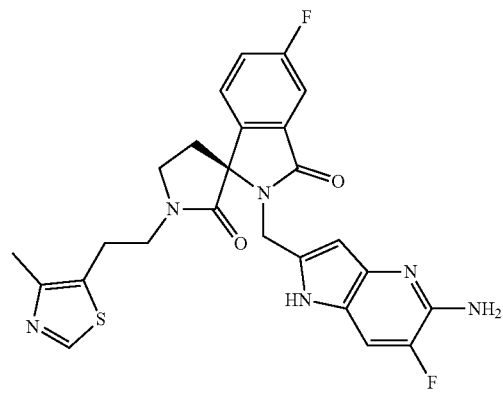 [SMILES: Cc1ncsc1CCN1CC[C@@]2(C1=O)c1ccc(F)cc1C(=O)N2Cc1cc2nc(N)c(F)cc2[nH]1]<br>(S)-2-((5-Amino-6-fluoro-1H-pyrrolo[3,2-b]pyridin-2-yl)methyl)-5-fluoro-1'-(2-(4-methylthiazol-5-yl)ethyl)spiro[isoindoline-1,3'-pyrrolidine]-2',3-dione |
| 19 | 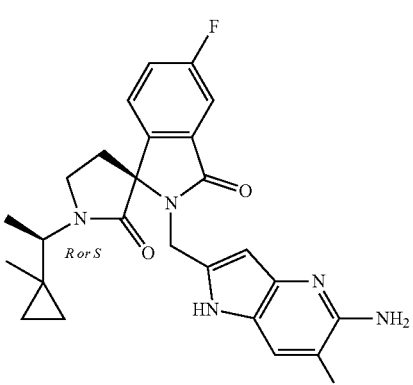<br>Isomer 2<br>(S)-2-((5-Amino-6-fluoro-1H-pyrrolo[3,2-b]pyridin-2-yl)methyl)-5-fluoro-1'-((R*)-1-(1-methylcyclopropyl)ethyl)spiro[isoindoline-1,3'-pyrrolidine]-2',3-dione |

TABLE 1-continued

Compounds of Formula (I)

| Example | Structure |
|---|---|
| 20 | 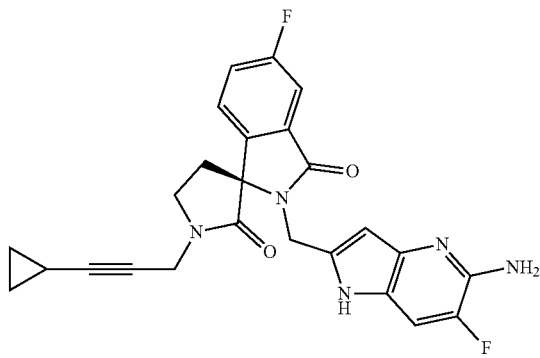 [SMILES: Nc1nc2cc(CN3C(=O)c4cc(F)ccc4[C@]34CCN(CC#CC3CC3)C4=O)[nH]c2cc1F]<br>(S)-2-((5-Amino-6-fluoro-1H-pyrrolo[3,2-b]pyridin-2-yl)methyl)-1'-(3-cyclopropylprop-2-yn-1-yl)-5-fluorospiro[isoindoline-1,3'-pyrrolidine]-2',3-dione |
| 21 | 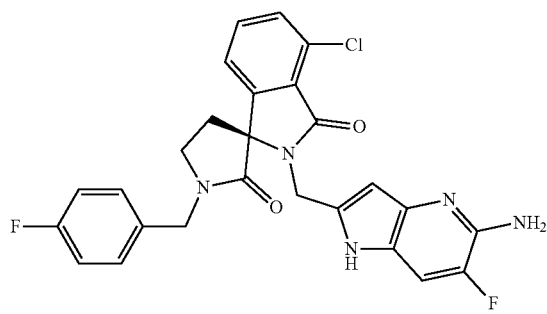 [SMILES: Nc1nc2cc(CN3C(=O)c4c(Cl)cccc4[C@]34CCN(Cc3ccc(F)cc3)C4=O)[nH]c2cc1F]<br>(S)-2-((5-Amino-6-fluoro-1H-pyrrolo[3,2-b]pyridin-2-yl)methyl)-4-chloro-1'-(4-fluorobenzyl)spiro[isoindoline-1,3'-pyrrolidine]-2',3-dione |
| 22 | 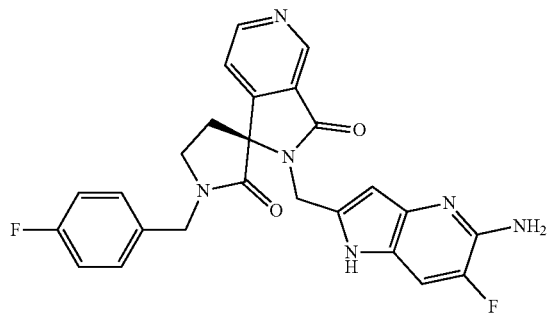 [SMILES: Nc1nc2cc(CN3C(=O)c4cnccc4[C@]34CCN(Cc3ccc(F)cc3)C4=O)[nH]c2cc1F]<br>(S)-2'-((5-Amino-6-fluoro-1H-pyrrolo[3,2-b]pyridin-2-yl)methyl)-1-(4-fluorobenzyl)spiro[pyrrolidine-3,1'-pyrrolo[3,4-c]pyridine]-2,3'(2'H)-dione |

TABLE 1-continued

Compounds of Formula (I)

| Example | Structure |
|---------|-----------|
| 23 | 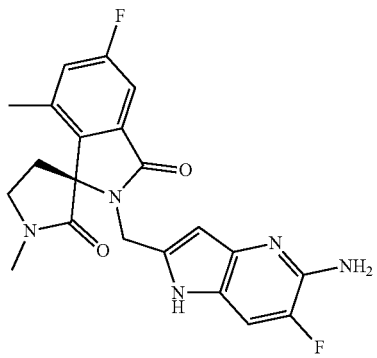 [SMILES: Cc1cc(F)cc2c1[C@]1(CCN(C)C1=O)N(Cc1cc3nc(N)c(F)cc3[nH]1)C2=O]<br>(S)-2-((5-Amino-6-fluoro-1H-pyrrolo[3,2-b]pyridin-2-yl)methyl)-5-fluoro-1',7-dimethylspiro[isoindoline-1,3'-pyrrolidine]-2',3-dione |
| 24 | 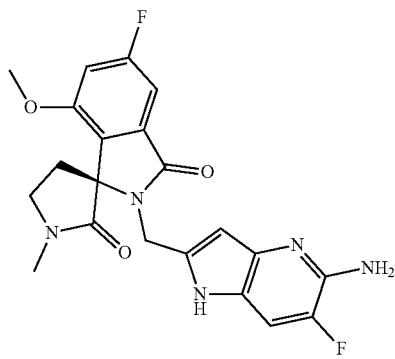 [SMILES: COc1cc(F)cc2c1[C@]1(CCN(C)C1=O)N(Cc1cc3nc(N)c(F)cc3[nH]1)C2=O]<br>(S)-2-((5-Amino-6-fluoro-1H-pyrrolo[3,2-b]pyridin-2-yl)methyl)-5-fluoro-7-methoxy-1'-methylspiro[isoindoline-1,3'-pyrrolidine]-2',3-dione |
| 25 | 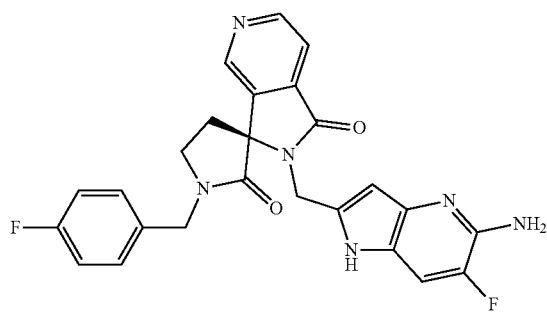 [SMILES: Nc1nc2cc(CN3C(=O)c4ccncc4[C@]34CCN(Cc3ccc(F)cc3)C4=O)[nH]c2cc1F]<br>(S)-2'-((5-Amino-6-fluoro-1H-pyrrolo[3,2-b]pyridin-2-yl)methyl)-1-(4-fluorobenzyl)spiro[pyrrolidine-3,3'-pyrrolo[3,4-c]pyridine]-1',2(2'H)-dione |

TABLE 1-continued

Compounds of Formula (I)

| Example | Structure |
|---|---|
| 26 | 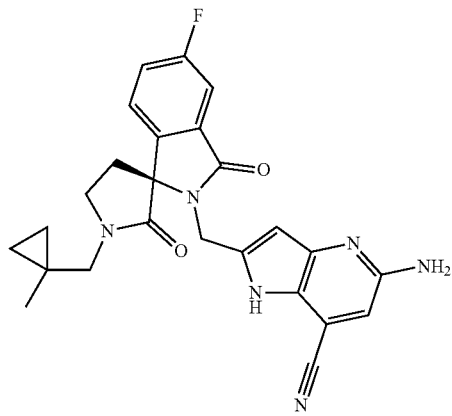 [SMILES: CC1(CN2CC[C@@]3(C2=O)c2ccc(F)cc2C(=O)N3Cc2cc3nc(N)cc(C#N)c3[nH]2)CC1]<br>(S)-5-Amino-2-((5-fluoro-1'-((1-methylcyclopropyl)methyl)-2',3-dioxospiro[isoindoline-1,3'-pyrrolidin]-2-yl)methyl)-1H-pyrrolo[3,2-b]pyridine-7-carbonitrile |
| 27 | 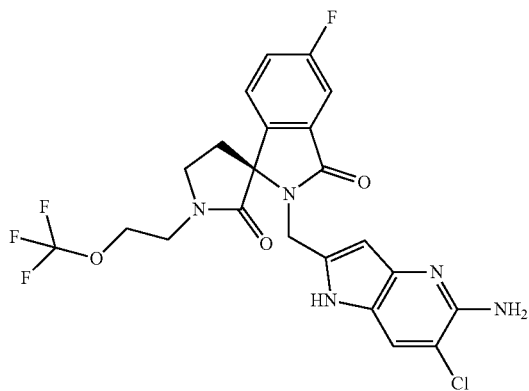 [SMILES: Nc1nc2cc(CN3C(=O)c4cc(F)ccc4[C@]34CCN(CCOC(F)(F)F)C4=O)[nH]c2cc1Cl]<br>(S)-2-((5-Amino-6-chloro-1H-pyrrolo[3,2-b]pyridin-2-yl)methyl)-5-fluoro-1'-(2-(trifluoromethoxy)ethyl)spiro[isoindoline-1,3'-pyrrolidine]-2',3-dione |
| 28 | 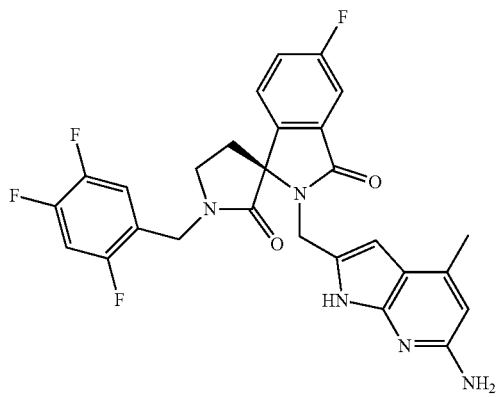 [SMILES: Cc1cc(N)nc2[nH]c(CN3C(=O)c4cc(F)ccc4[C@]34CCN(Cc3cc(F)c(F)cc3F)C4=O)cc12]<br>(S)-2-((6-Amino-4-methyl-1H-pyrrolo[2,3-b]pyridin-2-yl)methyl)-5-fluoro-1'-(2,4,5-trifluorobenzyl)spiro[isoindoline-1,3'-pyrrolidine]-2',3-dione |

TABLE 1-continued

Compounds of Formula (I)

| Example | Structure |
|---|---|
| 29 | 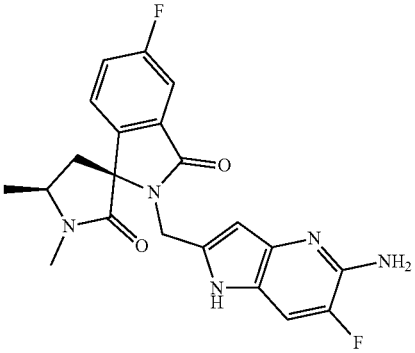 [SMILES: C[C@H]1C[C@@]2(C(=O)N1C)c1ccc(F)cc1C(=O)N2Cc1cc2nc(N)c(F)cc2[nH]1]<br>(1S,5'S)-2-((5-Amino-6-fluoro-1H-pyrrolo[3,2-b]pyridin-2-yl)methyl)-5-fluoro-1',5'-dimethylspiro[isoindoline-1,3'-pyrrolidine]-2',3-dione |

As can be seen from Table 1, the stereochemistry of the quaternary carbon is always presented as having the S-configuration. Although the absolute stereochemistry of each and every example has not been unambiguously established, in all cases where that has been possible compounds with (S)-configuration has proven more active than the corresponding (R)-isomers. The protein crystal structure of FIG. 1 confirms this, and enantiomeric syntheses to obtain the (S)-isomer have been performed in many instance. Nonetheless the skilled reader will understand that both possible isomers are encompassed by the specification and, furthermore, that the most active isomers are preferred embodiments. Preferred compounds of the specification have the S-configuration as shown below.

The interactions of such compounds with PRMT5 when bound in conjunction with MTA can be seen in FIG. 1. In more detail, Example 1 was co-crystallized with the MTA-bound form of the PRMT5 protein and a protein structure was obtained using standard techniques. The protein crystal structure reveals that the azaindole headgroup of the inhibitor binds in the substrate active site and makes key interactions in the 'Arginine pocket' (protonated N-4 and 5-amino group have hydrogen-bond-donor interactions with Glu444, and the 5-amino group also makes a hydrogen-bond-donor interaction with the backbone carbonyl group of Glu437). It appears that there may well also be an interaction of this 5-amino group with the sulfur atom of the MTA molecule also bound to PRMT5, and this may, at least in part, explain the 'MTA-synergistic' nature of the PRMT5 inhibitor compounds according to the specification. Further interactions between Example 1 and the PRMT5 protein and include an hydrogen bond donor interaction between N-1 of the azaindole and the backbone carbonyl of Ser578. The carbonyl of the central isoindolinone group also makes a hydrogen-bond-acceptor interaction with the backbone NH of Leu312. The X-ray protein crystal structure also demonstrates that the S-configured quaternary centre is important to the optimised fit of the inhibitors in the PRMT5 pocket. Notably, the spiro lactam carbonyl is able in this configuration to make a hydrogen-bond-acceptor interaction with the backbone NH of Phe580.

As noted above, according to a first aspect of the specification there is provided a compound of Formula (I), or a pharmaceutically acceptable salt thereof,

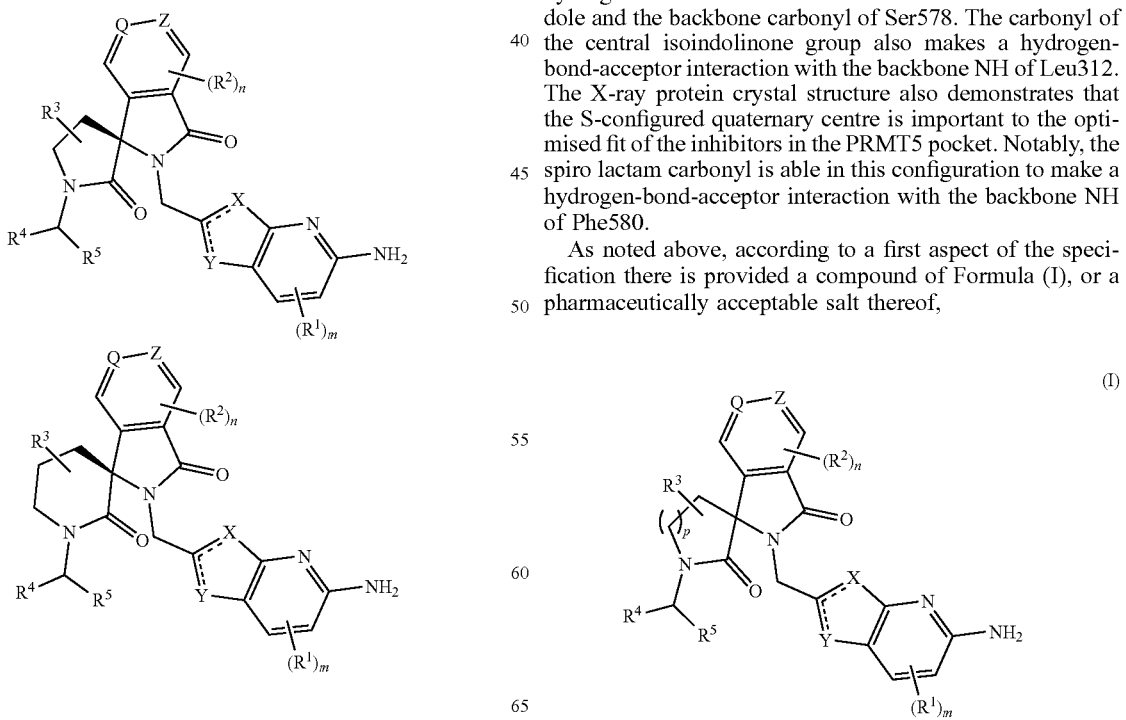

wherein:

the ring containing X and Y is a pyrrole and X is NH and Y is CH or X is CH and Y is NH;

Z is selected from CH, CF, CCl or, if Q is not N, N;

Q is selected from CH, CF, CCl or, if Z is not N, N;

m is 0, 1 or 2;

n is 0, 1 or 2;

p is 1 or 2;

$R^1$ is in each occurrence independently selected from F, Cl, CN, Me, $CF_3$, $C_1$-$C_3$ alkyl, cyclopropyl, $C_1$-$C_3$ fluoroalkyl, OMe or $C_1$-$C_3$ alkoxy;

$R^2$ is in each occurrence independently selected from F, Cl, Me, MeO and $CF_3$;

$R^3$ is H, Me, $C_1$-$C_3$ alkyl or $C_1$-$C_3$ fluoroalkyl;

$R^4$ is H, Me or $C_1$-$C_3$ alkyl;

$R^5$ is H, Me, $C_1$-$C_3$ alkyl, $C_1$-$C_3$ fluoroalkyl, $CH_2OMe$, $CH_2OCHF_2$, $CH_2OCF_3$, $CH_2O(C_1$-$C_3$ alkyl), $CH_2O(C_1$-$C_3$ fluoroalkyl), $C(CH_2CH_2)R^6$, $CCR^7$, $CH_2R^8$, $R^9$ or $CH_2R^{10}$;

$R^6$ is H, Me, $CH_2F$, $CHF_2$, $CF_3$, $CH_2OH$ or $CH_2OMe$;

$R^7$ is H, Me, cyclopropyl, $C_1$-$C_3$ alkyl, $C_1$-$C_3$ fluoroalkyl, $C_3$-$C_6$ cycloalkyl or a 5-membered heteroaryl group optionally substituted with Me, $C_1$-$C_3$ alkyl, F or Cl;

$R^8$ is a 5-membered heteroaryl optionally substituted with Me, $C_1$-$C_3$ alkyl, F or Cl;

$R^9$ is an optionally substituted phenyl, 5- or 6-membered heteroaryl, or bicyclic heteroaryl group; and $R^{10}$ is an optionally substituted phenyl, 5- or 6-membered heteroaryl, or bicyclic heteroaryl group.

In embodiments, the compound of Formula (I) is a compound with the S-configuration presented as Formula (Ia) below.

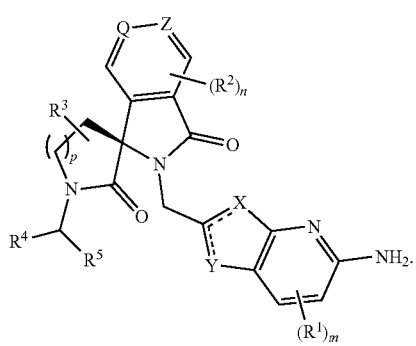

(Ia)

For ease of reference, statements herein below referring to a compound of Formula (I) or (Ia), such as is the case for a compound of Formula (Ib) immediately below, will be understood to relate to a compound of Formula (I) in which in the stereochemistry is not specified (by reference to a compound of Formula (I)) or in which the stereochemistry is set as the S-configuration (by reference to a compound of Formula (Ia)).

In embodiments, the compound of Formula (I) or (Ia), is a compound of Formula (Ib) in which p is 1.

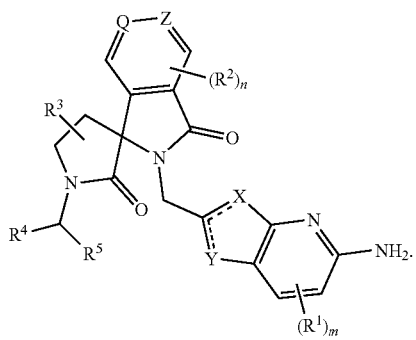

(Ib)

In embodiments, the compound of Formula (I) or (Ia), is a compound of Formula (Ic) in which p is 2.

In embodiments, the compound of Formula (I), (Ia), (Ib) or (Ic) is a compound of Formula (Id) in which Y is N and p is 1.

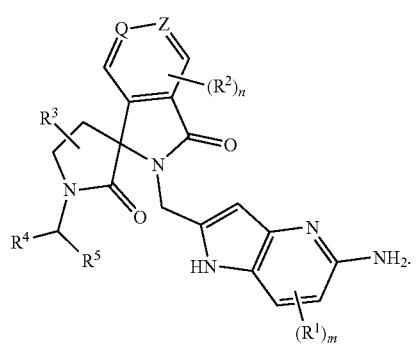

(Id)

In embodiments, the compound of Formula (I), (Ia), (Ib), (Ic) or (Id) is a compound of Formula (Ie) in which X is N and p is 1.

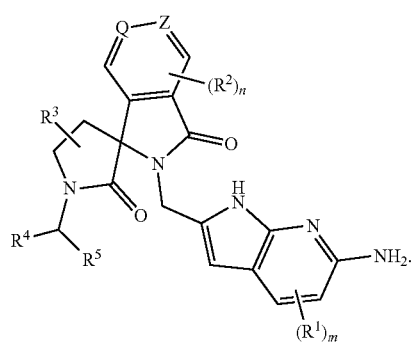

(Ie)

In embodiments, the compound of Formula (I), (Ia), (Ib), (Ic), (Id) or (Ie) is a compound of Formula (If) in which Z is CF and Q is CH.

(If)

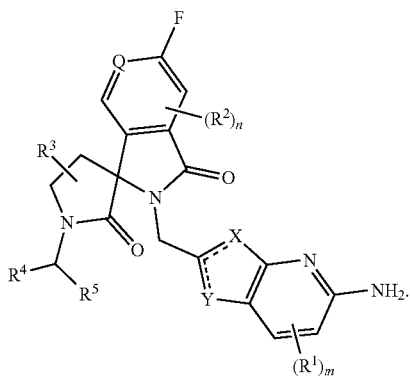

In embodiments, the compound of Formula (I), (Ia), (Ib), (Ic), (Id), (Ie) or (If) is a compound of Formula (Ig) in which n is 0.

In embodiments, the compound of Formula (I), (Ia), (Ib), (Ic), (Id), (Ie), (If) or (Ig) is a compound of Formula (Ih) in which $R^1$ is F.

In embodiments, the compound of Formula (I), (Ia), (Ib), (Ic), (Id), (Ie), (If), (Ig) or (Ih) is a compound of Formula (Ii) in which m is 1. In such embodiments the $R^1$ group may be ortho- to the $NH_2$ group as shown below for the instance where Q is CH, Z is CF and p is 1.

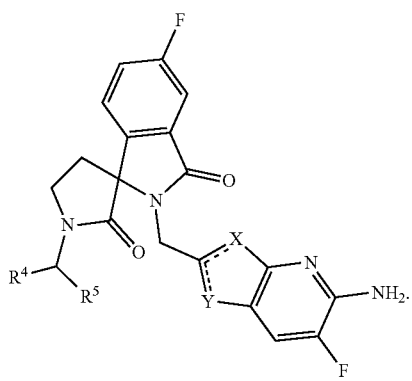

In embodiments, the compound of Formula (I), (Ia), (Ib), (Ic), (Id), (Ie), (If), (Ig), (Ih) or (Ii) is a compound of Formula (Ij) in which $R^3$ is H.

In embodiments, the compound of Formula (I), (Ia), (Ib), (Ic), (Id), (Ie), (If), (Ig), (Ih), (Ii) or (Ij) is a compound of Formula (Ik) in which $R^4$ is H or Me.

In embodiments, the compound of Formula (I), (Ia), (Ib), (Ic), (Id), (Ie), (If), (Ig), (Ih), (Ii), (Ij) or (Ik) is a compound of Formula (Il) in which $R^5$ is $R^9$ and $R^9$ is selected from:

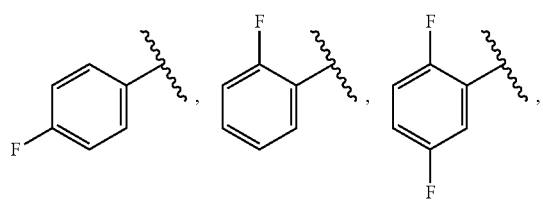

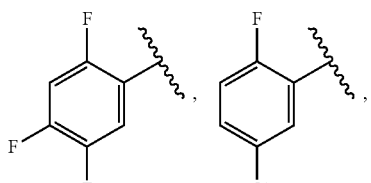

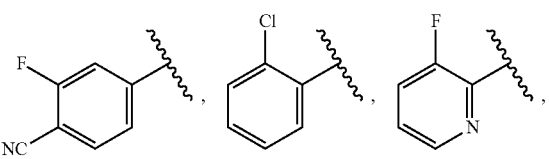

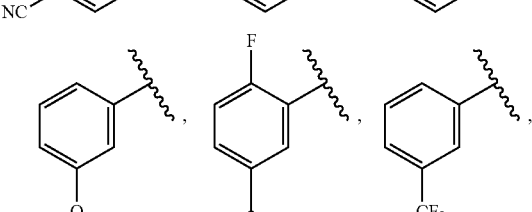

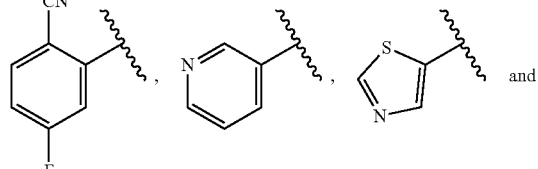

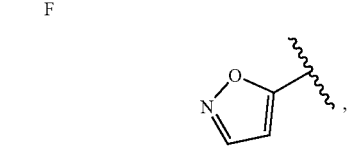

In embodiments, the compound of Formula (I), (Ia), (Ib), (Ic), (Id), (Ie), (If), (Ig), (Ih), (Ii), (Ij) or (Ik) is a compound of Formula (Im) in which $R^5$ is $R^9$ and $R^9$ is selected from:

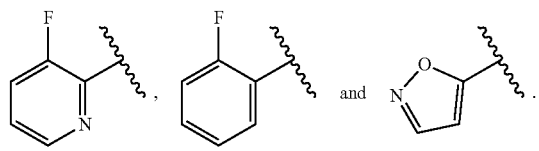 [SMILES: *c1ncccc1F ; "," ; *c1ccccc1F ; *c1ccno1 ; "."]

In embodiments, the compound of Formula (I), (Ia), (Ib), (Ic), (Id), (Ie), (If), (Ig), (Ih), (Ii), (Ij) or (Ik) is a compound of Formula (In) in which $R^5$ is selected from

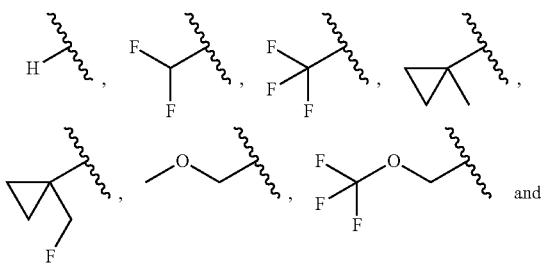

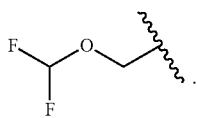

In embodiments, the compound of Formula (I), (Ia), (Ib), (Ic), (Id), (Ie), (If), (Ig), (Ih), (Ii), (Ij) or (Ik) is a compound of Formula (Io) in which $R^5$ is selected from

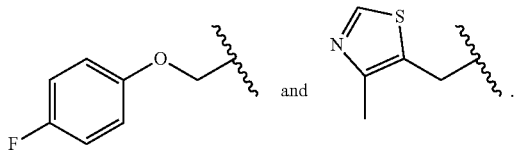

In embodiments, the compound of Formula (I), (Ia), (Ib), (Ic), (Id), (Ie), (If), (Ig), (Ih), (Ii), (Ij) or (Ik) is a compound of Formula (Ip) in which $R^5$ is selected from

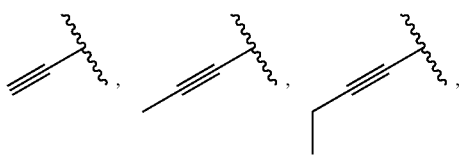

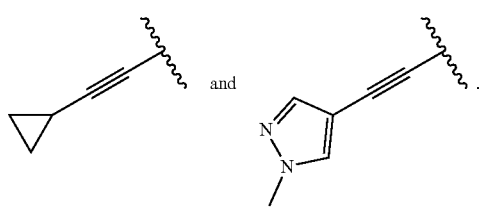

In embodiments, the compound of Formula (I), (Ia), (Ib), (Ic), (Id), (Ie), (If), (Ig), (Ih), (Ii), (Ij) or (Ik) is a compound of Formula (Iq) in which $R^5$ is selected from

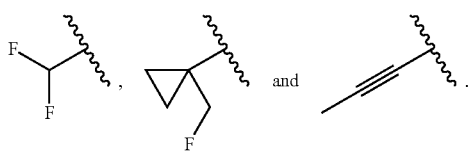

In embodiments, the compound of Formula (I) is a compound of Formula (Ir)

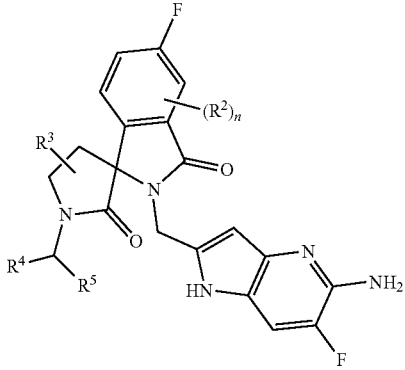

wherein:

n is 0, 1 or 2;

$R^2$ is in each occurrence independently selected from F, Cl, Me, MeO and $CF_3$;

$R^3$ is H, Me, $C_1$-$C_3$ alkyl or $C_1$-$C_3$ fluoroalkyl;

$R^4$ is H, Me or $C_1$-$C_3$ alkyl;

$R^5$ is H, Me, $C_1$-$C_3$ alkyl, $C_1$-$C_3$ fluoroalkyl, $CH_2OMe$, $CH_2OCHF_2$, $CH_2OCF_3$, $CH_2O(C_1$-$C_3$ alkyl), $CH_2O$ ($C_1$-$C_3$ fluoroalkyl), $C(CH_2CH_2)R^6$, $CCR^7$, $CH_2R^8$, $R^9$ or $CH_2R^{10}$;

$R^6$ is H, Me, $CH_2F$, $CHF_2$, $CF_3$, $CH_2OH$ or $CH_2OMe$;

$R^7$ is H, Me, cyclopropyl, $C_1$-$C_3$ alkyl, $C_1$-$C_3$ fluoroalkyl, $C_3$-$C_6$ cycloalkyl or a 5-membered heteroaryl group optionally substituted with Me, $C_1$-$C_3$ alkyl, F or Cl;

$R^8$ is a 5-membered heteroaryl optionally substituted with Me, $C_1$-$C_3$ alkyl, F or Cl;

$R^9$ is an optionally substituted phenyl, 5- or 6-membered heteroaryl, or bicyclic heteroaryl group; and $R^{10}$ is an optionally substituted phenyl, 5- or 6-membered heteroaryl, or bicyclic heteroaryl group.

In embodiments, the compound of Formula (Ir) is a compound of Formula (Is) in which $R^5$ is selected from

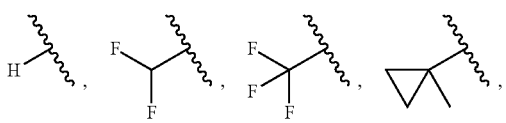

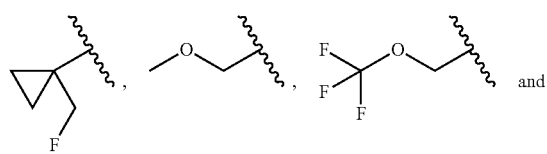

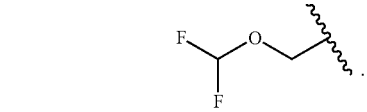

In embodiments, the compound of Formula (Ir) is a compound of Formula (It) in which $R^5$ is selected from

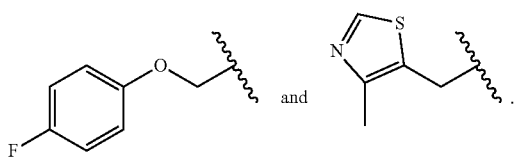

In embodiments, the compound of Formula (Ir) is a compound of Formula (Iu) in which $R^5$ is selected from

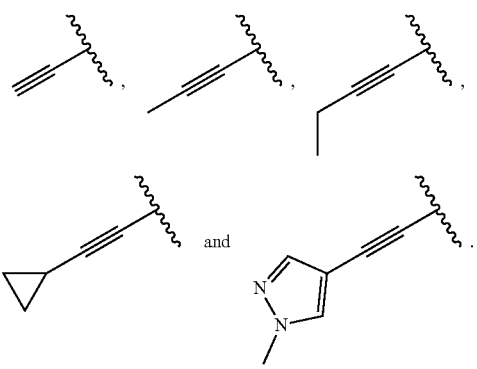

In embodiments, the compound of Formula (Ir) is a compound of Formula (Iv) in which $R^5$ is selected from

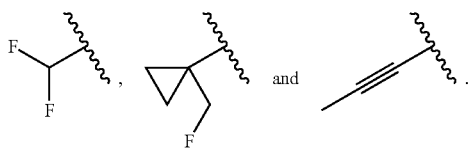

In embodiments, the compound of Formula (Ir) is a compound of Formula (Iw) in which $R^5$ is $R^9$ and is selected from

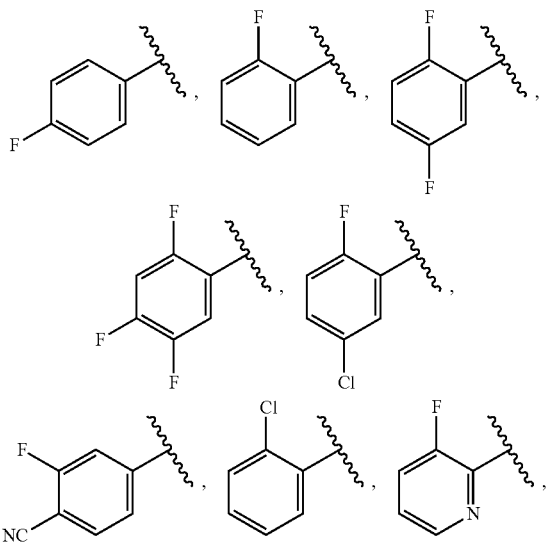

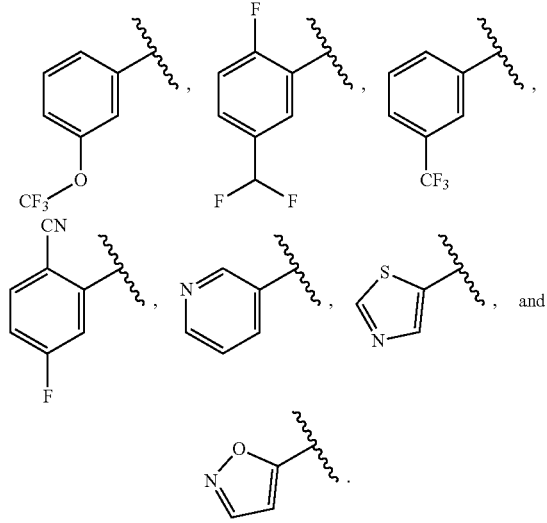

In embodiments, the compound of Formula (Ir) is a compound of Formula (Ix) in which $R^5$ is $R^9$ and is selected from

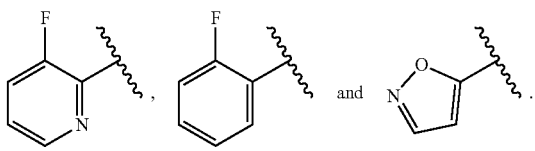 [SMILES: *c1ncccc1F ; "," ; *c1ccccc1F ; *c1ccno1 ; "."]

In embodiments, the compound of Formula (I) is selected from:
- (S)-2-((5-Amino-6-fluoro-1H-pyrrolo[3,2-b]pyridin-2-yl)methyl)-5-fluoro-1'-(4-fluorobenzyl)spiro[isoindoline-1,3'-pyrrolidine]-2',3-dione;
- (S)-2-((5-Amino-6-fluoro-1H-pyrrolo[3,2-b]pyridin-2-yl)methyl)-1'-(but-2-yn-1-yl)-5-fluorospiro[isoindoline-1,3'-pyrrolidine]-2',3-dione;
- (S)-2-((5-Amino-6-fluoro-1H-pyrrolo[3,2-b]pyridin-2-yl)methyl)-5-fluoro-1'-(prop-2-yn-1-yl)spiro[isoindoline-1,3'-pyrrolidine]-2',3-dione;
- (S)-2-((5-Amino-6-fluoro-1H-pyrrolo[3,2-b]pyridin-2-yl)methyl)-5-fluoro-1'-(3-(1-methyl-1H-pyrazol-4-yl)prop-2-yn-1-yl)spiro[isoindoline-1,3'-pyrrolidine]-2',3-dione;
- (S)-4-((2-((5-amino-6-fluoro-1H-pyrrolo[3,2-b]pyridin-2-yl)methyl)-5-fluoro-2',3-dioxospiro[isoindoline-1,3'-pyrrolidin]-1'-yl)methyl)-2-fluorobenzonitrile;
- (S)-1'-(3-(2H-1,2,3-Triazol-2-yl)benzyl)-2-((5-amino-6-fluoro-1H-pyrrolo[3,2-b]pyridin-2-yl)methyl)-5-fluorospiro[isoindoline-1,3'-pyrrolidine]-2',3-dione;
- (S)-2-((5-Amino-6-fluoro-1H-pyrrolo[3,2-b]pyridin-2-yl)methyl)-1'-(2,5-difluorobenzyl)-5-fluorospiro[isoindoline-1,3'-pyrrolidine]-2',3-dione;
- (S)-2-((5-Amino-6-fluoro-1H-pyrrolo[3,2-b]pyridin-2-yl)methyl)-1'-(2,2-difluoroethyl)-5-fluorospiro[isoindoline-1,3'-pyrrolidine]-2',3-dione;
- (S)-2-((5-Amino-6-fluoro-1H-pyrrolo[3,2-b]pyridin-2-yl)methyl)-5-fluoro-1'-((1-(fluoromethyl)cyclopropypm-ethyl)spiro[isoindoline-1,3'-pyrrolidine]-2',3-dione;
- (S)-2-((5-Amino-6-fluoro-1H-pyrrolo[3,2-b]pyridin-2-yl)methyl)-5-fluoro-1'-methylspiro[isoindoline-1,3'-pyrrolidine]-2',3-dione;

(S)-2-((5-Amino-6-fluoro-1H-pyrrolo[3,2-b]pyridin-2-yl)methyl)-1'-(2-(difluoromethoxy)ethyl)-5-fluorospiro[isoindoline-1,3'-pyrrolidine]-2',3-dione;

(S)-2-((5-Amino-6-fluoro-1H-pyrrolo[3,2-b]pyridin-2-yl)methyl)-5-fluoro-1'-((3-fluoropyridin-2-yl)methyl)spiro[isoindoline-1,3'-pyrrolidine]-2',3-dione;

(S)-2-((5-Amino-6-fluoro-1H-pyrrolo[3,2-b]pyridin-2-yl)methyl)-5-fluoro-1'-(isoxazol-5-ylmethyl)spiro[isoindoline-1,3'-pyrrolidine]-2',3-dione;

(S)-2-((5-Amino-6-fluoro-1H-pyrrolo[3,2-b]pyridin-2-yl)methyl)-5-fluoro-1'-((5-(trifluoromethyl)pyridazin-3-yl)methyl)spiro[isoindoline-1,3'-pyrrolidine]-2',3-dione (S)-2-((5-Amino-6-fluoro-1H-pyrrolo[3,2-b]pyridin-2-yl)methyl)-5-fluoro-1'-((1-methyl-1H-indazol-5-yl)methyl)spiro[isoindoline-1,3'-pyrrolidine]-2',3-dione;

(S)-2-((5-Amino-6-fluoro-1H-pyrrolo[3,2-b]pyridin-2-yl)methyl)-1'-(benzo[d]oxazol-2-ylmethyl)-5-fluorospiro[isoindoline-1,3'-pyrrolidine]-2',3-dione;

(S)-2-((5-Amino-6-fluoro-1H-pyrrolo[3,2-b]pyridin-2-yl)methyl)-5-fluoro-1'-(2-(4-fluorophenoxy)ethyl)spiro[isoindoline-1,3'-pyrrolidine]-2',3-dione;

(S)-2-((5-Amino-6-fluoro-1H-pyrrolo[3,2-b]pyridin-2-yl)methyl)-5-fluoro-1'-(2-(4-methylthiazol-5-yl)ethyl)spiro[isoindoline-1,3'-pyrrolidine]-2',3-dione;

(S)-2-((5-Amino-6-fluoro-1H-pyrrolo[3,2-b]pyridin-2-yl)methyl)-5-fluoro-1'-((R*)-1-(1-methylcyclopropyl)ethyl)spiro[isoindoline-1,3'-pyrrolidine]-2',3-dione;

(S)-2-((5-Amino-6-fluoro-1H-pyrrolo[3,2-b]pyridin-2-yl)methyl)-1'-(3-cyclopropylprop-2-yn-1-yl)-5-fluorospiro[isoindoline-1,3'-pyrrolidine]-2',3-dione;

(S)-2-((5-Amino-6-fluoro-1H-pyrrolo[3,2-b]pyridin-2-yl)methyl)-4-chloro-1'-(4-fluorobenzyl)spiro[isoindoline-1,3'-pyrrolidine]-2',3-dione;

(S)-2'-((5-Amino-6-fluoro-1H-pyrrolo[3,2-b]pyridin-2-yl)methyl)-1-(4-fluorobenzyl)spiro[pyrrolidine-3,1'-pyrrolo[3,4-c]pyridine]-2,3'(2'H)-dione;

(S)-2-((5-Amino-6-fluoro-1H-pyrrolo[3,2-b]pyridin-2-yl)methyl)-5-fluoro-1',7-dimethylspiro[isoindoline-1,3'-pyrrolidine]-2',3-dione;

(S)-2-((5-Amino-6-fluoro-1H-pyrrolo[3,2-b]pyridin-2-yl)methyl)-5-fluoro-7-methoxy-1'-methylspiro[isoindoline-1,3'-pyrrolidine]-2',3-dione;

(S)-2'-((5-Amino-6-fluoro-1H-pyrrolo[3,2-b]pyridin-2-yl)methyl)-1-(4-fluorobenzyl)spiro[pyrrolidine-3,3'-pyrrolo[3,4-c]pyridine]-1',2(2'H)-dione;

(S)-5-Amino-2-((5-fluoro-1'-((1-methylcyclopropyl)methyl)-2',3-dioxospiro[isoindoline-1,3'-pyrrolidin]-2-yl)methyl)-1H-pyrrolo[3,2-b]pyridine-7-carbonitrile;

(S)-2-((5-Amino-6-chloro-1H-pyrrolo[3,2-b]pyridin-2-yl)methyl)-5-fluoro-1'-(2-(trifluoromethoxy)ethyl)spiro[isoindoline-1,3'-pyrrolidine]-2',3-dione;

(S)-2-((6-Amino-4-methyl-1H-pyrrolo[2,3-b]pyridin-2-yl)methyl)-5-fluoro-1'-(2,4,5-trifluorobenzyl)spiro[isoindoline-1,3'-pyrrolidine]-2',3-dione; and (1S,5'S)-2-((5-Amino-6-fluoro-1H-pyrrolo[3,2-b]pyridin-2-yl)methyl)-5-fluoro-1',5'-dimethylspiro[isoindoline-1,3'-pyrrolidine]-2',3-dione;

or a pharmaceutically acceptable salt thereof.

In embodiments of the present specification there is provided a pharmaceutical composition which comprises a compound of the Formula (I) or a pharmaceutically acceptable salt thereof, in association with a pharmaceutically acceptable excipient, optionally further comprising one or more of the other stereoisomeric forms of the compound of Formula (I) or pharmaceutically acceptable salt thereof, wherein the compound of Formula (I) or pharmaceutically acceptable salt thereof is present within the composition with an enantiomeric excess (% ee) of 90%, for example >95% or >99%.

The compounds of Formula (I) and pharmaceutically acceptable salts thereof may be prepared, used or supplied in amorphous form, crystalline form, or semi-crystalline form and any given compound of Formula (I) or pharmaceutically acceptable salt thereof may be capable of being formed into more than one crystalline/polymorphic form, including hydrated (e.g. hemi-hydrate, a mono-hydrate, a di-hydrate, a tri-hydrate or other stoichiometry of hydrate) and/or solvated forms. It is to be understood that the present specification encompasses any and all such solid forms of the compound of Formula (I) and pharmaceutically acceptable salts thereof.

In further embodiments of the present specification there is provided a compound of Formula (I), which is obtainable by the methods described in the 'Examples' section hereinafter.

The present specification is intended to include all isotopes of atoms occurring in the present compounds. Isotopes will be understood to include those atoms having the same atomic number but different mass numbers. For example, isotopes of hydrogen include tritium and deuterium. Isotopes of carbon include $^{13}C$ and $^{14}C$. Isotopically labelled compounds of Formula (I) can generally be prepared by conventional techniques known to those skilled in the art or by processes analogous to those described in the accompanying Examples using appropriate isotopically labelled reagents in place of the non-labelled reagents previously employed.

A suitable pharmaceutically acceptable salt of a compound of the Formula (I) may be, for example, an acid addition salt. A suitable pharmaceutically acceptable salt of a compound of the Formula (I) may be, for example, an acid-addition salt of a compound of the Formula (I), for example an acid-addition salt with an inorganic or organic acid. The compounds of the specification may be provided as the free compound, i.e. in the non-salified state.

A further suitable pharmaceutically acceptable salt of a compound of the Formula (I) may be, for example, a salt formed within the human or animal body after administration of a compound of the Formula (I) to said human or animal body.

The compound of Formula (I) or pharmaceutically acceptable salt thereof may be prepared as a co-crystal solid form. It is to be understood that a pharmaceutically acceptable co-crystal of a compound of the Formula (I) or pharmaceutically acceptable salts thereof, form an aspect of the present specification.

For use in a pharmaceutical context it may be preferable to provide a compound of Formula (I) or a pharmaceutically acceptable salt thereof without large amounts of the other stereoisomeric forms being present.

The compound of Formula (I), or a pharmaceutically acceptable salt thereof, will normally be administered via the oral route though parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable salt or solvate thereof, or a solvate of such a salt, in a pharmaceutically acceptable dosage form may be possible. Depending upon the disorder and patient to be treated and the route of administration, the compositions may be administered at varying doses, for example in an oral dose of from 1 mg to 1,000 mg or from 100 mg to 2,000 mg.

The pharmaceutical formulations of the compound of Formula (I) described above may be prepared e.g. for parenteral, subcutaneous, intramuscular or intravenous administration.

The pharmaceutical formulations of the compound of Formula (I) described above may conveniently be administered in unit dosage form and may be prepared by any of the methods well-known in the pharmaceutical art, for example as described in Remington's Pharmaceutical Sciences, 17th ed., Mack Publishing Company, Easton, PA., (1985).

Pharmaceutical formulations suitable for oral administration may comprise one or more physiologically compatible carriers and/or excipients and may be in solid or liquid form. Tablets and capsules may be prepared with binding agents; fillers; lubricants; and surfactants. Liquid compositions may contain conventional additives such as suspending agents; emulsifying agents; and preservatives. Liquid compositions may be encapsulated in, for example, gelatin to provide a unit dosage form. Solid oral dosage forms include tablets, two-piece hard shell capsules and soft elastic gelatin (SEG) capsules. An exemplary oral composition would comprise a compound of Formula (I) and at least one pharmaceutically acceptable excipient filled into a two-piece hard shell capsule or a soft elastic gelatin (SEG) capsule.

According to a further embodiment there is provided a compound of the Formula (I), or a pharmaceutically acceptable salt thereof, as defined hereinbefore, for use as a medicament in a warm-blooded animal such as man.

According to a further embodiment, there is provided a compound of the Formula (I), or a pharmaceutically acceptable salt thereof, as defined hereinbefore for use in the production of an anti-proliferative effect in a warm-blooded animal such as man.

According to a further embodiment, there is provided a compound of the Formula (I), or a pharmaceutically acceptable salt thereof, as defined hereinbefore for use in a warm-blooded animal such as man as an anti-invasive agent in the containment and/or treatment of solid tumour disease, for example solid tumour disease in which the tumour in which the MTAP gene is deleted.

According to a further embodiment, there is provided the use of a compound of the Formula (I), or a pharmaceutically acceptable salt thereof, as defined hereinbefore, for the production of an anti-proliferative effect in a warm-blooded animal such as man that has a CDKN2A/MTAP deleted tumour.

According to a further embodiment, there is provided the use of a compound of the Formula (I), or a pharmaceutically acceptable salt thereof, as defined hereinbefore, in the manufacture of a medicament for use in the production of an anti-proliferative effect in a warm-blooded animal such as man, for example a medicine for the treatment of CDKN2A/MTAP deleted tumours.

According to a further embodiment, there is provided the use of a compound of the Formula (I), or a pharmaceutically acceptable salt thereof, as defined hereinbefore, in the manufacture of a medicament for use in a warm-blooded animal such as man as an anti-invasive agent in the containment and/or treatment of solid tumour disease, optionally wherein the solid tumour disease is characterised by having a MTAP gene deletion.

According to a further embodiment, there is provided a method for producing an anti-proliferative effect in a warm-blooded animal, such as man, in need of such treatment which comprises administering to said animal an effective amount of a compound of the Formula (I), or a pharmaceutically acceptable salt thereof, as defined hereinbefore. In such embodiments the patient in need of treatment may have a cancer that is characterised by being a MTAP deleted cancer, i.e. a cancer in which the MTAP gene has been deleted.

In this specification, unless otherwise stated, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician. The effective amount will generally be in the range of 0.1 mg to 1,000 mg.

According to a further embodiment, there is provided a method for producing an anti-invasive effect by the containment and/or treatment of solid tumour disease in a warm-blooded animal, such as man, in need of such treatment which comprises administering to said animal an effective amount of a compound of the Formula (I), or a pharmaceutically acceptable salt thereof, as defined hereinbefore. In such embodiments the patient in need of treatment may have a cancer that is characterised by being a MTAP deleted cancer, i.e. a cancer in which the MTAP gene has been deleted.

According to a further embodiment, there is provided a compound of the Formula (I), or a pharmaceutically acceptable salt thereof, as defined hereinbefore, for use in the prevention or treatment of cancer in a warm-blooded animal such as man. In such embodiments the cancer may be characterised by its MTAP deleted status, i.e. the cancer is one in which the MTAP gene has been deleted.

According to a further embodiment, there is provided the use of a compound of the Formula (I), or a pharmaceutically acceptable salt thereof, as defined hereinbefore in the manufacture of a medicament for use in the prevention or treatment of cancer in a warm-blooded animal such as man. In such embodiments the cancer may be characterised by its MTAP deleted status, i.e. the cancer is one in which the MTAP gene has been deleted.

According to a further embodiment, there is provided a method for the prevention or treatment of cancer in a warm-blooded animal, such as man, in need of such treatment which comprises administering to said animal an effective amount of a compound of the Formula (I), or a pharmaceutically acceptable salt thereof, as defined hereinbefore. In such embodiments the patient in need of treatment may have a cancer that is characterised by being a MTAP deleted cancer, i.e. a cancer in which the MTAP gene has been deleted.

According to a further embodiment, there is provided a compound of the Formula (I), or a pharmaceutically acceptable salt thereof, as defined hereinbefore for use in the prevention or treatment of solid tumour disease in a warm-blooded animal such as man. In such embodiments the solid tumour disease may be a MTAP gene deleted tumour.

According to a further embodiment, there is provided the use of a compound of the Formula (I), or a pharmaceutically acceptable salt thereof, as defined hereinbefore, in the manufacture of a medicament for use in the prevention or treatment of solid tumour disease in a warm-blooded animal such as man.

According to a further embodiment, there is provided a method for the prevention or treatment of solid tumour disease in a warm-blooded animal, such as man, in need of such treatment which comprises administering to said animal an effective amount of a compound of the Formula (I), or a pharmaceutically acceptable salt thereof, as defined hereinbefore. In such embodiments the patient in need of treatment may have a cancer that is characterised by being a MTAP deleted cancer, i.e. a cancer in which the MTAP gene has been deleted.

According to a further embodiment, there is provided a compound of the Formula (I), or a pharmaceutically acceptable salt thereof, as defined hereinbefore, for use in the prevention or treatment of tumours which are sensitive to inhibition of PRMT5. In such embodiments the tumour may be characterised by having a MTAP gene deletion.

According to a further embodiment, there is provided the use of a compound of the Formula (I), or a pharmaceutically acceptable salt thereof, as defined hereinbefore, in the manufacture of a medicament for use in the prevention or treatment of those tumours which are sensitive to inhibition of PRMT5. In such embodiments the tumour may be characterised by having a MTAP gene deletion.

According to a further embodiment, there is provided a method for the prevention or treatment of those tumours which are sensitive to inhibition of PRMT5, which comprises administering to a patient in need thereof an effective amount of a compound of the Formula (I), or a pharmaceutically acceptable salt thereof, as defined hereinbefore. In such embodiments the tumour may be characterised by having a MTAP gene deletion.

According to a further embodiment, there is provided a compound of the Formula (I), or a pharmaceutically acceptable salt thereof, as defined hereinbefore for use in providing an inhibitory effect on PRMT5. In such embodiments the inhibitory effect may be MTA-synergistic.

According to a further embodiment, there is provided the use of a compound of the Formula (I), or a pharmaceutically acceptable salt thereof, as defined hereinbefore in the manufacture of a medicament for use in providing an inhibitory effect on PRMT5.

According to a further embodiment, there is also provided a method for providing an inhibitory effect on PRMT5 which comprises administering an effective amount of a compound of the Formula (I), or a pharmaceutically acceptable salt thereof, as defined hereinbefore, to a patient in need thereof.

According to a further embodiment, there is provided a compound of the Formula (I), or a pharmaceutically acceptable salt thereof, as defined hereinbefore, for use in providing a selective inhibitory effect on PRMT5.

According to a further embodiment, there is provided the use of a compound of the Formula (I), or a pharmaceutically acceptable salt thereof, as defined hereinbefore, in the manufacture of a medicament for use in providing a selective inhibitory effect on PRMT5.

According to a further embodiment, there is also provided a method for providing a selective inhibitory effect on PRMT5 which comprises administering an effective amount of a compound of the Formula (I), or a pharmaceutically acceptable salt thereof, to a patient in need thereof.

Described herein are compounds that can bind to PRMT5. In biochemical and cell based assays the compounds of the present specification are shown to be potent PRMT5 protein binders and may therefore be useful in the treatment of disorders mediated by PRMT5, in particular in the treatment of cancers in which MTAP is deleted, such as pancreatic, colorectal, uterine, bile duct, stomach, bladder, cervical, testicular germ cell and non-small cell lung cancer and multiple myeloma, diffuse large B cell lymphoma, rhabdomyosarcoma and cutaneous squamous cell carcinoma. In preferred embodiments, the use will be for the treatment of a lung (e.g. NSCLC) and gastric cancer or lymphoma (e.g. DLBCL).

According to a further embodiment, there is provided a compound of the Formula (I), or a pharmaceutically acceptable salt thereof, as defined hereinbefore, for use in the treatment of disorders mediated by PRMT5.

According to a further embodiment, there is provided a method for treating disorders mediated by PRMT5, which comprises administering an effective amount of a compound of the Formula (I), or a pharmaceutically acceptable salt thereof, as defined hereinbefore.

According to a further embodiment, there is provided the use of a compound of the Formula (I), or a pharmaceutically acceptable salt thereof, as defined hereinbefore, in the manufacture of a medicament for use in the treatment of disorders mediated by PRMT5.

According to a further embodiment, there is provided a compound of the Formula (I), or a pharmaceutically acceptable salt thereof, as defined hereinbefore, for use in the treatment of gastric cancer, lung cancer or lymphoma.

According to a further embodiment, there is provided a compound of the Formula (I), or a pharmaceutically acceptable salt thereof, as defined hereinbefore, for use in the treatment of non-small cell lung cancer.

According to a further embodiment, there is provided a method for treating gastric cancer, non-small cell lung cancer or lymphoma cancer, which comprises administering an effective amount of a compound of the Formula (I), or a pharmaceutically acceptable salt thereof, as defined hereinbefore to a patient in need thereof.

According to a further embodiment, there is provided a method for treating non-small cell lung cancer, which comprises administering an effective amount of a compound of the Formula (I), or a pharmaceutically acceptable salt thereof, to a patient in need thereof.

According to a further embodiment, there is provided the use of a compound of the Formula (I), or a pharmaceutically acceptable salt thereof, as defined hereinbefore, in the manufacture of a medicament for use in the treatment of gastric cancer, non-small cell lung cancer or lymphoma cancer According to a further aspect of the specification, there is provided the use of a compound of the Formula (I), or a pharmaceutically acceptable salt thereof, as defined hereinbefore, in the manufacture of a medicament for use in the treatment of non-small cell lung cancer.

The anti-cancer treatment defined herein may be applied as a sole therapy or may involve, in addition to the compounds of the specification, conventional surgery or radiotherapy or chemotherapy.

Accordingly, in one embodiment, there is provided a compound of Formula (I), or a pharmaceutically acceptable salt thereof, and an additional anti-tumour substance for the conjoint treatment of cancer.

According to an embodiment of the specification there is provided a combination suitable for use in the treatment of cancer comprising a compound of the Formula (I) or a pharmaceutically acceptable salt thereof and another anti-tumour agent.

In a further embodiment of the specification there is provided a compound of the Formula (I), or a pharmaceutically acceptable salt thereof, in combination with another anti-tumour agent. In a related embodiment there is provided a method of treatment comprising administering a compound of Formula (I) in combination with another anti-tumour agent to a patient in need thereof, for example a patient suffering from a cancer in which the MTAP gene is deleted.

Although the compounds of the Formula (I) are primarily of value as therapeutic agents for use in warm-blooded animals (including man), they are also useful whenever it is required to inhibit PRMT5. Thus, they are useful as pharmacological standards for use in the development of new biological tests and in the search for new pharmacological agents.

Another embodiment is based on identifying a link between the MTAP gene deletion status of tumour in a patient and potential susceptibility to treatment with a compound of Formula (I). A MAT synergistic PRMT5 inhibitor, such as a compound of Formula (I), may then advantageously be used to treat patients with tumours in which the MTAP gene is deleted who may be resistant to other therapies. This therefore provides opportunities, methods and tools for selecting patients for treatment with a compound of Formula (I), particularly cancer patients. The selection is based on whether the tumour cells to be treated possess MTAP gene deletion. The MTAP gene deletion status could therefore be used as a biomarker to indicate that selecting treatment with a compound of Formula (I) may be advantageous.

According to one embodiment, there is provided a method for selecting a patient for treatment with a compound of Formula (I), the method comprising providing a tumour cell-containing sample from a patient; determining whether the MTAP gene in the patient's tumour cell-containing sample has been deleted; and selecting a patient for treatment with a compound of Formula (I) based thereon.

The method may include or exclude the actual patient sample isolation step. Thus, according to one embodiment there is provided a method for selecting a patient for treatment with a compound of Formula (I), the method comprising determining whether the MTAP gene in a tumour cell-containing sample previously isolated from the patient has been deleted; and selecting a patient for treatment with a compound of Formula (I) based thereon.

In embodiments, the patient is selected for treatment with a compound of Formula (I) if the tumour cell has the MTAP gene deleted.

According to another embodiment, there is provided a compound of Formula (I), or a pharmaceutically acceptable salt thereof, for use in treating cancers with tumour cells having the MTAP gene deleted or having a propensity to accumulate MTA.

According to another embodiment, there is provided a compound of Formula (I), or a pharmaceutically acceptable salt thereof, for use in treating cancers with tumour cells identified as accumulating MTA.

According to another embodiment, there is provided a pharmaceutical composition comprising a compound of Formula (I) for use in the prevention and treatment of cancer with tumour cells identified as having the MTAP gene deleted.

It will be appreciated that the following examples are provided so that the nature of the invention may be fully understood. It will also be appreciated that the following examples are not intended to limit the scope of the description in any way.

EXAMPLES

Biological Assays

The following assays were used to measure the effects of the compounds of the present specification.

MTase-Glo™ PRMT5 Luminescence Assays (PRMT5 Enzyme Assays)

An Mtase-Glo™ methyltransferase Luminescence assay was employed to monitor the conversion of S-Adenosyl methionine (SAM) to S-Adenosyl Homocysteine (SAH) by recombinant PRMT5:MEP50 enzyme complex in the presence or absence of the 5'-Methylthioadenosine (MTA). The enzymatic reaction was performed in a white 1536-well microtiter plate (Greiner, #782075). The reaction buffer contained 20 mM Bicine (pH 7.60), 25 mM NaCl, 1 mM DTT and 0.1% (w/v) CHAPS.

For the inhibition assays, compounds of interests and reference controls in DMSO were dispensed into the microplates using a Labcyte Echo 555 acoustic dispenser following a twelve point duplicate half-log compound concentration—response with a top concentration of 100 μM. All wells were backfilled with the appropriate volume of DMSO to achieve a final concentration of 1% v/v in a 3 μl final assay volume. All assay ready plates included neutral controls (no inhibition, 1% v/v DMSO) and inhibitor controls (100% inhibition, 30 μM of assay-specific compound).

The inhibition assay without MTA was carried out by incubating the inhibitors with 3 μL reaction mixture containing 1 nM human heterooctameric PRMT5:MEP50 enzyme complexes, 2.5 μM H41-21 histone peptide (Cayman Chemical Co., #10854) and 2.5 μM S-Adenosyl Methionine (SAM) (Promega, A120A) in reaction buffer. Likewise, the assay in the presence of MTA was performed by incubating the inhibitors with 3 μL enzyme mixture consisting of 2 nM enzyme complex, 1.5 μM MTA (Sigma, D5011), 2.5 μM H41-21 peptide and 2.5 μM SAM. After 5 h incubation in room temperature, 1 μL of 0.5% (v/v) TFA was added to each well to quench the methylation reaction. One microliter of 5× concentrated MTase-Glo™ Reagent (Promega, CS175601A) was subsequently added to each well and incubated at room temperature to convert the SAH produced in the reaction to ADP. After 10 min, 2.5 μL of prefiltered Mtase-Glo™ detection solution (Promega, CS175601B) was added into each well and incubated at room temperature for a further 30 min to ensure the conversion of ADP to luminescence, which was measured using an Evision 2101 Multilabel Plate reader.

Data was analysed and the $IC_{50}$ values were calculated using the Genedata Screener® software.

PRMT5 Cell SDMA Assays:

HCT116 WT and KO-MTAP cells were cultured in cell media composed of McCoys media (Sigma #M8403), 10% (v/v) Foetal Calf Serum and 1% (v/v) L-Glutamine. After harvesting, cells were dispensed into black, 384-well Costar plates (#3712, Corning) to give 2000 cells per well in a total volume of 40 μl cell media. Test compounds and reference controls were dosed directly into the cell plates using a Labcyte Echo 555 acoustic dispenser following a twelve point half-log compound concentration—response with a top concentration of 30 μM The cell plates were then incubated for 48 hours at 37° C. before being fixed by the addition of 40 μl 8% paraformaldehyde in PBS/A (4% final concentration), followed by a 10 minute room temperature incubation, plates were then washed twice with 150 μl PBS using a BioTek ELx406 platewasher, permeabilised for 10 min with 20 ul/well 0.1%

Saponin in PBS, washed again and blocked with 20 ul/well 2% BSA in PBS-T (Sigma #A8022) for 1 hour at room temperature.

Primary anti-SDMA Histone 4 Antibody (Milipore #07-947) was diluted 1:1000 in PBS-T+0.05% BSA, 20 µl added per well, and plates were incubated at 4° C. overnight. Cell plates were washed 3× with 200 µl PBS/T, then 20 µl 1:500 dilution in assay buffer of Alexa Fluor® 488 goat anti-rabbit IgG secondary antibody (Thermo #A11008,), with a 1:1000 dilution of Hoechst 33342, was added per well. Following a 1 hour incubation at room temperature, plates were washed 3× with 200 µl PBS/T, and 40 µl PBS w/o Ca, Mg and Na Bicarb (Gibco #14190-094) was added per well.

Stained cell plates were covered with black seals, and then read on the Cell Insight imaging platform (Thermo Scientific), with a 10' objective. The primary channel (Hoechst blue fluorescence 405 nM, BGRFR_386_23) is used to Autofocus and to count number of events (this will provide information about cytotoxicity of the compounds tested). The secondary channel (Green 488 nM, BGRFR_485_20) measures SDMA staining.

Data was analysed and $IC_{50}$s were calculated using Genedata Screener® software. The assay window is determined in Genedata by quantification of max signal/Top (vehicle control) and min signal/bottom (30 µM of a known standard strong inhibitor compound) and $IC_{50}$s are calculated using the hill model.

$$Y = \text{Bottom} + \frac{\text{Top} - \text{Bottom}}{1 + 10^{(Log\ IC_{50} - Log\ Conc.)*nH}}$$

Cell Proliferation Assays:

HCT116 WT and KO-MTAP cells were cultured in cell media composed of McCoys media (Sigma #M8403), 10% (v/v) Foetal Calf Serum and 1% (v/v) L-Glutamine. After harvesting, cells were dispensed into black, 384-well Costar plates (#3712, Corning) to give 400 cells per well in a total volume of 40 µl cell media. Test compounds and reference controls were dosed directly into the cell plates using a Labcyte Echo 555 acoustic dispenser following a twelve point duplicate half-log compound concentration—response with a top concentration of 30 µM.

A day 0 plate is created in parallel but not dosed, after plating 4 µl of Alamar Blue (Thermo #DAL1100) and incubate for 3 h at 37 C, 5% $CO_2$. Following incubation plates are read using an EnVision plate reader with fluorescence excitation wavelength of 540-570 nm (peak excitation is 570 nm), fluorescence emission at 580-610 nm (peak emission is 585 nm).

The dosed cell plates were then incubated for 5 days at 37° C. before adding Alamar blue and being read in the Envision following same protocol as for first plate. Data was analysed and IG50's were calculated using Genedata Screener® software by normalizing to plate 0.

Data obtained in the foregoing assay are presented in Table 2 below.

TABLE 2

Activity of Examples 1 to 29 in inhibiting PRMT5 protein, in MTAP wild type (WT) and knock out (KO) cells and cell proliferation in MTAP wild type (WT) and knock out (KO) cells

| Example | PRMT5 enzyme $IC_{50}$ (µM) (+MTA version) | PRMT5 enzyme $IC_{50}$ (µM) (no MTA version) | Cell SDMA $IC_{50}$ (µM) (MTAP KO) | Cell SDMA $IC_{50}$ (µM) (MTAP WT) | Cell proliferation $IC_{50}$ (µM) (MTAP KO) | Cell proliferation $IC_{50}$ (µM) (MTAP WT) |
|---|---|---|---|---|---|---|
| 1 | 0.0038 | 0.025 | 0.0053 | 0.29 | 0.16 | >30 |
| 2 | 0.006 | 0.027 | 0.0059 | 0.2 | 0.24 | 6.1 |
| 3 | 0.0085 | 0.061 | 0.013 | 0.56 | 0.32 | >30 |
| 4 | 0.0077 | 0.038 | 0.0094 | 0.19 | | |
| 5 | 0.0041 | 0.04 | 0.0057 | 0.17 | | |
| 6 | 0.0046 | 0.025 | 0.0017 | 0.054 | | |
| 7 | 0.0081 | 0.03 | 0.0017 | 0.036 | | |
| 8 | 0.0064 | 0.063 | 0.025 | >1.5 | 1.9 | >30 |
| 9 | 0.017 | 0.14 | 0.015 | 0.53 | | |
| 10 | 0.0092 | 0.091 | 0.023 | 1.7 | 1.6 | >30 |
| 11 | 0.012 | 0.09 | 0.02 | 0.81 | | |
| 12 | 0.0085 | 0.065 | 0.0088 | 0.43 | | |
| 13 | 0.009 | 0.05 | 0.0084 | 0.34 | | |
| 14 | 0.022 | 0.14 | 0.006 | 0.088 | | |
| 15 | 0.0082 | 0.016 | 0.0036 | 0.12 | | |
| 16 | 0.0039 | 0.023 | 0.0051 | 0.23 | | |
| 17 | 0.015 | 0.15 | 0.0068 | 0.42 | | |
| 18 | 0.0043 | 0.049 | 0.0066 | 0.37 | | |
| 19 | 0.0086 | 0.21 | 0.032 | 0.86 | | |
| 20 | 0.063 | 0.034 | 0.0029 | 0.16 | | |
| 21 | 0.0095 | 0.14 | 0.086 | 3.2 | | |
| 22 | 0.0069 | 0.061 | 0.011 | 0.51 | | |
| 23 | 0.026 | 0.26 | 0.16 | 12 | | |
| 24 | 0.0065 | 0.055 | 0.032 | 1.2 | | |
| 25 | 0.0087 | 0.09 | 0.014 | 0.44 | | |
| 26 | 0.011 | 0.021 | 0.0031 | 0.093 | 0.29 | 2.3 |
| 27 | 0.012 | 0.044 | 0.0047 | 0.17 | 0.36 | >30 |
| 28 | 0.0071 | 0.015 | 0.0028 | 0.071 | 0.13 | 1.4 |
| 29 | 0.0067 | 0.083 | 0.018 | 0.81 | | |

As can be seen from the results presented in Table 2, the Examples according to the specification are all "MTA-synergistic" PRMT5 inhibitors and this activity profile provides for an enhanced anti-proliferative activity in MTAP deleted cells. In more detail, inspection of columns 2 and 3 reveals that the concentrations of PRMT5 inhibitor required to cause 50% inhibition of isolated protein (i.e. PRMT5 enzyme) is greatly reduced when MTA is present in the assay system with $IC_{50}$'s in the presence of MTA observed in the single digit or tens of nM range when MTA is present (column 2), compared with tens to hundreds of nM range when MTA is not present (column 3). The data for Examples 1, 2 & 3 clearly illustrates this enhanced activity in the presence of MTA with respective $IC_{50}$'s of 3.8, 6.0 and 8.5 nM, respectively, being observed in the presence of MTA, whereas their activity in the absence of MTA is 25, 27 and 61 nM.

The same, arguably more pronounced, "MTA-synergistic" inhibitory effect is observed in the HCT116 cellular assay as can be readily seen from inspection of columns 4 and 5 of Table 2. Comparing results for Examples 1, 2 & 3 once more ($IC_{50}$'s of 5.3, 5.9 and 13 nM vs $IC_{50}$'s of 290, 200 and 560 nM in columns 4 and 5 respectively), the activity of the PRMT5 inhibitors according to the specification is far greater in MTAP knock out HCT116 cells that, due to their lack of MTAP, accumulate MTA. In contrast, in the HCT116 wild type cells (column 5) the PRMT5 inhibition is greatly reduced and more modest $IC_{50}$ values are observed. Finally, the translation of PRMT5 inhibitory activity into an anti-proliferative effect of MTAP knock out and wild type HCT116 human cancer cells in vitro is confirmed by the data presented in columns 6 and 7. As would be expected from their "MTA-synergistic" PRMT5 inhibitory activity, the PRMT5 inhibitors according to the specification exert a far greater anti-proliferative effect in MTAP deficient cells (column 6) than in MTAP wild type cells, with $IC_{50}$'s for Examples 1, 2 & 3 (160, 240 and 320 nM) in MTAP KO cells in the hundreds of nanomolar range compared to $IC_{50}$'s (>30, 6.1 and >30 μM) well into the micromolar range in MTAP WT cells. It can be readily appreciated that the PRMT5 inhibitors according to the specification possess an activity profile that render them promising candidates for the treatment of the ca 15% of solid tumour that carry the MTAP gene deletion, and that as a results accumulate MTA.

EXAMPLES

The compounds described in this specification are further illustrated in the following Examples. The compounds were named using Chemdraw version 20.0.2.51. These Examples are given by way of illustration only and are non-limiting. In general:

(i) operations were carried out at ambient temperature, i.e. in the range 17 to 25° C. and under an atmosphere of an inert gas such as nitrogen unless otherwise stated;

(ii) evaporations were carried out by rotary evaporation or utilising Genevac equipment or Biotage v10 evaporator in vacuo and work up procedures were carried out after removal of residual solids by filtration;

(iii) flash chromatography purifications were performed on an automated Teledyne Isco CombiFlash® Rf or Teledyne Isco CombiFlash® Companion® using pre-packed RediSep Rf Gold™ Silica Columns (20-40 μm, spherical particles), GraceResolv™ Cartridges (Davisil® silica) or Silicycle cartridges (40-63 μm).

(iv) preparative reverse phase HPLC was performed on an Agilent 1290 Infinity II Preparative system equipped with a SQ MS detector (Multimode ESI/APCI source), with a Waters CSH C18 OBD column (5 microns silica, 30 mm diameter, 100 mm length, flow rate of 50 mL/min) using decreasingly polar mixtures of water (containing 0.1-0.3% aqueous ammonium) or water (containing 0.1% formic acid) and acetonitrile as eluents. Preparative SFC purification was performed on either a Sepiatec P100 SFC system or Waters Prep 100 SFC system equipped with QDa MS detector, using the chromatographic conditions as detailed in corresponding experimental data.

(v) yields, where present, are not necessarily the maximum attainable;

(vi) in general, the structures of end products of the Formula I were confirmed by nuclear magnetic resonance (NMR) spectroscopy; NMR chemical shift values were measured on the delta scale [proton magnetic resonance spectra were determined using a Bruker Avance 500 (500 MHz) or Bruker Avance 400 (400 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal (vii) in general, end products of the Formula I were also characterized by mass spectrometry following liquid chromatography (LCMS or UPLC); reverse-phase C18 silica was used with a flow rate of 1 mL/min and detection was by Electrospray Mass Spectrometry and by UV absorbance recording a wavelength range of 220-320 nm. Analytical UPLC was performed on CSH C18 reverse-phase silica, using a Waters Acquity UPLC CSH C18 column with dimensions 2.1×50 mm and particle size 1.7 micron) Gradient analysis was employed using decreasingly polar mixtures as eluent, for example decreasingly polar mixtures of water (containing 0.1% formic acid or 0.1% ammonia) as solvent A and acetonitrile as solvent B. A typical 2 minute analytical UPLC method would employ a solvent gradient over 1.3 min, at approximately 1 mL/min, from a 97:3 mixture of solvents A and B respectively to a 3:97 mixture of solvents A and B. The reported molecular ion corresponds to the [M+H]+ unless otherwise specified; for molecules with multiple isotopic patterns (Br, Cl etc.) the reported value is the one obtained for the lowest isotope mass unless otherwise specified.

(viii) ion exchange purification was generally performed using a SCX-2 (Biotage, Propylsulfonic acid functionalized silica. Manufactured using a trifunctional silane. Non end-capped) cartridge.

(ix) intermediate purity was assessed by thin layer chromatographic, mass spectral, HPLC (high performance liquid chromatography) and/or NMR analysis;

(x) Unless otherwise stated, molecular sieves used in preparations were 4 Å in size (xi) the following abbreviations have been used:
aq. Aqueous
Boc tert-butoxycarbonyl
Brettphos 2-(dicyclohexylphosphino)3,6-dimethoxy-2',4',6'-triisopropyl-1,1'-biphenyl
CataCXium® A di(1-adamantyl)-n-butylphosphine
Conc. concentrated
$CCl_4$ carbon tetrachloride
DCM dichloromethane
DIBAL diisobutylaluminium hydride
DIPEA/DIEA diisopropylethylamine DMAP dimethylaminopyridine
DMA N,N-dimethylacetamide
DMF N,N-dimethylformamide
DMSO dimethyl sulfoxide
EPhos dicyclohexyl(3-isopropoxy-2',4',6'-triisopropyl-[1,1'-biphenyl]-2-yl)phosphane
EtOAc ethyl acetate
h hour(s)
HATU 1-[bis(dimethylamino)methylene]-1H-1,2,3-triazolo[4,5-b]pyridinium 3-oxide hexafluorophosphate
HPLC high performance liquid chromatography
m-CPBA 3-chloroperbenzoic acid
MeCN acetonitrile
MeOH methanol
$MgSO_4$ magnesium sulfate
MTBE tert-butyl methyl ether
$NaHCO_3$ sodium hydrogen carbonate
$Na_2SO_4$ sodium sulfate
$NH_4Cl$ ammonium chloride
NBS N-bromosuccinimide
NIS N-iodosuccinimide
rac-BINAP (±)-2,2'-bis(diphenylphosphino)-1,1'-binaphthalene
rt/RT room temperature
RockPhos $3^{rd}$ generation precatalyst [(2-di-tert-butylphosphino-3-methoxy-6-methyl-2',4',6'-triisopropyl-1,1'-biphenyl)-2-(2-aminobiphenyl)]palladium(II) methanesulfonate
Ruphos 2-dicyclohexylphosphino-2',6'-diisopropoxy-1,1'-biphenyl
sat. saturated
SEM trimethylsilylethoxymethyl
SFC supercritical fluid chromatography
sol. Solution
SPhos 2-dicyclohexylphosphino-2',6'-dimethoxybiphenyl
TBAF tetra-n-butylammonium fluoride
TEA triethylamine
TES triethylsilane
TFA trifluoroacetic acid
TFAA trifluoroacetic anhydride
THF tetrahydrofuran
THP tetrahydropyran
Tr trityl
Xantphos 4,5-bis(diphenylphosphino)-9,9-dimethylxanthene Intermediate AA: Methyl 2-(2-bromo-4-fluorophenyl)acetate

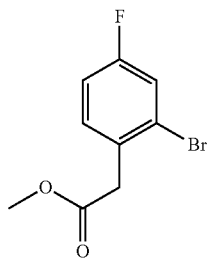

Thionyl chloride (31.3 mL, 429.1 mmol) was added dropwise carefully to 2-(2-bromo-4-fluorophenyl)acetic acid (CAS No. 61150-59-2) (100 g, 429.1 mmol) in MeOH (400 mL) at rt. The reaction mixture was stirred at 60° C. for 4 hours, cooled and the solvent was removed in vacuo. The residue was partitioned between EtOAc (250 mL) and saturated $NaHCO_3$ (200 mL). The organic phase was washed with water (100 mL), brine (100 mL), passed through a phase separating filter paper and the solvent was removed in vacuo to afford the title compound (105 g, 99%) as a colourless oil.

$^1$H NMR (400 MHz, DMSO-d6, 30° C.) 3.64 (3H, s), 3.83 (2H, s), 7.25 (1H, td), 7.48 (1H, dd), 7.58 (1H, dd)); m/z MH$^+$ not observed.

Intermediate AB: Methyl 5-fluoro-2-(2-methoxy-2-oxoethyl)benzoate

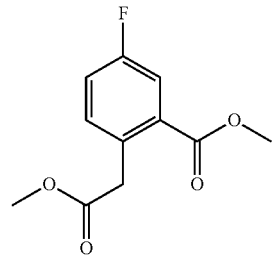

Methyl 2-(2-bromo-4-fluorophenyl)acetate (45.0 g, 182.14 mmol) and triethylamine (27.90 mL, 200.35 mmol) were placed in a steel pressure vessel with MeOH (300 mL). [1,1'-Bis(diphenylphosphino)ferrocene]dichloropalladium (II) (complex with dichloromethane) (4.46 g, 5.46 mmol) was added and the vessel was sealed. The vessel was purged with carbon monoxide and then charged to 7 bar with carbon monoxide. The pressure vessel was heated to 100° C. and stirred for 2 hours. The reaction mixture was allowed to cool, vented and filtered to remove catalyst. The solvent was removed in vacuo and the residue was dissolved in EtOAc (250 mL), washed with water (2×200 mL) and brine (100 mL). The organic phase was passed through a phase separating filter paper and the solvent was removed in vacuo. The crude product was purified by flash silica chromatography, elution gradient 0 to 50% EtOAc in heptane. Pure fractions were evaporated to dryness to afford the title compound (38.40 g, 93%) as a pale yellow oil.

$^1$H NMR (400 MHz, DMSO-d6, 30° C.) 3.60 (3H, s), 3.80 (3H, s), 3.99 (2H, s), 7.42-7.49 (2H, m), 7.66 (1H, ddd); m/z MH$^+$ 227.

Intermediate AC: rac-Methyl-2-(1-bromo-2-methoxy-2-oxoethyl)-5-fluorobenzoate

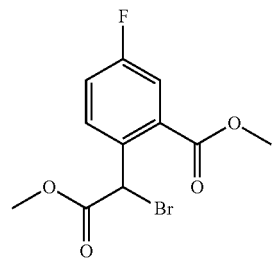

Methyl 5-fluoro-2-(2-methoxy-2-oxoethyl)benzoate (47.0 g, 207.8 mmol) was dissolved in chloroform (450 mL). 1-Bromopyrrolidine-2,5-dione (55.5 g, 311 mmol) was added followed by 2,2'-azobis(2-methylpropionitrile) (3.41 g, 20.8 mmol) and the reaction mixture was stirred at reflux for 72 hours. The reaction mixture was cooled and washed with water (2×250 mL), brine (100 mL), passed through a phase separating filter paper and the solvent was removed in vacuo. The crude product was purified by flash silica chromatography, elution gradient 0 to 40% EtOAc in heptane. Pure fractions were evaporated to dryness to afford the title compound (50.50 g, 80%) as a colourless oil.

$^1$H NMR (400 MHz, DMSO-d6, 30° C.) 3.71 (3H, s), 3.86 (3H, s), 6.51 (1H, s), 7.56 (1H, td), 7.66 (1H, dd), 7.81 (1H, dd); m/z MH$^+$ not observed.

Intermediate AD: rac-Methyl 5-fluoro-2-(4-methoxybenzyl)-3-oxoisoindoline-1-carboxylate

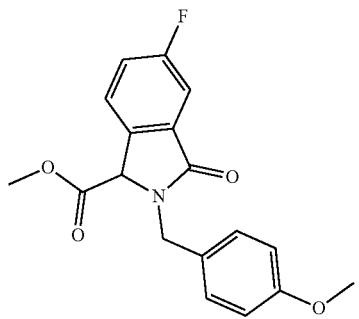

4-Methoxybenzylamine (23.5 g, 171 mmol) was placed in a flask with MeCN (300 mL) and sodium bicarbonate (23.9 g, 285 mmol) was added. rac-Methyl 2-(1-bromo-2-methoxy-2-oxoethyl)-5-fluorobenzoate (43.5 g, 142 mmol), dissolved in MeCN (100 mL), was added slowly via dropping funnel as the reaction mixture was brought up to 80° C. The reaction mixture was stirred at 80° C. for 3 hours. The reaction mixture was allowed to cool, most of the MeCN was removed in vacuo and the residue was partitioned between EtOAc (400 mL) and water (400 mL). The aqueous phase was re-extracted with EtOAc (100 mL), the organics were combined and washed with brine (50 mL). The organic phase was passed through a phase separating filter paper and the solvent was removed in vacuo. The crude product was purified by flash silica chromatography, elution gradient 0 to 50% EtOAc in heptane. Pure fractions were evaporated to dryness to afford the title compound (45.3 g, 96%) as a pale yellow oil.

$^1$H NMR (400 MHz, DMSO-d6, 30° C.) 3.69 (3H, s), 3.73 (3H, s), 4.31 (1H, d), 5.04 (1H, d), 5.18 (1H, s), 6.87-6.94 (2H, m), 7.17-7.24 (2H, m), 7.50 (1H, ddd), 7.57 (1H, dd), 7.62 (1H, dd); m/z MH$^+$ 330.

Intermediate AE: rat-Methyl 1-allyl-5-fluoro-2-(4-methoxybenzyl)-3-oxoisoindoline-1-carboxylate

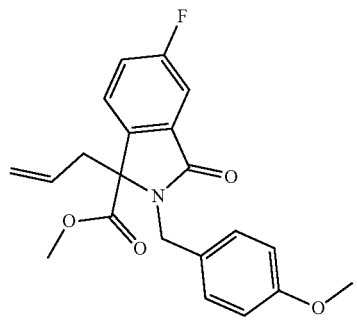 [SMILES: C=CCC1(C(=O)OC)c2ccc(F)cc2C(=O)N1Cc1ccc(OC)cc1]

rac-Methyl 5-fluoro-2-(4-methoxybenzyl)-3-oxoisoindoline-1-carboxylate (24.0 g, 72.9 mmol), allyl acetate (11.8 mL, 109 mmol), tris(dibenzylideneacetone)dipalladium(0) (1.67 g, 1.82 mmol) and N,N'-((1R,2R)-cyclohexane-1,2-diyl)bis(2-(diphenylphosphaneyl)benzamide) (2.52 g, 3.64 mmol) were stirred in THF (400 mL) at 5° C. under nitrogen. 1,1,3,3-tetramethylguanidine (13.7 mL, 109 mmol) was then added dropwise. The reaction mixture was stirred at 5° C. for 5 minutes. The THF was removed in vacuo. The reaction mixture was partitioned between EtOAc (400 mL) and water (400 mL) and the organic phase was passed through a phase separating filter paper. The solvent was removed in vacuo to afford an orange oil. The crude product was purified by flash silica chromatography, elution gradient 0 to 50% EtOAc in heptane. Pure fractions were evaporated to dryness to afford the title compound (25.8 g, 96%) as a cream solid.

$^1$H NMR (400 MHz, DMSO-d6, 30° C.) 3.04-3.20 (2H, m), 3.26 (3H, s), 3.73 (3H, s), 4.52 (1H, d), 4.71 (1H, d), 4.74-4.94 (3H, m), 6.82-6.96 (2H, m), 7.28-7.39 (2H, m), 7.45-7.58 (2H, m), 7.63 (1H, dd); m/z MH$^+$ 370.

Intermediate AF: Methyl (S)-1-allyl-5-fluoro-2-(4-methoxybenzyl)-3-oxoisoindoline-1-carboxylate

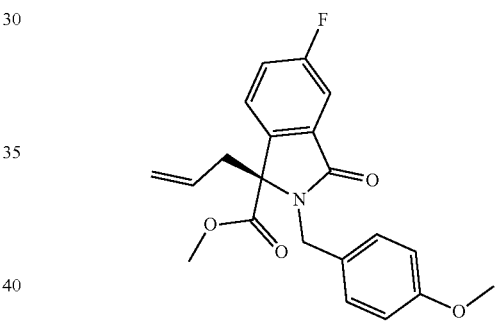

rac-Methyl 1-allyl-5-fluoro-2-(4-methoxybenzyl)-3-oxoisoindoline-1-carboxylate (~70:30 in favour of the desired (S) enantiomer) (25.8 g, 69.7 mmol) was purified by SFC chromatography (Column: Phenomenex C1, 30×250 mm, 5 micron, mobile phase: 10% IPA+0.1% DEA/90% scCO$_2$, flow rate: 90 ml/min, BPR: 120 bar, column temperature: 40° C., UV max 210 nm). Pure fractions were evaporated to dryness to afford the title compound (15.1 g, 56%) as a as a white solid.

$^1$H NMR (400 MHz, DMSO-d6, 30° C.) 3.04-3.20 (2H, m), 3.26 (3H, s), 3.73 (3H, s), 4.52 (1H, d), 4.71 (1H, d), 4.74-4.94 (3H, m), 6.82-6.96 (2H, m), 7.28-7.39 (2H, m), 7.45-7.58 (2H, m), 7.63 (1H, dd); m/z MH$^+$ 370

(Presumed stereochemical assignment of this intermediate based on biological activity of bioactive compounds made using this enantiomer of the intermediate (compared to those made using the other enantiomer), together with Xray structural evidence that the S enantiomer is preferred and more active than the R enantiomer).

Intermediate AG: Methyl (S)-5-fluoro-2-(4-methoxybenzyl)-3-oxo-1-(2-oxoethyl)isoindoline-1-carboxylate

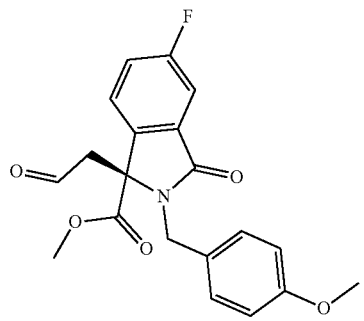 [SMILES: COC(=O)[C@]1(CC=O)c2ccc(F)cc2C(=O)N1Cc1ccc(OC)cc1]

To a solution of methyl (S)-1-allyl-5-fluoro-2-(4-methoxybenzyl)-3-oxoisoindoline-1-carboxylate (60.0 g, 162 mmol) in 1,4-dioxane (800 mL) and water (200 mL) was added osmium(VIII) oxide (4% in water) (5.16 mL, 0.81 mmol), sodium periodate (87.0 g, 406 mmol) and 2,6-dimethylpyridine (37.8 mL, 324 mmol). The reaction mixture was stirred at rt for 18 hours. The reaction mixture was filtered to remove salts and rinsed through with DCM (500 mL). The filtrate was placed in a separating funnel with water (500 mL) and partitioned. The aqueous phase was re-extracted with DCM (300 mL), the organic phases were combined, passed through a phase separating filter paper and the solvent was removed in vacuo. The crude product was purified by flash silica chromatography, elution gradient 0 to 50% EtOAc in heptane. Pure fractions were evaporated to dryness to afford the title compound (50.1 g, 83%) as a white crystalline solid.

$^1$H NMR (400 MHz, DMSO-d6, 30° C.) 3.40 (3H, s), 3.42-3.56 (2H, m), 3.72 (3H, s), 4.58 (1H, d), 4.74 (1H, d), 6.80-6.92 (2H, m), 7.19-7.27 (2H, m), 7.52 (1H, ddd), 7.60 (1H, dd), 7.69 (1H, dd), 9.07 (1H, t); m/z MH$^+$ 372.

Intermediate AH: rac-Methyl 5-fluoro-2-[(4-methoxyphenyl)methyl]-3-oxo-1-(2-oxoethyl)isoindoline-1-carboxylate

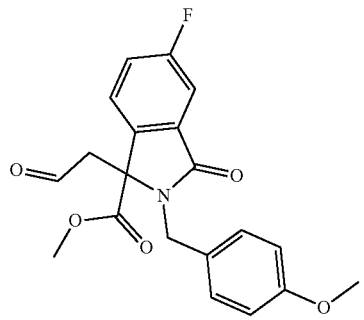 [SMILES: COC(=O)C1(CC=O)c2ccc(F)cc2C(=O)N1Cc1ccc(OC)cc1]

The title compound was prepared according to the method of Intermediate AG: Methyl (S)-5-fluoro-2-(4-methoxybenzyl)-3-oxo-1-(2-oxoethyl)isoindoline-1-carboxylate using Intermediate AE: rac-methyl (R)-1-allyl-5-fluoro-2-(4-methoxybenzyl)-3-oxoisoindoline-1-carboxylate.

$^1$H NMR (400 MHz, CDCl$_3$) 3.06-3.15 (1H, m), 3.19-3.29 (1H, m), 3.58 (3H, s), 3.78 (3H, s), 4.46 (1H, d), 5.11 (1H, d), 6.78-6.87 (2H, m), 7.18-7.25 (2H, m), 7.25-7.34 (1H, m), 7.44-7.52 (1H, m), 7.57-7.64 (1H, m), 9.06 (1H, t)

Intermediate AI: Methyl (S)-1-allyl-5-fluoro-3-oxoisoindoline-1-

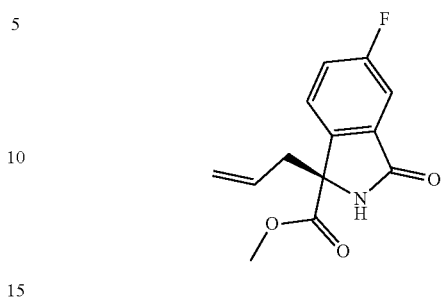

Methyl (S)-1-allyl-5-fluoro-2-(4-methoxybenzyl)-3-oxoisoindoline-1-carboxylate (20.0 g, 54.1 mmol) was placed in a flask with MeCN (200 mL) and water (100 mL). Ammonium cerium(IV) nitrate (74.2 g, 135 mmol) was added and the reaction mixture was stirred at rt for 30 minutes. The MeCN was removed in vacuo and the reaction mixture was partitioned between DCM (400 mL) and water (250 mL). The aqueous phase was extracted with DCM (200 mL). The organic phases were combined, washed with brine (100 mL), passed through a phase separating filter paper and the solvent was removed in vacuo. The crude product was purified by flash silica chromatography, elution gradient 0 to 50% EtOAc in heptane. Pure fractions were evaporated to dryness to afford the title compound (12.5 g, 93%) as a cream crystalline solid.

$^1$H NMR (400 MHz, DMSO-d6, 27° C.) 2.79 (1H, dd), 2.94 (1H, dd), 3.68 (3H, s), 4.93-5.15 (2H, m), 5.35-5.57 (1H, m), 7.37-7.46 (1H, m), 7.50 (1H, ddd), 7.63-7.79 (1H, m), 9.32 (1H, s); m/z MH$^+$ 250.

Intermediate AJ: Methyl 3-bromo-2-(bromomethyl)-5-fluorobenzoate

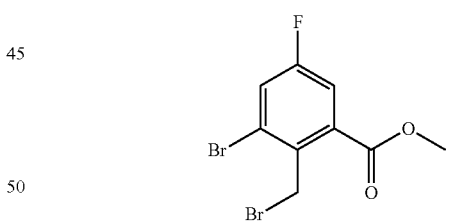

2,2'-Azobis(2-methylpropionitrile) (1.66 g, 10.1 mmol) was added in one portion to methyl 3-bromo-5-fluoro-2-methylbenzoate (CAS No. 1187318-53-1) (25.0 g, 101 mmol) and NBS (18.9 g, 106 mmol) in CCl$_4$ (400 mL) under nitrogen at rt. The reaction mixture was stirred at 90° C. for 16 hours. The reaction mixture was cooled and the solvent was removed in vacuo. The crude product was purified by flash silica chromatography, elution gradient 0 to 4% EtOAc in petroleum ether (60-90° C.). Pure fractions were evaporated to dryness to afford the title compound (28.0 g, 85%) as a colourless oil.

$^1$H NMR (400 MHz, CDCl$_3$, 30° C.) 3.98 (3H, s), 5.12 (2H, s), 7.51-7.58 (1H, m), 7.61-7.68 (1H, m); m/z MH$^+$ no mass ion.

Intermediate AK: Methyl 3-bromo-2-(cyanomethyl)-5-fluorobenzoate

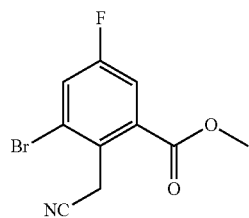

Trimethylsilyl cyanide (19.7 mL, 147 mmol) was added dropwise to methyl 3-bromo-2-(bromomethyl)-5-fluorobenzoate (24.0 g, 73.6 mmol) and potassium carbonate (20.4 g, 147 mmol) in MeCN (200 mL) at rt. The reaction mixture was stirred at 60° C. for 16 hours and then cooled to rt. The reaction mixture was poured into water (200 mL) and extracted with EtOAc (2×200 mL). The organic phase was dried over MgSO₄, filtered and the solvent was removed in vacuo. The crude product was purified by flash silica chromatography, elution gradient 0 to 20% EtOAc in petroleum ether (60-90 ° C.). Pure fractions were evaporated to dryness to afford the title compound (16.5 g, 82%) as a white solid.

$^1$H NMR (400 MHz, CDCl₃) 4.00 (3H, s), 4.36 (2H, s), 7.57-7.64 (1H, m), 7.72-7.79 (1H, m); m/z MH⁺ 272.

Intermediate AL: Methyl 3-bromo-5-fluoro-2-(2-methoxy-2-oxoethyl)benzoate

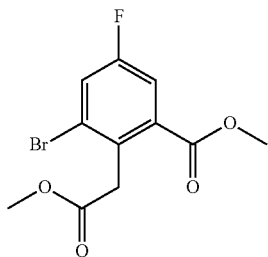

Concentrated sulfuric acid (3.33 mL, 62.5 mmol) was added dropwise to methyl 3-bromo-2-(cyanomethyl)-5-fluorobenzoate (17.0 g, 62.5 mmol) in MeOH (100 mL) at 0° C. The reaction mixture was stirred at 80° C. for 5 days, cooled and the solvent was removed in vacuo. The residue was poured into ice (200 mL), basified with ammonium hydroxide (28-30% in water) and extracted with EtOAc (3×150 mL). The organic phases were combined, dried over MgSO₄, filtered and the solvent was removed in vacuo. The crude product was purified by flash silica chromatography, elution gradient 0 to 30% EtOAc in petroleum ether (60-90° C.). Pure fractions were evaporated to dryness to afford the title compound (15.0 g, 79%) as a colourless oil.

$^1$H NMR (400 MHz, CDCl₃) 3.74 (3H, s), 3.91 (3H, s), 4.28 (2H, s), 7.52-7.59 (1H, m), 7.65-7.73 (1H, m); m/z MH⁺ 305.

Intermediate AM: rac-Methyl 7-bromo-5-fluoro-2-(4-methoxybenzyl)-3-oxoisoindoline-1-carboxylate

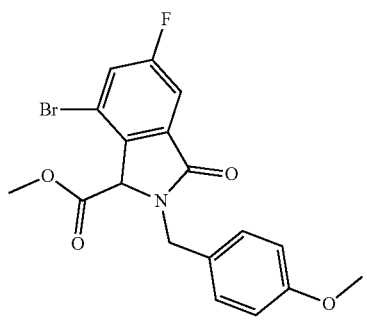

2,2'-Azobis(2-methylpropionitrile) (1.82 g, 11.1 mmol) was added in one portion to methyl 3-bromo-5-fluoro-2-(2-methoxy-2-oxoethyl)benzoate (11.3 g, 37.0 mmol) and NBS (7.25 g, 40.7 mmol) in 1,2-dichloroethane (150 mL) at rt. The reaction mixture was stirred at 80° C. for 2 days, cooled and the solvent was removed in vacuo. The crude product was purified by flash silica chromatography, elution gradient 0 to 5% EtOAc in petroleum ether (60-90° C.). Fractions were evaporated to dryness to afford rac-methyl 3-bromo-2-(1-bromo-2-methoxy-2-oxoethyl)-5-fluorobenzoate (12.0 g, 84%) as a colourless liquid. Sodium bicarbonate (10.5 g, 125 mmol) was added in one portion to rac-methyl 3-bromo-2-(1-bromo-2-methoxy-2-oxoethyl)-5-fluorobenzoate (12.0 g, 31.3 mmol) and 4-methoxybenzylamine (2.14 g, 15.6 mmol) in MeCN (100 mL) at rt. The reaction mixture was stirred at 80° C. for 16 hours and cooled to rt. The reaction mixture was filtered through Celite® and the solvent was removed in vacuo. The crude product was purified by flash silica chromatography, elution gradient 0 to 20% EtOAc in petroleum ether (60-90° C.). Pure fractions were evaporated to dryness to afford the title compound (2.56 g, 20%) as a colourless gum.

$^1$H NMR (300 MHz, CDCl₃) 3.67 (3H, s), 3.82 (3H, s), 4.26 (1H, d), 4.87 (1H, s), 5.12 (1H, d), 6.89 (2H, d), 7.27 (2H, d), 7.44 (1H, dd), 7.57 (1H, dd); m/z MH⁺ 408.

Intermediate AN: rac-Methyl 1-allyl-7-bromo-5-fluoro-2-[(4-methoxyphenyl)methyl]-3-oxo-isoindoline-1-carboxylate

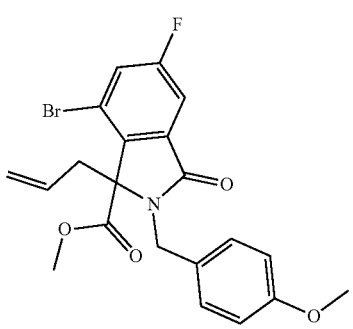 [SMILES: C=CCC1(C(=O)OC)c2c(Br)cc(F)cc2C(=O)N1Cc1ccc(OC)cc1]

3-Bromoprop-1-ene (4.03 g, 33.29 mmol) was added to methyl rac-methyl 7-bromo-5-fluoro-2-(4-methoxybenzyl)-3-oxoisoindoline-1-carboxylate (4.53 g, 11.10 mmol) and caesium carbonate (10.9 g, 33.3 mmol) in DMF (55 mL). The reaction mixture was stirred at 80° C. for 1 hour. The reaction mixture was allowed to cool and partitioned between EtOAc (250 mL) and water (250 mL). The organic phase was washed with water (2×100 mL), brine (100 mL), dried over MgSO₄, filtered and the solvent was removed in vacuo. The crude product was purified by flash silica chromatography, elution gradient 0 to 20% EtOAc in petroleum ether (60-90° C.). Pure fractions were evaporated to dryness to afford the title compound (4.17 g, 84%) as a white solid.

$^1$H NMR (300 MHz, DMSO-d6) 3.09 (s, 2H), 3.25-3.41 (m, 3H), 3.73 (d, 3H), 4.34 (d, 1H), 4.75-5.12 (m, 4H), 6.83-6.92 (m, 2H), 7.17-7.29 (m, 2H), 7.69 (dd, 1H), 7.91 (dd, 1H); m/z MH$^+$ 448.

Intermediate AO: rac-Methyl 7-bromo-5-fluoro-2-[(4-methoxyphenyl)methyl]-3-oxo-1-(2-oxoethyl)isoindoline-1-carboxylate

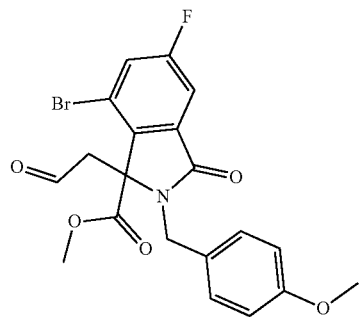 [SMILES: COC(=O)C1(CC=O)c2c(Br)cc(F)cc2C(=O)N1Cc1ccc(OC)cc1]

Potassium osmate(VI) dihydrate (0.07 g, 0.19 mmol) was added to rac-methyl 1-allyl-7-bromo-5-fluoro-2-[(4-methoxyphenyl)methyl]-3-oxo-isoindoline-1-carboxylate (4.17 g, 9.30 mmol), 2,6-lutidine (1.99 g, 18.6 mmol) and sodium periodate (5.97 g, 27.9 mmol) in dioxane (90 mL) and water (30 mL). The reaction mixture was stirred at rt for 3 hours. The reaction mixture was diluted with ethyl acetate (200 ml) and water (200 mL). The organic phase was dried over Na$_2$SO$_4$, filtered and the solvent was removed in vacuo. The crude product was purified by flash silica chromatography, elution gradient 0 to 30% EtOAc in petroleum ether (60-90° C.). Pure fractions were evaporated to dryness to afford the title compound (3.31 g, 79%) as a white solid.

$^1$H NMR (400 MHz, DMSO-d6) 3.12 (3H, s), 3.71 (3H, s), 3.73-3.78 (2H, m), 4.41 (1H, d), 4.88 (1H, d), 6.83-6.91 (2H, m), 7.18-7.25 (2H, m), 7.69-7.76 (1H, m), 7.85-7.93 (1H, m), 9.16 (1H, d); m/z MH$^+$ 450.

Intermediate AP: rac 4-Bromo-6-fluoro-2-[(4-methoxyphenyl)methyl]-1'-methyl-spiro[isoindoline-3,3'-pyrrolidine]-1,2'-dione

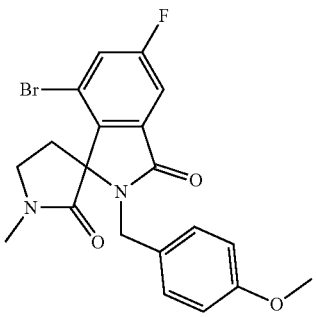

Sodium acetate (2.58 g, 31.5 mmol) was added to methylamine hydrochloride (1.06 g, 15.7 mmol) and rac-methyl 7-bromo-5-fluoro-2-[(4-methoxyphenyl)methyl]-3-oxo-1-(2-oxoethyl)isoindoline-1-carboxylate (3.54 g, 7.86 mmol) in 1,2-dichloroethane (70 mL) at rt. After 1 hour sodium triacetoxyborohydride (5.00 g, 23.59 mmol) was added, the reaction mixture was stirred at 60° C. for 16 hours and allowed to cool to rt. The reaction mixture was quenched with saturated NH$_4$Cl (100 mL) and extracted with EtOAc (200 mL). The organic phase was dried over Na$_2$SO$_4$, filtered and the solvent was removed in vacuo. The crude product was purified by flash silica chromatography, elution gradient 0 to 70% EtOAc in petroleum ether petroleum ether (60-90° C.). Pure fractions were evaporated to dryness to afford the title compound (1.20 g, 35%) as a white solid.

$^1$H NMR (400 MHz, DMSO-d6) 2.16-2.29 (1H, m), 2.51 (1H, d), 2.71 (3H, s), 3.56 (2H, t), 3.73 (3H, s), 4.45 (1H, d), 4.62 (1H, d), 6.83-6.91 (2H, m), 7.20-7.29 (2H, m), 7.65 (1H, dd), 7.87 (1H, dd), m/z MH$^+$ 433

Intermediate AQ: tert-Butyl (6-chloro-5-fluoropyridin-3-yl)carbamate

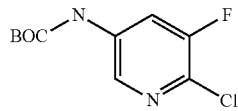

To 5-bromo-2-chloro-3-fluoropyridine (100 g, 475.22 mmol) in dioxane (1 L) was added tert-butyl carbamate (61.20 g, 522.74 mmol) and caesium carbonate (310.00 g, 950.43 mmol). The solution was degassed under vacuum and purged with an inert atmosphere of nitrogen for 5 minutes followed by the addition of tris(dibenzylideneacetone)dipalladium(0) (13.06 g, 14.26 mmol) and (9,9-dimethyl-9H-xanthene-4,5-diyl)bis(diphenylphosphane) (Xantphos) (11.00 g, 19.01 mmol). The reaction mixture was heated to 85° C. under nitrogen for 16 hours and then cooled to rt. The solid was filtered off and washed with excess dioxane. The solvent was removed in vacuo to afford crude title compound (179 g, 153%) as a dark orange gum that solidified on standing. The crude gum was used directly in next step without further purification.

$^1$H NMR (400 MHz, DMSO-d6, 30° C.) 1.49 (9H, s), 7.98 (1H, dd), 8.29 (1H, d), 9.98 (1H, s); m/z MH$^+$ 247.

Intermediate AR: 6-Chloro-5-fluoropyridin-3-amine

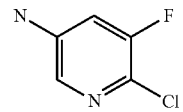

4M HCl in 1,4-dioxane (137 mL, 547.3 mmol) was added in one portion to a solution of tert-butyl (6-chloro-5-fluoropyridin-3-yl)carbamate (36 g, 109.5 mmol) in 1,4-dioxane (20 mL) at 20° C. The resulting suspension was stirred at 20° C. for 3 days. The reaction mixture was diluted with water (250 mL) and EtOAc (100 mL). The organic phase was separated and extracted with 2M HCl (3×100 mL) until no more product remained in the organic phase. The combined aqueous phases were stirred and cooled to 0° C. in an ice bath. The reaction mixture was basified to pH14 with 50% NaOH solution. The reaction mixture was then extracted with EtOAc (2×250 mL), the combined organics were washed with saturated brine (50 mL), dried over MgSO$_4$, filtered and the solvent was removed in vacuo to afford the title compound (12.4 g, 77%) as a brown solid. Used directly in next step with no further purification.

$^1$H NMR (400 MHz, CDCl$_3$, 27° C.) 3.88 (s, 2H), 6.80 (dd, J=9.6, 2.5 Hz, 1H), 7.68 (d, J=2.5 Hz, 1H).

Intermediate AS 2-Bromo-6-chloro-5-fluoropyridin-3-amine

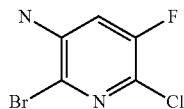

6-Chloro-5-fluoropyridin-3-amine (56.8 g, 379.3 mmol) in MeCN (250 mL) was cooled to 5° C. and a solution of NBS (67.50 g, 379.3 mmol) in MeCN (500 mL) was added over 15 minutes. The reaction mixture was warmed to rt and stirred for 45 minutes. Water (2 L) was added and the reaction mixture stirred for 30 minutes. The resulting solid was filtered off and washed with water (400 mL). The solid was dried under vacuum to afford the title compound (76 g, 89%) as a brown solid.

$^1$H NMR (400 MHz, DMSO-d6, 30° C.) 6.01 (2H, s), 7.12 (1H, d); m/z MH$^+$ 225

Intermediate AT: 5-Chloro-6-fluoro-1H-pyrrolo[3,2-b]pyridine-2-carboxylic acid

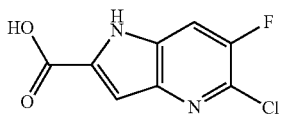 [SMILES: O=C(O)c1cc2nc(Cl)c(F)cc2[nH]1]

Palladium acetate (3.35 g, 14.93 mmol), triphenylphosphine (3.92 g, 14.93 mmol), 2-bromo-6-chloro-5-fluoropyridin-3-amine (18.0 g, 74.65 mmol) and pyruvic acid (15.57 mL, 224 mmol) were place in a flask with 1,4-dioxane (88 mL). Triethylamine (45.80 mL, 328.5 mmol) was added and the reaction was heated at 100° C. for 2.5 hours under nitrogen. The reaction mixture was cooled to rt and filtered to remove unwanted solids. The filtrate was diluted with 2M NaOH (200 mL) and MTBE (200 mL) was added. The reaction mixture was then stirred vigorously and separated. The organic phase was washed with 2M NaOH (100 mL). The combined basic aqueous phases were carefully acidified with concentrated HCl (aqueous) and a brown solid precipitated which was collected by filtration and dried. The dark brown solid was suspended in MeOH (90 mL) and stirred for 2 hours at rt. The solid was filtered and dried under vacuum to afford the title compound (14.60 g, 91%) as a beige solid.

$^1$H NMR (400 MHz, DMSO-d6, 30° C.) 7.16 (1H, dd), 7.84 (1H, dd), 12.36 (1H, s), 13.46 (1H, s); m/z MH$^+$ 214.

Intermediate AU: Methyl 5-chloro-6-fluoro-1H-pyrrolo[3,2-b]pyridine-2-carboxylate

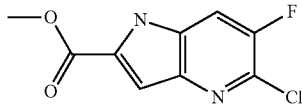

Sulfuric acid (3.08 mL, 57.83 mmol) was added dropwise carefully to 5-chloro-6-fluoro-1H-pyrrolo[3,2-b]pyridine-2-carboxylic acid (14.60 g, 57.83 mmol) in MeOH (113 mL) at rt. The reaction mixture was stirred at reflux for 18 hours. The reaction mixture was allowed to cool and the solvent was removed in vacuo. Saturated NaHCO$_3$ (400 mL) was carefully added to the residue and the resulting precipitate was filtered off, washed with water and dried under vacuum to afford the title compound (14.20 g, 107%) as a brown solid.

$^1$H NMR (400 MHz, DMSO-d6, 30° C.) 3.91 (3H, s), 7.24 (1H, dd), 7.88 (1H, dd), 12.56 (1H, s); m/z MH$^+$ 229

Intermediate AV: Methyl 5-chloro-6-fluoro-1-((2-(trimethylsilyl)ethoxy)methyl)-1H-pyrrolo[3,2-b]pyridine-2-carboxylate

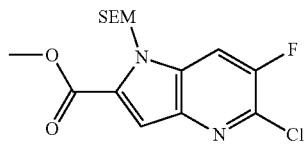 [SMILES: COC(=O)c1cc2nc(Cl)c(F)cc2n1COCC[Si](C)(C)C]

Potassium bis(trimethylsilyl)amide (1M in THF) (101 mL, 100.9 mmol) was added dropwise over 15 minutes to a solution of methyl 5-chloro-6-fluoro-1H-pyrrolo[3,2-b]pyridine-2-carboxylate (21.74 g, 77.60 mmol) and (2-(chloromethoxy)ethyl)trimethylsilane (18.83 mL, 100.9 mmol) in THF (419 mL) at 5° C. under nitrogen. The reaction mixture was stirred at 5° C. for 30 minutes. Potassium bis(trimethylsilyl)amide (1M in THF) (15.52 mL, 15.52 mmol) was added and the reaction mixture was stirred at 5° C. for a further 30 minutes. (2-(Chloromethoxy)ethyl)trimethylsilane (1.88 mL, 10.09 mmol) was added and stirred at 5° C. for a further 15 minutes. The reaction mixture was quenched with saturated NH$_4$Cl (400 mL) and diluted with EtOAc (400 mL). The aqueous phase was re-extracted with EtOAc (250 mL). The combined organic phases were dried over MgSO$_4$, filtered and the solvent was removed in vacuo. The crude material was suspended in heptane (450 mL) and stirred for 5 minutes. The unrequired solid was filtered off and washed with heptane (50 mL). The solvent was removed in vacuo to afford the title compound (32.50 g, 117%) as a brown gum which solidified on standing. The gum was Used directly in next step without further purification.

$^1$H NMR (400 MHz, DMSO-d6, 30° C.) −0.13 (9H, s), 0.70-0.80 (2H, m), 3.38-3.51 (2H, m), 3.89 (3H, s), 5.95 (2H, s), 7.41 (1H, d), 8.40-8.54 (1H, m); m/z MH$^+$ 359

Intermediate AW: (5-Chloro-6-fluoro-1-((2-(trimethylsilyl)ethoxy)methyl)-1H-pyrrolo[3,2-b]pyridin-2-yl)methanol

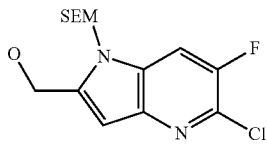 [SMILES: C[Si](C)(C)CCOCn1c(CO)cc2nc(Cl)c(F)cc21]

Diisobutylaluminum hydride (1M in toluene) (170 mL, 170.42 mmol) was added dropwise to a stirred solution of methyl 5-chloro-6-fluoro-1-((2-(trimethylsilyl)ethoxy)methyl)-1H-pyrrolo[3,2-b]pyridine-2-carboxylate (27.80 g, 77.47 mmol) in DCM (333 mL) at 5° C. over 15 minutes. The reaction mixture was stirred at rt for 30 minutes. The reaction mixture was carefully poured into 2M NaOH (500 mL), diluted with DCM (500 mL) and stirred for 1 hour. The organic phase was separated and the aqueous phase was extracted with DCM (2×200 mL). The combined organics were dried with MgSO$_4$, filtered and the solvent was removed in vacuo. The crude product was purified by flash silica chromatography, elution gradient 0 to 40% EtOAc in heptane. Pure fractions were evaporated to dryness to afford the title compound (17.60 g, 68%) as a pale orange oil which solidified on standing.

¹H NMR (400 MHz, DMSO-d6, 30° C.) −0.10 (9H, s), 0.75-0.83 (2H, m), 3.36-3.56 (2H, m), 4.72 (2H, d), 5.50 (1H, t), 5.60 (2H, s), 6.57 (1H, d), 8.24 (1H, dd); m/z MH⁺ 331

Intermediate AX: 5-Chloro-2-(chloromethyl)-6-fluoro-1-((2-(trimethylsilyl)ethoxy)methyl)-1H-pyrrolo[3,2-b]pyridine

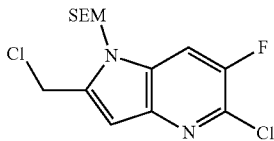 [SMILES: C[Si](C)(C)CCOCn1c(CCl)cc2nc(Cl)c(F)cc21]

Thionyl chloride (13.2 mL, 181.4 mmol) was added dropwise carefully to (5-chloro-6-fluoro-1-((2-(trimethylsilyl)ethoxy)methyl)-1H-pyrrolo[3,2-b]pyridin-2-yl)methanol (20.0 g, 60.45 mmol) in DCM (200 mL) at rt. The reaction mixture was stirred at rt for 1 hour. Saturated NaHCO₃ (500 mL) was then slowly added. Once gas evolution had ceased the phases were separated and the aqueous phase was re-extracted with DCM (300 mL). The organic phases were combined, washed with brine (200 mL), passed through a phase separating filter paper and the solvent was removed in vacuo to afford the title compound (19.2 g, 91%) as a brown crystalline solid.

¹H NMR (400 MHz, DMSO-d6, 27° C.) −0.10 (9H, s), 0.75-0.9 (2H, m), 3.43-3.53 (2H, m), 5.07 (2H, s), 5.66 (2H, s), 6.7-6.9 (1H, m), 8.32 (1H, dd); m/z MH⁺ 349

Intermediate AY: 5-Chloro-2-(bromomethyl)-6-fluoro-1-((2-(trimethylsilyl)ethoxy)methyl)-1H-pyrrolo[3,2-b]pyridine

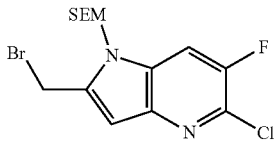

Phosphorus tribromide (2.57 mL, 27.20 mmol) was added to (5-chloro-6-fluoro-1-((2-(trimethylsilyl)ethoxy)methyl)-1H-pyrrolo[3,2-b]pyridin-2-yl)methanol (3.00 g, 9.07 mmol) in THF (30 mL) at rt. The reaction mixture was stirred at rt for 1 hour. The reaction mixture was quenched with saturated NaHCO₃ (150 mL) and extracted with EtOAc (3×125 mL). The organic phase was dried over Na₂SO₄, filtered and the solvent was removed in vacuo. The crude product was purified by flash silica chromatography, elution gradient 0 to 30% EtOAc in petroleum ether (60-90° C.). Pure fractions were evaporated to dryness to afford the title compound (3.00 g, 84%) as a pale yellow solid.

¹H NMR (300 MHz, CDCl₃) −0.02 (9H, s), 0.84-1.01 (2H, m), 3.44-3.61 (2H, m), 4.74 (2H, s), 5.58 (2H, s), 6.73-6.79 (1H, m), 7.51-7.63 (1H, m); m/z MH⁺ 395.

Intermediate AZ: Methyl 1H-pyrrolo[2,3-b]pyridine-2-carboxylate

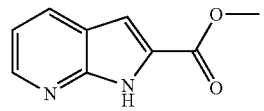

Thionyl chloride (11.25 mL, 154.2 mmol) was added dropwise carefully to 1H-pyrrolo[2,3-b]pyridine-2-carboxylic acid (CAS No. 136818-50-3) (25.0 g, 154.2 mmol) in methanol (200 mL) at rt. The reaction mixture was stirred at 60° C. for 18 hours. The reaction mixture was allowed to cool and the solvent was removed in vacuo. The residue was triturated with saturated NaHCO₃ (250 mL). The resulting precipitate was filtered off, washed with water (2×200 mL), then washed with ether (200 mL) and dried under vacuum to afford the title compound (24.3 g, 90%) as a beige solid.

¹H NMR (400 MHz, DMSO-d6, 30° C.) 3.89 (3H, s), 7.12-7.22 (2H, m), 8.12 (1H, dd), 8.42 (1H, dd), 12.48 (1H, s); m/z MH⁺ 177

Intermediate BA: 2-(Methoxycarbonyl)-1H-pyrrolo[2,3-b]pyridine 7-oxide

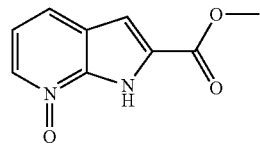

Methyl 1H-pyrrolo[2,3-b]pyridine-2-carboxylate (24.30 g, 137.93 mmol) was suspended in diethyl ether (500 mL). 3-Chlorobenzoperoxoic acid (61.80 g, 275.86 mmol) was added and the reaction mixture was stirred at rt for 5 hours. The solvent was removed in vacuo and the solid was triturated in saturated NaHCO₃ (200 mL). The precipitate was filtered off, washed with water and dried to afford the title compound (20.23 g, 76%) as a cream solid.

¹H NMR (400 MHz, DMSO-d6, 30° C.) 3.87 (3H, s), 7.16 (1H, dd), 7.30 (1H, s), 7.75 (1H, dd), 8.31 (1H, dd) (NH lost under water signal); m/z MH⁺ 193.

Intermediate BB: Methyl 4-bromo-1H-pyrrolo[2,3-b]pyridine-2-carboxylate

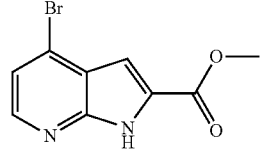

2-(Methoxycarbonyl)-1H-pyrrolo[2,3-b]pyridine 7-oxide (20.0 g, 104.1 mmol) and tetrabutylammonium bromide (50.3 g, 156.1 mmol) were placed in a flask with 1,2-dimethoxyethane (75 mL) and cooled to 0° C. Methanesulfonic anhydride (36.30 g, 208.1 mmol) was slowly added and the reaction mixture was stirred at rt for 3 hours. The solvent was removed in vacuo, the residue was cooled on ice and quenched/ triturated with saturated NaHCO₃ (40 mL). The solid was filtered, washed with water and dried to afford the title compound (22.80 g, 86%) as an orange solid.

¹H NMR (400 MHz, DMSO-d6, 30° C.) 3.91 (3H, s), 7.07 (1H, d), 7.48 (1H, d), 8.29 (1H, d), 12.95 (1H, s); m/z MH⁺ 255

Intermediate BC: Methyl 4-methyl-1H-pyrrolo[2,3-b]pyridine-2-carboxylate

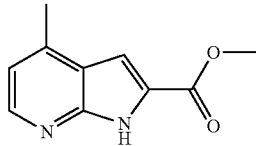

Methyl 4-bromo-1H-pyrrolo[2,3-b]pyridine-2-carboxylate (10.0 g, 39.2 mmol), 2,4,6-trimethyl-1,3,5,2,4,6-trioxatriborinane (16.44 mL, 117.6 mmol) and potassium phosphate (16.64 g, 78.41 mmol) were placed in a flask with dioxane (100 mL). Pd 118 (0.64 g, 0.98 mmol) was added and the reaction mixture was heated to 100° C. for 2 hours. The reaction mixture was allowed to cool, the solid was filtered off and washed with EtOAc (2×100 mL). The filtrates were combined and the solvents were removed in vacuo. The residue was triturated with EtOAc (100 mL) and the solid was filtered off, washed with a small amount of EtOAc (20 mL) and dried to afford the title compound (5.58 g, 74%) as a beige solid.

$^1$H NMR (400 MHz, DMSO-d6, 30° C.) 2.48-2.51 (3H, m), 3.83 (3H, s), 6.92 (1H, dd), 7.20 (1H, s), 8.22 (1H, d), 12.34 (1H, s); m/z MH$^+$ 191

Intermediate BD: 2-(Methoxycarbonyl)-4-methyl-1H-pyrrolo[2,3-b]pyridine 7-oxide

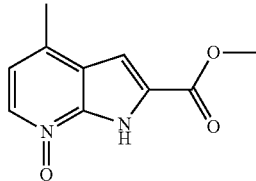

Methyl 4-methyl-1H-pyrrolo[2,3-b]pyridine-2-carboxylate (5.05 g, 26.55 mmol) was suspended in diethyl ether (100 mL). 3-Chlorobenzoperoxoic acid (11.90 g, 53.10 mmol) was added and the reaction mixture was stirred at rt for 2 hours. The solvent was removed in vacuo and the solid was triturated in saturated NaHCO$_3$ (50 mL). The precipitate was filtered off, washed with water and dried to afford the title compound (4.64 g, 85%) as a cream solid.

$^1$H NMR (400 MHz, DMSO-d6, 30° C.) 2.57 (3H, s), 3.92 (3H, s), 7.03 (1H, dd), 7.41 (1H, s), 8.19-8.37 (1H, m) (NH under water peak); m/z MH$^+$ 207

Intermediate BE: Methyl 6-chloro-4-methyl-1H-pyrrolo[2,3-b]pyridine-2-carboxylate

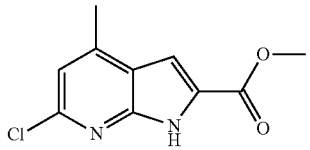

2-(Methoxycarbonyl)-4-methyl-1H-pyrrolo[2,3-b]pyridine 7-oxide (4.35 g, 21.10 mmol) was suspended in THF (80 mL) and bis(trimethylsilyl)amine (4.42 mL, 21.10 mmol) was added. 2,2,2-Trichloroacetyl chloride (5.65 mL, 50.63 mmol) was added dropwise and the reaction mixture was stirred at rt for 1 hour. The reaction mixture was partitioned between EtOAc (200 mL) and saturated sodium bicarbonate solution (200 mL). The organic phase was passed through a phase separating filter paper and the solvent was removed in vacuo. The crude product was purified by flash silica chromatography, elution gradient 0 to 50% EtOAc in heptane. Fractions were evaporated to dryness to afford the title compound (5.50 g, 116%) as a white solid containing a 50% impurity of trichloroacetamide. The crude compound was used without further purification in the next reaction.

$^1$H NMR (400 MHz, DMSO-d6, 30° C.) 2.55 (3H, d), 3.89 (3H, s), 7.08 (1H, d), 7.30 (1H, d), 12.66 (1H, s); m/z MH$^+$ 225.

Intermediate BF: Methyl 6-chloro-4-methyl-1-((2-(trimethylsilyl)ethoxy)methyl)-1H-pyrrolo[2,3-b]pyridine-2-carboxylate

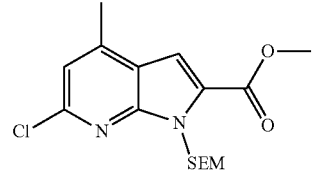 [SMILES: COC(=O)c1cc2c(C)cc(Cl)nc2n1COCC[Si](C)(C)C]

Methyl 6-chloro-4-methyl-1H-pyrrolo[2,3-b]pyridine-2-carboxylate (5.00 g, 22.26 mmol) was placed in a flask with DMF (25 mL). Sodium hydride (60% in mineral oil) (1.33 g, 33.39 mmol) was added and the reaction mixture was stirred at rt for 5 minutes. (2-(Chloromethoxy)ethyl)trimethylsilane (5.12 mL, 28.93 mmol) was then added and the reaction mixture was stirred at rt for 1 hour. The reaction mixture was partitioned between EtOAc (150 mL) and water (100 mL). The organic phase was washed with water (3×100 mL) and brine (100 mL), passed through a phase separating filter paper and the solvent was removed in vacuo. The crude product was purified by flash silica chromatography, elution gradient 0 to 50% EtOAc in heptane. Pure fractions were evaporated to dryness to afford the title 20 compound (4.80 g, 60%) as a colourless oil which crystallised on standing.

$^1$H NMR (400 MHz, DMSO-d6, 30° C.) −0.14 (9H, s), 0.75-0.82 (2H, m), 2.57 (3H, d), 3.41-3.49 (2H, m), 3.88 (3H, s), 5.92 (2H, s), 7.19 (1H, d), 7.49 (1H, s); m/z MH$^+$ not observed.

Intermediate BG: (6-Chloro-4-methyl-1-((2-(trimethylsilyl)ethoxy)methyl)-1H-pyrrolo[2,3-b]pyridin-2-yl)methanol

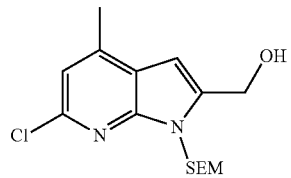 [SMILES: Cc1cc(Cl)nc2c1cc(CO)n2COCC[Si](C)(C)C]

Diisobutylaluminum hydride 1M in toluene (29.8 mL, 29.75 mmol) was added dropwise to a stirred solution of methyl 6-chloro-4-methyl-1-((2-(trimethylsilyl)ethoxy)methyl)-1H-pyrrolo[2,3-b]pyridine-2-carboxylate (4.80 g, 13.52 mmol) in DCM (100 mL) at rt. The reaction mixture was stirred for 30 minutes and then partitioned between 2M NaOH (50 mL) and DCM (100 mL). The organic phase was separated and the aqueous phase was extracted with DCM (100 mL). The combined organics were passed through a phase separating filter paper and the solvent was removed in vacuo. The crude product was purified by flash silica chromatography, elution gradient 0 to 40% EtOAc in heptane. Pure fractions were evaporated to dryness to afford the title compound (3.30 g, 74%) as a yellow oil.

$^1$H NMR (400 MHz, DMSO-d6, 30° C.) −0.11 (9H, s), 0.83 (2H, dd), 2.49 (3H, d), 3.42-3.51 (2H, m), 4.65-4.75 (2H, m), 5.38 (1H, t), 5.62 (2H, s), 6.55 (1H, s), 7.02 (1H, d); m/z MH$^+$ 327.

Intermediate BH: 6-Chloro-2-(chloromethyl)-4-methyl-1-((2-(trimethylsilyl)ethoxy)methyl)-1H-pyrrolo[2,3-b]pyridine

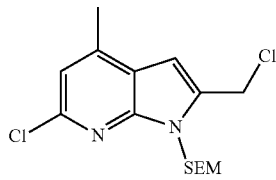 [SMILES: Cc1cc(Cl)nc2c1cc(CCl)n2COCC[Si](C)(C)C]

Thionyl chloride (0.67 mL, 9.18 mmol) was added dropwise carefully to (6-chloro-4-methyl-1-((2-(trimethylsilyl)ethoxy)methyl)-1H-pyrrolo[2,3-b]pyridin-2-yl)methanol (1.00 g, 3.06 mmol) in DCM (20 mL) at rt. The reaction mixture was stirred at rt for 1 hour. The reaction mixture was quenched with saturated NaHCO$_3$, the organic phase was passed through a phase separator and the solvent was removed in vacuo. The crude product was purified by flash silica chromatography, elution gradient 0 to 50% EtOAc in heptane. Pure fractions were evaporated to dryness to afford the title compound (0.71 g, 67%) as a pale yellow oil which slowly crystallised to give a cream solid.

$^1$H NMR (400 MHz, DMSO-d6, 30° C.) −0.11 (9H, s), 0.83-0.87 (2H, m), 2.51 (3H, s), 3.46-3.54 (2H, m), 5.04 (2H, s), 5.67 (2H, s), 6.82 (1H, s), 7.09 (1H, d).

Intermediate BI: 7-Chloro-2-(ethoxycarbonyl)-1H-pyrrolo[3,2-b]pyridine 4-oxide

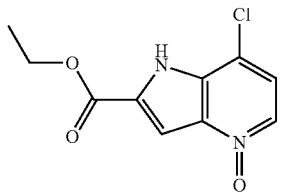 [SMILES: CCOC(=O)c1cc2c([nH]1)c(Cl)cc[n+]2[O-]]

3-Chlorobenzoperoxoic acid (5.76 g, 33.39 mmol) was added to ethyl 7-chloro-1H-pyrrolo[3,2-b]pyridine-2-carboxylate (5.00 g, 22.26 mmol) in DCM (120 mL) over a period of 5 minutes. The reaction mixture was stirred at rt for 16 hours. The reaction mixture was diluted with DCM (50 mL), washed with saturated Na$_2$SO$_3$ (100 mL), saturated NaHCO$_3$ (100 mL), and saturated brine (100 mL). The solvent was removed in vacuo. The crude product was purified by flash silica chromatography, elution gradient 0 to 10% MeOH in DCM. Pure fractions were evaporated to dryness to afford the title compound (5.27 g, 98%) as a yellow solid.

$^1$H NMR (400 MHz, CDCl$_3$) 1.43 (3H, t), 4.41-4.51 (2H, m), 7.20 (1H, d), 7.61 (1H, s), 8.19 (1H, d), 9.94 (1H, s); m/z MH$^+$ 241

Intermediate BJ: Ethyl 5-bromo-7-chloro-1H-pyrrolo[3,2-b]pyridine-2-carboxylate

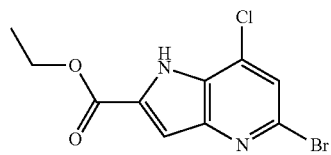 [SMILES: CCOC(=O)c1cc2nc(Br)cc(Cl)c2[nH]1]

Phosphoryl tribromide (12.56 g, 43.80 mmol) was added to 7-chloro-2-(ethoxycarbonyl)-1H-pyrrolo[3,2-b]pyridine 4-oxide (5.27 g, 21.90 mmol) in THF (160 mL) at rt. The reaction mixture was stirred at rt for 16 hours. The reaction mixture was neutralised with saturated NaHCO$_3$ and diluted with EtOAc (100 mL) and water (100 mL). The aqueous phase was extracted with EtOAc (2×100 mL). The organics were combined, dried over Na$_2$SO$_4$, filtered and the solvent was removed in vacuo. The crude product was purified by flash silica chromatography, elution gradient 0 to 25% EtOAc in petroleum ether (60-90° C.). Pure fractions were evaporated to dryness to afford the title compound (4.20 g, 63%) as a white solid.

$^1$H NMR (300 MHz, DMSO-d6) 1.34 (3H, t), 2.52 (1H, s), 4.31-4.44 (2H, m), 7.27 (1H, d), 7.69 (1H, s); m/z MH$^+$ 303

Intermediate BK: Ethyl 5-bromo-7-chloro-1-((2-(trimethylsilyl)ethoxy)methyl)-1H-pyrrolo[3,2-b]pyridine-2-carboxylate

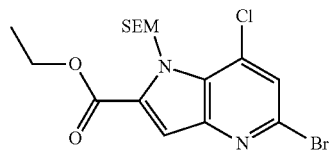 [SMILES: CCOC(=O)c1cc2nc(Br)cc(Cl)c2n1COCC[Si](C)(C)C]

Sodium hydride (60% in mineral oil) (0.719 g, 17.99 mmol) was added to ethyl 5-bromo-7-chloro-1H-pyrrolo[3,2-b]pyridine-2-carboxylate (4.20 g, 13.84 mmol) in THF (70 mL) at 0° C. over a period of 5 minutes. The reaction mixture was stirred at rt for 1 hour. (2-(Chloromethoxy)ethyl)trimethylsilane (0.60 mL, 3.38 mmol) was added and the reaction mixture was stirred for 16 hours. The reaction mixture was quenched with saturated NH$_4$Cl (20 mL) and extracted with EtOAc (3×20 mL). The organic phase was dried over Na$_2$SO$_4$, filtered and the solvent was removed in vacuo. The crude product was purified by flash silica chromatography, elution gradient 0 to 12% EtOAc in petroleum ether (60-90° C.). Pure fractions were evaporated to dryness to afford the title compound (5.40 g, 90%) as a colourless oil.

$^1$H NMR (300 MHz, DMSO-d6) −0.16 (9H, s), 0.74 (2H, t), 1.34 (3H, t), 3.37-3.49 (2H, m), 4.30-4.46 (2H, m), 6.19 (2H, s), 7.42 (1H, s), 7.77 (1H, s); m/z MH$^+$ 433.

Intermediate BL: (5-Bromo-7-chloro-1-((2-(trimethylsilyl)ethoxy)methyl)-1H-pyrrolo[3,2-b]pyridin-2-yl)methanol

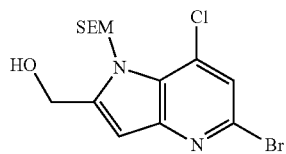

Diisobutylaluminum hydride (1M in toluene) (20.75 mL, 20.75 mmol) was added to ethyl 5-bromo-7-chloro-1-((2-(trimethylsilyl)ethoxy)methyl)-1H-pyrrolo[3,2-b]pyridine-2-carboxylate (3.00 g, 6.92 mmol) in THF (20 mL) at 0° C. The resulting solution was stirred at rt for 1 hour. The reaction mixture was quenched with saturated Rochelle salt (potassium sodium tartrate tetrahydrate) (15 mL) and extracted with EtOAc (3×20 mL). The organic phase was dried over Na$_2$SO$_4$, filtered and the solvent was removed in vacuo to afford the title compound (2.60 g, 96%) as a yellow oil.

$^1$H NMR (300 MHz, DMSO-d6) −0.12 (9H, s), 0.78 (2H, t), 3.51 (2H, t), 4.74 (2H, d), 5.76 (2H, s), 6.58-6.66 (1H, m), 7.47 (1H, s); m/z MH$^+$ 391.

Intermediate BM: 5-Bromo-2-(bromomethyl)-7-chloro-1-((2-(trimethylsilyl)ethoxy)methyl)-1H-pyrrolo[3,2-12]pyridine

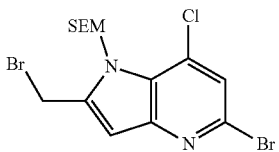 [SMILES: C[Si](C)(C)CCOCn1c(CBr)cc2nc(Br)cc(Cl)c21]

Phosphorus tribromide (0.65 mL, 6.89 mmol) was added dropwise to (5-bromo-7-chloro-1-((2-(trimethylsilyl)ethoxy)methyl)-1H-pyrrolo[3,2-b]pyridin-2-yl)methanol (2.25 g, 5.74 mmol) in THF (40 mL) at 0° C. The reaction mixture was stirred at rt for 2 hours. The reaction mixture was quenched with saturated NaHCO$_3$ (20 mL) and extracted with EtOAc (3×25 mL). The organic phase was dried over Na$_2$SO$_4$, filtered and the solvent was removed in vacuo. The crude product was purified by flash silica chromatography, elution gradient 0 to 10% EtOAc in petroleum ether (60-90° C.). Pure fractions were evaporated to dryness to afford the title compound (2.15 g, 82%) as a colourless oil.

$^1$H NMR (300 MHz, DMSO-d6) −0.12 (9H, s), 0.72-0.85 (2H, m), 3.54 (2H, t), 5.01 (2H, s), 5.80 (2H, s), 6.91 (1H, s), 7.55 (1H, s); m/z MH$^+$ 455.

Intermediate BN: Ethyl 5-chloro-1-tosyl-1H-pyrrolo[3,2-b]pyridine-2-carboxylate

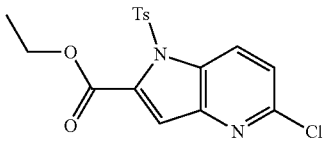 [SMILES: CCOC(=O)c1cc2nc(Cl)ccc2n1S(=O)(=O)c1ccc(C)cc1]

Sodium hydride (60% in mineral oil) (0.21 g, 5.34 mmol) was added to ethyl 5-chloro-1H-pyrrolo[3,2-b]pyridine-2-carboxylate (1.00 g, 4.45 mmol) in DMF (12 mL) at 0° C. After 30 minutes 4-toluenesulfonyl chloride (1.02 g, 5.34 mmol) was added. The reaction mixture was stirred at rt for 3 hours. The reaction mixture was quenched with NH$_4$Cl and the solvent was removed in vacuo. The crude product was purified by flash silica chromatography, elution gradient 0 to 30% EtOAc in petroleum ether (60-90° C.). Pure fractions were evaporated to dryness to afford the title compound (0.90 g, 53%) as a white solid.

$^1$H NMR (300 MHz, DMSO-d6) 1.33 (3H, t), 2.38 (3H, s), 4.30-4.46 (2H, m), 7.42-7.53 (3H, m), 7.58 (1H, d), 7.91-8.02 (2H, m), 8.47-8.56 (1H, m); m/z MH$^+$ 379

Intermediate BO: (5-Chloro-1-tosyl-1H-pyrrolo[3,2-b]pyridin-2-yl)methanol

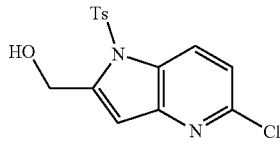 [SMILES: Cc1ccc(S(=O)(=O)n2c(CO)cc3nc(Cl)ccc32)cc1]

Ethyl 5-chloro-1-tosyl-1H-pyrrolo[3,2-b]pyridine-2-carboxylate (0.90 g, 2.38 mmol) was added to diisobutylaluminium hydride (1M in toluene) (7.13 mL, 7.13 mmol) in THF (6 mL). The reaction mixture was stirred at rt for 2 hours. The reaction mixture was quenched with saturated brine (100 mL) and extracted with EtOAc (3×50 mL). The organic phase was dried over Na$_2$SO$_4$, filtered and the solvent was removed in vacuo to afford the title compound (0.78 g, 97%) as a white solid.

$^1$H NMR (300 MHz, DMSO-d6) 2.34 (3H, s), 4.90 (2H, d), 5.75 (1H, t), 6.78-6.85 (1H, m), 7.34-7.46 (3H, m), 7.83-7.94 (2H, m), 8.37-8.46 (1H, m); m/z MH$^+$ 337.

Intermediate BP: 2-(Bromomethyl)-5-chloro-1-tosyl-1H-pyrrolo[3,2-b]pyridine

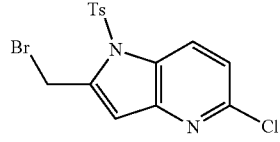

Phosphorus tribromide (0.33 mL, 3.47 mmol) was added to (5-chloro-1-tosyl-1H-pyrrolo[3,2-b]pyridin-2-yl)methanol (780 mg, 2.32 mmol) in THF (12 mL). The reaction mixture was stirred at rt for 1 hour. The reaction mixture was poured into saturated NaHCO$_3$ (25 mL) and extracted with EtOAc (3×15 mL). The organic phase was dried over Na$_2$SO$_4$, filtered and the solvent was removed in vacuo. The crude product was purified by flash silica chromatography, elution gradient 0 to 20% petroleum ether in EtOAc. Pure fractions were evaporated to dryness to afford the title compound (0.76 g, 82%) as a white solid.

$^1$H NMR (300 MHz, DMSO-d6) 2.34 (3H, s), 5.19 (2H, s), 7.21 (1H, d), 7.35-7.44 (2H, m), 7.47 (1H, d), 7.86-7.97 (2H, m), 8.37-8.50 (1H, m); m/z MH$^+$ 399

Intermediate BQ: Methyl (S)-1-allyl-2-((5-chloro-6-fluoro-1-((2-(trimethylsilyl)ethoxy)methyl)-1H-pyrrolo[3,2-b]pyridin-2-yl)methyl)-5-fluoro-3-oxoisoindoline-1-carboxylate

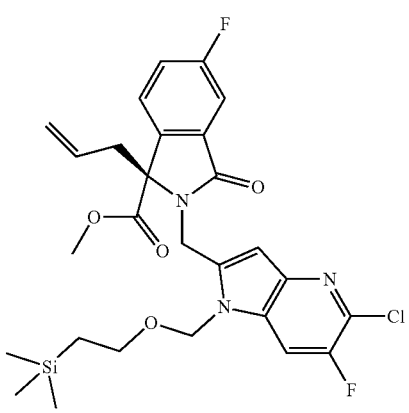 [SMILES: C=CC[C@@]1(C(=O)OC)c2ccc(F)cc2C(=O)N1Cc1cc2nc(Cl)c(F)cc2n1COCC[Si](C)(C)C]

Methyl (S)-1-allyl-5-fluoro-3-oxoisoindoline-1-carboxylate (11.80 g, 47.34 mmol) and 5-chloro-2-(chloromethyl)-6-fluoro-1-((2-(trimethylsilyl)ethoxy)methyl)-1H-pyrrolo[3,2-b]pyridine (16.9 g, 48.3 mmol) were placed in a flask with dry DMF (60 mL). Caesium carbonate (38.60 g, 118.4 mmol) was added and the reaction mixture was stirred at 60° C. for 2 hours. The reaction mixture was cooled and partitioned between water (300 mL) and EtOAc (300 mL). The aqueous phase was re-extracted with EtOAc (200 mL). The organic phases were combined, washed with water (3×200 mL), brine (200 mL), passed through a phase separating filter paper and the solvent was removed in vacuo. The crude product was purified by flash silica chromatography, elution gradient 0 to 100% EtOAc in heptane. Pure fractions were evaporated to dryness to afford the title compound (22.2 g, 83%) as a yellow gum which slowly solidified/crystallised to give a yellow solid.

¹H NMR (400 MHz, DMSO-d6, 27° C.) −0.09 (9H, s), 0.79-0.88 (2H, m), 3.03 (3H, s), 3.16-3.29 (2H, m), 3.46-3.60 (2H, m), 4.73 (1H, d), 4.89 (1H, dd), 4.94-5.10 (2H, m), 5.26 (1H, d), 5.59 (1H, d), 5.68 (1H, d), 6.76 (1H, s), 7.49-7.56 (1H, m), 7.58-7.68 (2H, m), 8.25 (1H, dd); m/z MH⁺ 562

Intermediate BR: Methyl (S)-1-allyl-2-((5-((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxoisoindoline-1-carboxylate

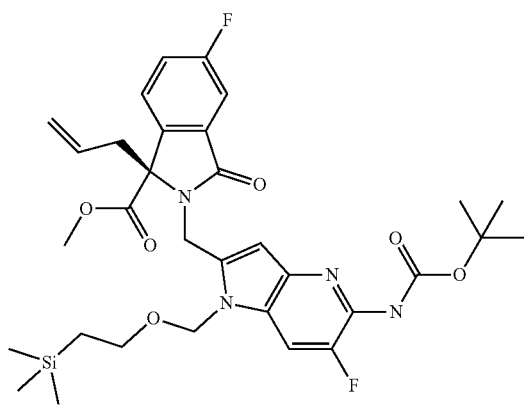 [SMILES: C=CC[C@@]1(C(=O)OC)c2ccc(F)cc2C(=O)N1Cc1cc2nc(NC(=O)OC(C)(C)C)c(F)cc2n1COCC[Si](C)(C)C]

Methyl (S)-1-allyl-2-((5-chloro-6-fluoro-1-((2-(trimethylsilyl)ethoxy)methyl)-1H-pyrrolo[3,2-b]pyridin-2-yl)methyl)-5-fluoro-3-oxoisoindoline-1-carboxylate (15 g, 26.69 mmol), caesium carbonate (21.74 g, 66.72 mmol), BrettPhos Pd G3 (2.42 g, 2.67 mmol), dicyclohexyl(2',4',6'-triisopropyl-3,6-dimethoxy-[1,1'-biphenyl]-2-yl)phosphane (1.43 g, 2.67 mmol) and tert-butyl carbamate (6.25 g, 53.37 mmol) were placed in a flask with degassed 2-methyltetrahydrofuran (150 mL). Nitrogen was bubbled through the reaction mixture for 10 minutes and then the reaction mixture was refluxed for 3 hours The reaction mixture was cooled, diluted with water (400 mL) and extracted with EtOAc (2×300 mL). The combined organic phases were washed with saturated brine (200 mL), passed through a phase separating filter paper and the solvent was removed in vacuo. The crude product was purified by flash silica chromatography, elution gradient 0 to 50% EtOAc in heptane. Pure fractions were evaporated to dryness to afford the title compound (11.68 g, 68%) as a pale yellow foam.

¹H NMR (400 MHz, DMSO-d6, 27° C.) −0.08 (9H, s), 0.82-0.86 (2H, m), 1.42 (9H, s), 2.99 (3H, s), 3.15-3.30 (2H, m), 3.52 (2H, dtd), 4.71 (1H, d), 4.88 (1H, dd), 4.94-5.10 (2H, m), 5.26 (1H, d), 5.55 (1H, d), 5.64 (1H, d), 6.69 (1H, s), 7.46-7.56 (1H, m), 7.57-7.66 (2H, m), 7.99 (1H, d), 9.18 (1H, s); m/z MH⁺ 643

Intermediate BS: Methyl (S)-2-((5-((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate carboxylate

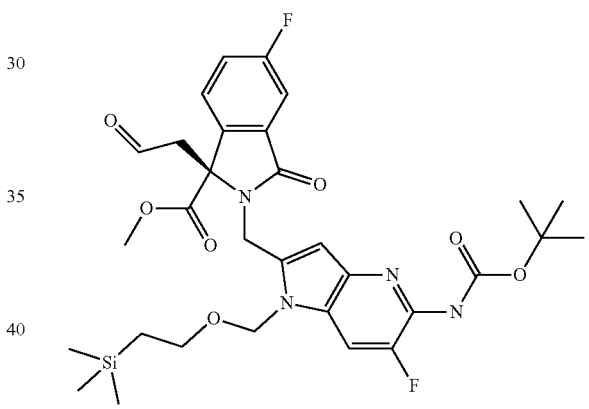

To a solution of methyl (S)-1-allyl-2-((5-((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxoisoindoline-1-carboxylate (11.50 g, 17.89 mmol) in 1,4-dioxane (240 mL) and water (60 mL) was added osmium (VIII) oxide (4% in water) (1.14 mL, 0.18 mmol), sodium periodate (9.57 g, 44.73 mmol) and 2,6-dimethylpyridine (4.17 mL, 35.78 mmol). The reaction mixture was stirred at rt for 18 hours. The reaction mixture was partitioned between DCM (200 mL) and water (100 mL). The aqueous phase was re-extracted with DCM (100 mL) and the organic phases were combined, passed through a phase separating filter paper and the solvent was removed in vacuo. The crude product was purified by flash silica chromatography, elution gradient 0 to 50% EtOAc in heptane. Pure fractions were evaporated to dryness to afford the title compound (8.70 g, 75%) as a beige foam.

¹H NMR (400 MHz, DMSO-d6, 27° C.) −0.07 (9H, s), 0.82 (2H, ddd), 1.42 (9H, s), 3.25 (3H, s), 3.46-3.54 (2H, m), 3.67 (2H, s), 4.92 (1H, d), 5.06 (1H, d), 5.52 (1H, d), 5.61 (1H, d), 6.57 (1H, s), 7.48-7.57 (1H, m), 7.64 (1H, dd), 7.68 (1H, dd), 8.00 (1H, d), 9.16 (1H, s), 9.25 (1H, s); m/z MH⁺ 645

General Method A

Example 1: (S)-2-((5-Amino-6-fluoro-1H-pyrrolo[3,2-b]pyridin-2-yl)methyl)-5-fluoro-1'-(4-fluorobenzyl)spiro[isoindoline-1,3'-pyrrolidine]-2',3-dione Step 1; (S)-5-Fluoro-1'-(4-fluorobenzyl)-2-(4-methoxybenzyl)spiro[isoindoline-1,3'-pyrrolidine]-2',3-dione

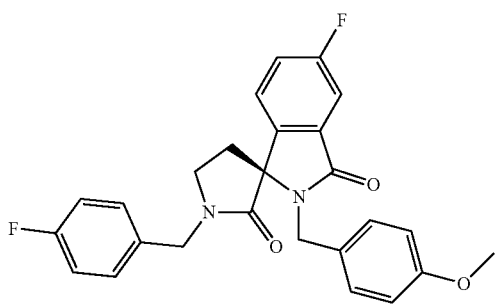 [SMILES: COc1ccc(CN2C(=O)c3cc(F)ccc3[C@]23CCN(Cc2ccc(F)cc2)C3=O)cc1]

Methyl (S)-5-fluoro-2-(4-methoxybenzyl)-3-oxo-1-(2-oxoethyl)isoindoline-1-carboxylate (45 g, 121.2 mmol) and 4-fluorobenzylamine (22.75 g, 181.8 mmol) were placed in a flask with 1,2-dichloroethane (600 mL) and stirred for 1 hour. The reaction mixture was placed in an ice bath and acetic acid (13.87 mL, 242.4 mmol) was added followed by sodium triacetoxyborohydride (51.4 g, 242.4 mmol). The reaction mixture was stirred at rt for 18 hours. The reaction mixture was neutralised with 2M NaOH, diluted with water (200 mL), and extracted with DCM (2×200 mL). The combined organic phases were passed through a phase separating filter paper and the solvent was removed in vacuo to afford the title compound as a pale yellow oil. Used crude in the next reaction assuming 100% yield. m/z MH+ 449

Step 2; (S)-5-Fluoro-1'-(4-fluorobenzyl)spiro[isoindoline-1,3'-pyrrolidine]-2',3-dione

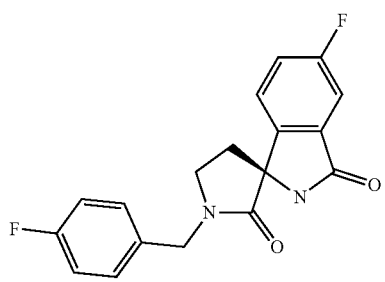 [SMILES: O=C1N[C@@]2(CCN(Cc3ccc(F)cc3)C2=O)c2ccc(F)cc21]

(S)-5-Fluoro-1'-(4-fluorobenzyl)-2-(4-methoxybenzyl)spiro[isoindoline-1,3'-pyrrolidine]-2',3-dione (54.30 g, 121.08 mmol) was placed in a flask with MeCN (500 mL) and water (250 mL). Ammonium cerium(IV) nitrate (199.0 g, 363.2 mmol) was added and the reaction mixture was stirred at rt for 1 hour. The reaction mixture was partitioned between DCM (500 mL) and water (500 mL). The organic phase was washed with water (200 mL) and brine (200 mL), passed through a phase separating filter paper and the solvent was removed in vacuo. The crude product was purified by flash silica chromatography, elution gradient 0 to 100% (10% MeOH in EtOAc) in heptane. Pure fractions were evaporated to dryness to afford the title compound (30.50 g, 77%) as a cream solid.

¹H NMR (400 MHz, DMSO-d6, 30° C.) 2.37-2.44 (1H, m), 2.45-2.49 (1H, m), 3.48 (1H, ddd), 3.60 (1H, dt), 4.49 (2H, s), 7.19-7.25 (2H, m), 7.32-7.37 (2H, m), 7.46 (3H, d), 9.11 (1H, s); m/z MH+ 329

Step 3; (S)-2-((5-Chloro-6-fluoro-1-((2-(trimethylsilyl)ethoxy)methyl)-1H-pyrrolo[3,2-b]pyridin-2-yl)methyl)-5-fluoro-1'-(4-fluorobenzyl)spiro[isoindoline-1,3'-pyrrolidine]-2',3-dione

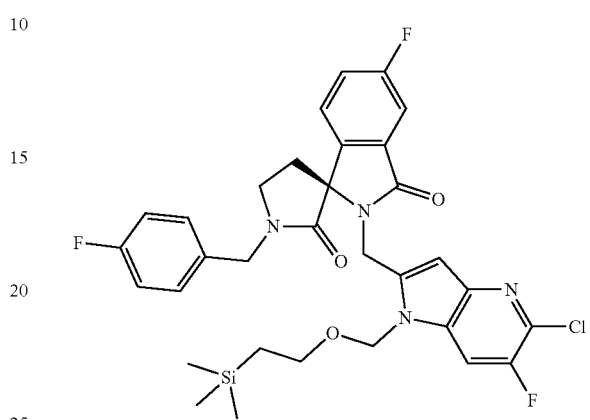

(S)-5-Fluoro-1'-(4-fluorobenzyl)spiro[isoindoline-1,3'-pyrrolidine]-2',3-dione (27 g, 82.24 mmol) and 5-chloro-2-(chloromethyl)-6-fluoro-1-((2-(trimethylsilyl)ethoxy)methyl)-1H-pyrrolo[3,2-b]pyridine (30.20 g, 86.35 mmol) were placed in a flask with dry DMF (120 mL). Caesium carbonate (67.00 g, 205.6 mmol) was added and the reaction mixture was stirred at 50° C. for 1 hour. The reaction mixture was partitioned between water (500 mL) and EtOAc (500 mL) and the aqueous phase was re-extracted with EtOAc (250 mL). The organic phases were combined, washed with water (3×250 mL), brine (200 mL), passed through a phase separating filter paper and the solvent was removed in vacuo. The residue was triturated with diethyl ether (200 mL) and the resulting solid was filtered, washed with ether and dried to afford the title compound (42.20 g, 80%) as a cream solid.

¹H NMR (400 MHz, DMSO-d6, 30° C.) −0.13 (9H, s), 0.55-0.80 (2H, m), 2.32-2.41 (1H, m), 2.52 (1H, d), 3.30-3.38 (1H, m), 3.41-3.51 (2H, m), 3.57-3.69 (1H, m), 4.22-4.36 (2H, m), 4.75 (1H, d), 5.11 (1H, d), 5.53 (1H, d), 5.61 (1H, d), 6.53 (1H, s), 7.13-7.23 (4H, m), 7.45-7.54 (2H, m), 7.57-7.64 (1H, m), 8.28 (1H, dd); m/z MH+ 641

Step 4; (S)-2-((5-((Diphenylmethylene)amino)-6-fluoro-1-((2-(trimethylsilyl)ethoxy)methyl)-1H-pyrrolo[3,2-b]pyridin-2-yl)methyl)-5-fluoro-1'-(4-fluorobenzyl)spiro[isoindoline-1,3'-pyrrolidine]-2',3-dione

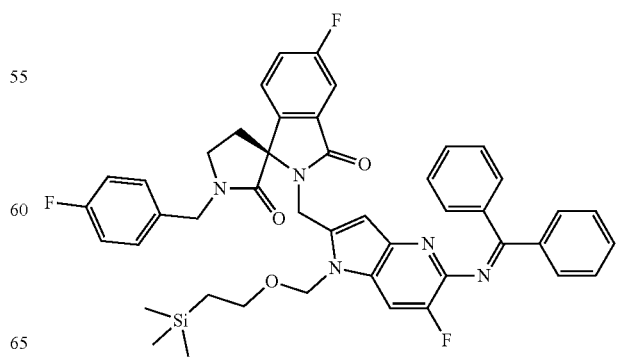

(S)-2-((5-Chloro-6-fluoro-1-((2-(trimethylsilyl)ethoxy)methyl)-1H-pyrrolo[3,2-b]pyridin-2-yl)methyl)-5-fluoro-1'-(4-fluorobenzyl)spiro[isoindoline-1,3'-pyrrolidine]-2',3-dione (41.80 g, 65.19 mmol), diphenylmethanimine (14.18 g, 78.23 mmol) and sodium 2-methylpropan-2-olate (12.53 g, 130.4 mmol) were placed in a flask with toluene (300 mL) and the reaction mixture was degassed by bubbling nitrogen through the mixture for 10 minutes. tBuXPhos (2.77 g, 6.52 mmol) and tris(dibenzylideneacetone)dipalladium(0) (2.99 g, 3.26 mmol) were added and the reaction mixture was then stirred at 65° C. for 30 minutes. The reaction mixture was allowed to cool and partitioned between EtOAc (600 mL) and water (600 mL). The organic phase was washed with brine (200 mL), passed through a phase separating filter paper and the solvent was removed in vacuo. The crude product was purified by flash silica chromatography, elution gradient 0 to 100% EtOAc in heptane. Pure fractions were evaporated to dryness to afford the title compound (49.50 g, 97%) as a yellow solid.

$^1$H NMR (400 MHz, DMSO-d6, 30° C.) −0.15 (9H, s), 0.57-0.76 (2H, m), 2.29-2.39 (1H, m), 2.39-2.48 (1H, m), 3.26-3.29 (1H, m), 3.34-3.45 (2H, m), 3.53-3.66 (1H, m), 4.24 (2H, s), 4.67 (1H, d), 5.04 (1H, d), 5.44 (2H, q), 6.32 (1H, s), 7.11 (2H, dd), 7.17-7.26 (7H, m), 7.43-7.54 (4H, m), 7.55-7.61 (2H, m), 7.68-7.76 (2H, m), 7.81 (1H, d); m/z MH$^+$ 786

Step 5; (S)-2-((5-Amino-6-fluoro-1H-pyrrolo[3,2-b]pyridin-2-yl)methyl)-5-fluoro-1'-(4-fluorobenzyl)spiro[isoindoline-1,3'-pyrrolidine]-2',3-dione

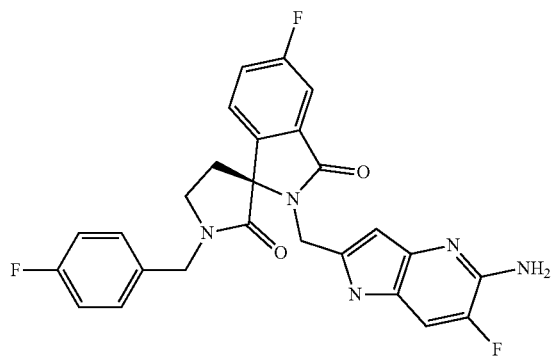 [SMILES: Nc1nc2cc(CN3C(=O)c4cc(F)ccc4[C@]34CCN(Cc3ccc(F)cc3)C4=O)[nH]c2cc1F]

(S)-2-((5-((Diphenylmethylene)amino)-6-fluoro-1-((2-(trimethylsilyl)ethoxy)methyl)-1H-pyrrolo[3,2-b]pyridin-2-yl)methyl)-5-fluoro-1'-(4-fluorobenzyl)spiro[isoindoline-1,3.-pyrrolidine]-2',3-dione (49.50 g, 62.98 mmol) was placed in a flask with 2,2,2-trifluoroacetic acid (96 mL, 1259.63 mmol). 0.50 mL of water was added and the reaction mixture was stirred at 40° C. for 4 hours. The 2,2,2-trifluoroacetic acid was removed in vacuo and the residue was dissolved in MeCN (75 mL). Ammonium hydroxide (28-30% in water) (73.60 mL, 1889.45 mmol) was added and the reaction mixture was stirred at 40° C. for 4 hours and then at rt overnight The resulting solid was filtered off and washed with MeCN (100 mL) to afford ~20 g of the desired compound. The filtrate was reduced to ~200 mL and purified by reverse phase chromatography (Interchim C18-HP Flash column, 2×415 g, 100 mL loading of solution/run), using decreasingly polar mixtures of water (containing by volume 1% NH$_4$OH (28-30% in H$_2$O)) and MeCN as eluents (30-60% gradient). Fractions containing the desired compound were combined and the previous solid (~20 g) obtained was added. The slurry was stirred for 1 hour and then the MeCN was removed in vacuo resulting in the formation of a pale yellow precipitate. The solid was filtered off and dried under vacuum for 2 hours. The solid was then suspended in MeCN (150 mL) and the slurry was gently refluxed for 2 hours before allowing to cool overnight. The solid was filtered off and dried under vacuum to afford the title compound (19.54 g, 63%) as a cream crystalline solid.

$^1$H NMR (400 MHz, DMSO-d6, 30° C.) 2.34-2.40 (2H, m), 3.36 (1H, ddd), 3.60 (1H, dt), 4.29 (1H, d), 4.39-4.52 (2H, m), 5.03 (1H, d), 5.48 (2H, s), 6.02 (1H, d), 7.18-7.27 (2H, m), 7.27-7.39 (3H, m), 7.46-7.55 (2H, m), 7.59 (1H, ddd), 10.69 (1H, d); m/z MH$^+$ 492

General Method B

Example 2: (S)-2-((5-Amino-6-fluoro-1H-pyrrolo[3,2-b]pyridin-2-yl)methyl)-1'-(but-2-yn-1-yl)-5-fluorospiro[isoindoline-1,3'-pyrrolidine]-2',3-dione Step 1; tert-Butyl (S)-(2-((1'-(but-2-yn-1-yl)-5-fluoro-2',3-dioxospiro[isoindoline-1,3'-pyrrolidin]-2-yl)methyl)-6-fluoro-1-((2-(trimethylsilyl)ethoxy)methyl)-1H-pyrrolo[3,2-b]pyridin-5-yl)carbamate

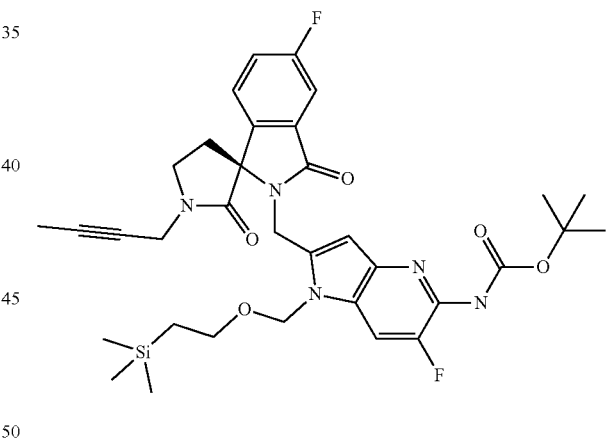

Methyl (S)-2-((5-((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate (9.50 g, 14.73 mmol) and but-2-yn-1-amine hydrochloride (2.33 g, 22.10 mmol) were placed in a flask with 1,2-dichloroethane (100 mL). Triethylamine (3.08 mL, 22.10 mmol) was added and the reaction mixture was stirred at rt for 30 minutes. Sodium triacetoxyborohydride (6.25 g, 29.47 mmol) was added and the reaction mixture was stirred at rt overnight. The reaction mixture was diluted with DCM (250 mL) and washed with saturated NaHCO$_3$ (100 mL), water (100 mL) and brine (100 mL). The organic phase was passed through a phase separating filter paper and the solvent was removed in vacuo to afford the title compound. The crude compound was used without further purification in the next reaction assuming 100% yield. m/z MH$^+$ 666.

Step 2; (S)-2-((5-Amino-6-fluoro-1H-pyrrolo[3,2-b]pyridin-2-yl)methyl)-1'-(but-2-yn-1-yl)-5-fluorospiro[isoindoline-1,3'-pyrrolidine]-2',3-dione

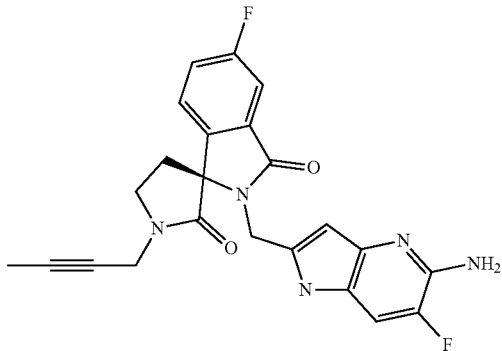 [SMILES: CC#CCN1CC[C@@]2(C1=O)c1ccc(F)cc1C(=O)N2Cc1cc2nc(N)c(F)cc2[nH]1]

tert-Butyl (S)-(2-((1'-(but-2-yn-1-yl)-5-fluoro-2',3-dioxospiro[isoindoline-1,3.-pyrrolidin]-2-yl)methyl)-6-fluoro-1-((2-(trimethylsilyl)ethoxy)methyl)-1H-pyrrolo[3,2-b]pyridin-5-yl)carbamate (9.81 g, 14.73 mmol) was placed in a flask with 2,2,2-trifluoroacetic acid (22.55 mL, 294.7 mmol) and the solution was stirred for 2 hours at rt. The 2,2,2-trifluoroacetic acid was removed in vacuo and the residue was dissolved in MeCN (20 mL). Ammonium hydroxide (28-30% in water) (22.95 mL, 589.4 mmol) was added and the reaction mixture was stirred at 40° C. for 2 hours. The crude product was purified by reverse phase chromatography (Interchim C18-HP Flash column, 415 g), using decreasingly polar mixtures of water (containing by volume 1% NH$_4$OH (28-30% in H$_2$O)) and MeCN as eluents (30-60% gradient). Fractions containing the desired compound were combined, the MeCN was removed in vacuo and the resulting solid was filtered off and dried to afford the title compound (3.74 g, 58%) as a cream crystalline solid.

$^1$H NMR (400 MHz, DMSO-d6, 27° C.) 1.88 (3H, t), 2.36-2.44 (2H, m), 3.54 (1H, ddd), 3.76 (1H, dt), 4.08 (2H, qq), 4.24 (1H, d), 5.03 (1H, d), 5.49 (2H, s), 6.11 (1H, d), 7.36 (1H, dd), 7.49-7.64 (3H, m), 10.69 (1H, d); m/z MH$^+$ 436

General Method C

Example 3: (S)-2-((5-Amino-6-fluoro-1H-pyrrolo[3,2-b]pyridin-2-yl)methyl)-5-fluoro-1'-(prop-2-yn-1-yl)spiro[isoindoline-1,3'-pyrrolidine]-2',3-dione Step 1; tert-Butyl (S)-(6-fluoro-2-((5-fluoro-2',3-dioxo-1'-(prop-2-yn-1-yl)spiro[isoindoline-1,3'-pyrrolidin]-2-yl)methyl)-1-((2-(trimethylsilyl)ethoxy)methyl)-1H-pyrrolo[3,2-b]pyridin-5-yl)carbamate

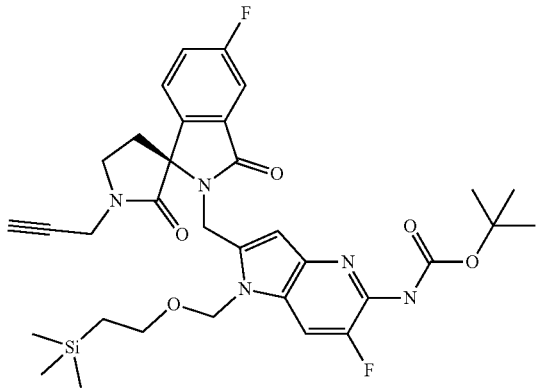 [SMILES: C#CCN1CC[C@@]2(C1=O)c1ccc(F)cc1C(=O)N2Cc1cc2nc(NC(=O)OC(C)(C)C)c(F)cc2n1COCC[Si](C)(C)C]

Prop-2-yn-1-amine (0.10 g, 1.87 mmol) was added to methyl (S)-2-((5-((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate (0.40 g, 0.62 mmol) in 1,2-dichloroethane (5 mL) and stirred at rt for 1 hour. Sodium triacetoxyborohydride (0.40 g, 1.87 mmol) was then added and the reaction mixture was stirred at rt for 16 hours. The reaction mixture was quenched with water (20 mL) and extracted with EtOAc (3×25 mL). The combined organics were dried over Na$_2$SO$_4$, filtered and the solvent was removed in vacuo. The crude product was purified by flash silica chromatography, elution gradient 0 to 50% EtOAc in petroleum ether (60-90° C.). Pure fractions were evaporated to dryness to afford the title compound (0.37 g, 90%) as a yellow solid.

$^1$H NMR (400 MHz, DMSO-d6) 0.12 (9H, s), 0.61-0.78 (2H, m), 1.43 (9H, s), 2.36-2.48 (2H, m), 3.37-3.47 (2H, m), 3.48-3.56 (1H, m), 3.78 (1H, q), 3.99 (2H, d), 4.62 (1H, d), 5.17 (1H, d), 5.44-5.63 (2H, m), 5.77 (1H, s), 6.55 (1H, s), 7.43-7.69 (3H, m), 8.03 (1H, d), 9.18 (1H, s); m/z MH$^+$ 652

Step 2; (S)-2-((5-Amino-6-fluoro-1H-pyrrolo[3,2-b]pyridin-2-yl)methyl)-5-fluoro-1'-(prop-2-yn-1-yl)spiro[isoindoline-1,3'-pyrrolidine]-2',3-dione

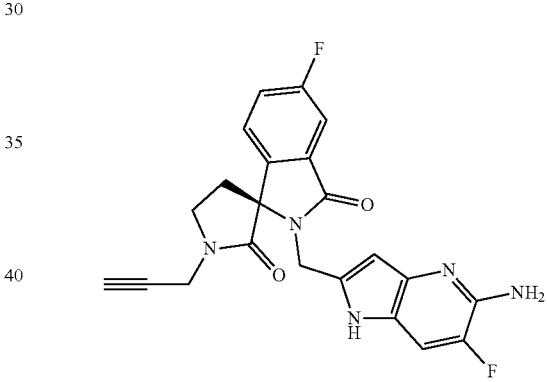

2,2,2-trifluoroacetic acid (3.00 mL) was added to tert-butyl (S)-(6-fluoro-2-((5-fluoro-2',3-dioxo-1'-(prop-2-yn-1-yl)spiro[isoindoline-1,3'-pyrrolidin]-2-yl)methyl)-1-((2-(trimethylsilyl)ethoxy)methyl)-1H-pyrrolo[3,2-b]pyridin-5-yl)carbamate (50 mg, 0.08 mmol) in DCM (3 mL). The reaction mixture was stirred at rt for 1 hour. The solvent was removed in vacuo. The crude product was purified by ion exchange chromatography, using an SCX column. The desired product was eluted from the column using 7M NH$_3$/MeOH and pure fractions were evaporated to dryness to afford crude product. The crude product was purified by flash C18-flash chromatography, elution gradient 0 to 100% MeCN in water (0.1% NH$_4$HCO$_3$). Fractions were evaporated to dryness to afford crude product. The product was further purified by preparative HPLC. Fractions containing the desired compound were evaporated to dryness to afford the title compound (15 mg, 46%) as a white solid.

$^1$H NMR (300 MHz, DMSO-d6) 2.34-2.43 (2H, m), 3.38 (1H, m), 3.47-3.58 (1H, m), 3.70-3.81 (1H, m), 4.07-4.26 (3H, m), 5.00 (1H, d), 5.49 (2H, s), 6.09 (1H, s), 7.29-7.40 (1H, m), 7.45-7.62 (3H, m), 10.68 (1H, s); m/z MH$^+$ 422

General Method D

Example 4: (S)-2-((5-Amino-6-fluoro-1H-pyrrolo[3,2-b]pyridin-2-yl)methyl)-5-fluoro-1'-(3-(1-methyl-1H-pyrazol-4-yl)prop-2-yn-1-yl)spiro[isoindoline-1,3'-pyrrolidine]-2',3-dione

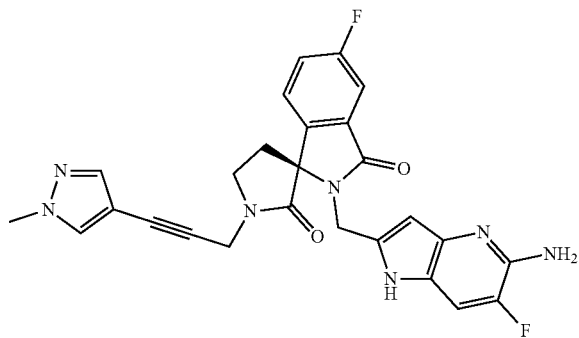 [SMILES: Cn1cc(C#CCN2CC[C@@]3(C2=O)c2ccc(F)cc2C(=O)N3Cc2cc3nc(N)c(F)cc3[nH]2)cn1]

3-(1-Methyl-1H-pyrazol-4-yl)prop-2-yn-1-amine (42 mg, 0.31 mmol) was added to methyl (S)-2-((5-((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate (100 mg, 0.16 mmol) in 1,2-dichloroethane (2 mL) and stirred at rt for 1 hour. Sodium triacetoxyborohydride (66 mg, 0.31 mmol) was added and the reaction mixture was stirred at 40° C. for 16 hours. The reaction mixture was cooled, 2,2,2-trifluoroacetic acid (2.00 mL) was added and the reaction mixture was stirred at rt for 1 hour. The crude product was purified by ion exchange chromatography, using an SCX column. The desired product was eluted from the column using 7M NH$_3$/MeOH and fractions were evaporated to dryness. The product was further purified by preparative HPLC. Fractions containing the desired compound were evaporated to dryness to afford the title compound (30 mg, 38%) as a white solid.

$^1$H NMR (400 MHz, DMSO-d6) 2.35-2.45 (1H, m), 2.51-2.68 (1H, m), 3.52-3.64 (1H, m), 3.82 (4H, d), 4.19-4.41 (3H, m), 5.04 (1H, d), 5.51 (2H, s), 6.10 (1H, d), 7.35 (1H, d), 7.47-7.56 (1H, m), 7.56-7.63 (2H, m), 7.65 (1H, s), 8.04 (1H, s), 10.70 (1H, d); m/z MH$^+$ 502

General Method E

Example 5: (S)-4-((-((5-Amino-6-fluoro-1H-pyrrolo[3,2-b]pyridin-2-yl)methyl)-5-fluoro-2',3-dioxospiro[isoindoline-1,3'-pyrrolidin]-1'-yl)methyl)-2-fluorobenzonitrile

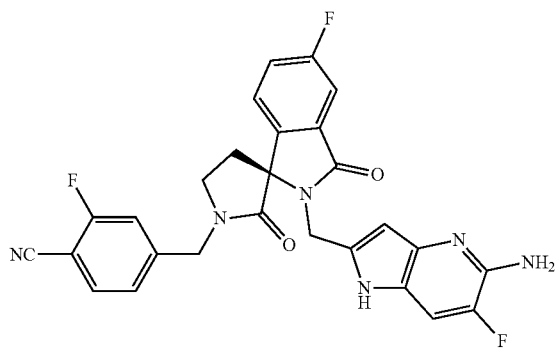 [SMILES: N#Cc1ccc(CN2CC[C@@]3(C2=O)c2ccc(F)cc2C(=O)N3Cc2cc3nc(N)c(F)cc3[nH]2)cc1F]

4-(Aminomethyl)-2-fluorobenzonitrile hydrochloride (58 mg, 0.31 mmol) and sodium acetate (25 mg, 0.31 mmol) were added to methyl (S)-2-((5-((tert--butoxycarbonyl)amino)-6-fluoro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate (100 mg, 0.16 mmol) in 1,2-dichloroethane (1.50 mL) at rt. After 1 hour sodium triacetoxyborohydride (66 mg, 0.31 mmol) was added and the reaction mixture was stirred at rt for 16 hours. 2,2,2-trifluoroacetic acid (1.50 mL) was added and the reaction mixture was stirred at rt for 1 hour. The solvent was removed under reduced pressure and the crude product was purified by ion exchange chromatography, using an SCX column. The desired product was eluted from the column using 7M NH$_3$/MeOH and fractions were evaporated to dryness to afford crude product. The crude product was purified by preparative HPLC. Fractions containing the desired compound were evaporated to dryness to afford the title compound (49 mg, 61%) as a white solid.

$^1$H NMR (400 MHz, DMSO-d6) 2.35-2.50 (2H, m), 3.44 (1H, td), 3.65-3.76 (1H, m), 4.35 (1H, d), 4.53 (1H, d), 4.59 (1H, d), 5.01 (1H, d), 5.51 (2H, s), 6.07 (1H, d), 7.28 (1H, dd), 7.36 (1H, d), 7.44 (1H, dd), 7.52 (1H, td), 7.57-7.65 (2H, m), 7.95 (1H, dd), 10.71 (1H, d); m/z MH$^+$ 517

Example 6: (S)-1'-(3-(2H-1,2,3-Triazol-2-yl)benzyl)-2-((5-amino-6-fluoro-1H-pyrrolo[3,2-b]pyridin-2-yl)methyl)-5-fluorospiro[isoindoline-1,3'-pyrrolidine]-2',3-dione

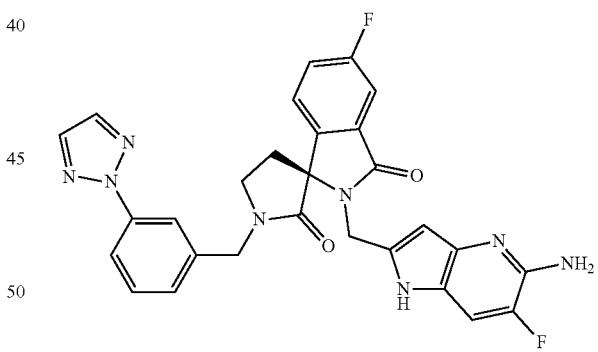

The title compound (27 mg, 32%, white solid) was made according to General method E using methyl (S)-2-((5-((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate and 3-(2H-1,2,3-triazol-2-yl)benzylamine hydrochloride.

$^1$H NMR (400 MHz, DMSO-d6) 2.39 (2H, t), 3.43 (1H, dt), 3.67 (1H, dt), 4.30 (1H, d), 4.55 (1H, d), 4.66 (1H, d), 5.09 (1H, d), 5.51 (2H, s), 6.03 (1H, d), 7.30-7.38 (2H, m), 7.49 (1H, td), 7.54-7.65 (3H, m), 7.95 (1H, t), 8.01 (1H, dt), 8.17 (2H, s), 10.72 (1H, d); m/z MH$^+$ 541

Example 7: (S)-2-((5-Amino-6-fluoro-1H-pyrrolo[3,2-b]pyridin-2-yl)methyl)-1'-(2,5-difluorobenzyl)-5-fluorospiro[isoindoline-1,3'-pyrrolidine]-2',3-dione

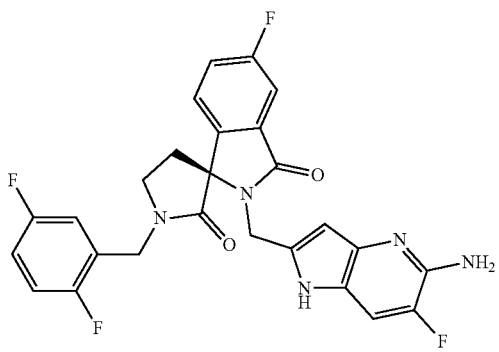 [SMILES: Nc1nc2cc(CN3C(=O)c4cc(F)ccc4[C@]34CCN(Cc3cc(F)ccc3F)C4=O)[nH]c2cc1F]

The title compound (33 mg, 42%, pale yellow solid) was made according to General method D using methyl (S)-2-((5-(((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate and 2,5-difluorobenzylamine.

¹H NMR (400 MHz, DMSO) 2.39 (2H, t), 3.36-3.46 (1H, m), 3.60-3.71 (1H, m), 4.25 (1H, d), 4.47 (1H, d), 4.56 (1H, d), 5.05 (1H, d), 5.51 (2H, s), 6.03 (1H, d), 7.15-7.24 (1H, m), 7.21-7.32 (1H, m), 7.29-7.39 (2H, m), 7.47-7.62 (3H, m), 10.71 (1H, d); m/z MH⁺ 510

Example 8: (S)-2-((5-Amino-6-fluoro-1H-pyrrolo[3,2-b]pyridin-2-yl)methyl)-1'-(2,2-difluoroethyl)-5-fluorospiro[isoindoline-1,3'-pyrrolidine]-2',3-dione Step 1; tert-Butyl (S)-(2-((1'-(2,2-difluoroethyl)-5-fluoro-2',3-dioxospiro[isoindoline-1,3'-pyrrolidin]-2-yl)methyl)-6-fluoro-1-((2-(trimethylsilyl)ethoxy)methyl)-1H-pyrrolo[3,2-b]pyridin-5-yl)carbamate

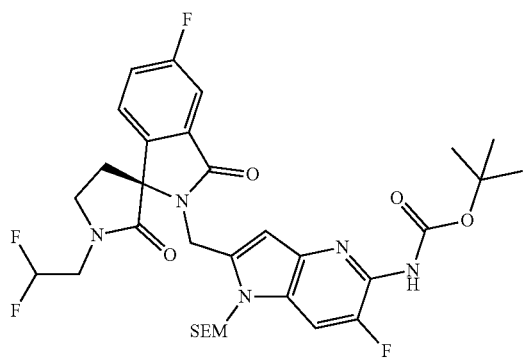 [SMILES: CC(C)(C)OC(=O)Nc1nc2cc(CN3C(=O)c4cc(F)ccc4[C@]34CCN(CC(F)F)C4=O)n(COCC[Si](C)(C)C)c2cc1F]

Sodium triacetoxyborohydride (3.94 g, 18.61 mmol) was added to methyl (S)-2-((5-(((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxo-1-(2-oxoethyl) isoindoline-1-carboxylate (4.00 g, 6.20 mmol) and 2,2-difluoroethan-1-amine (1.01 g, 12.41 mmol) in 1,2-dichloroethane (50 mL) at rt over a period of 1 hour. The reaction mixture was stirred at 40° C. for 1 hour. The reaction mixture was quenched with saturated NH₄Cl (100 mL) and extracted with EtOAc (3×100 mL). The organic phase was dried over MgSO₄, filtered and the solvent was removed in vacuo. The crude product was purified by flash silica chromatography, elution gradient 0 to 100% EtOAc in petroleum ether (60-90° C.). Pure fractions were evaporated to dryness to afford the title compound (4.20 g, 100%) as a yellow solid.

¹H NMR (300 MHz, DMSO-d6, 23° C.) −0.24 (9H, s), 0.50-0.60 (2H, m), 1.30 (9H, s), 2.18-2.36 (2H, m), 3.26-3.42 (3H, m), 3.91 (3H, q), 4.48 (2H, d), 5.06 (2H, d), 5.82-5.90 (1H, m), 7.91 (2H, d), 8.13 (1H, s), 9.07 (2H, s), 11.82 (1H, s); m/z MH⁺ 678

Step 2; (S)-2-((5-Amino-6-fluoro-1H-pyrrolo[3,2-b]pyridin-2-yl)methyl)-1'-(2,2-difluoroethyl)-5-fluorospiro[isoindoline-1,3'-pyrrolidine]-2',3-dione

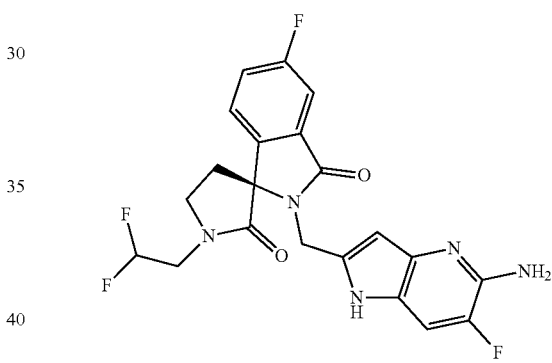

2,2,2-trifluoroacetic acid (30 mL) was added to tert-butyl (S)-(2-((1'-(2,2-difluoroethyl)-5-fluoro-2',3-dioxospiro[isoindoline-1,3'-pyrrolidin]-2-yl)methyl)-6-fluoro-1-((2-(trimethylsilyl)ethoxy)methyl)-1H-pyrrolo[3,2-b]pyridin-5-yl)carbamate (4.00 g, 5.90 mmol) at rt and the reaction mixture was stirred at rt for 1 hour. The 2,2,2-trifluoroacetic acid was removed in vacuo and the crude product was purified by ion exchange chromatography, using an SCX column. The desired product was eluted from the column using 7M NH₃/MeOH and fractions were evaporated to dryness. The crude product was purified by flash C18-flash chromatography, elution gradient 0 to 50% MeCN in water (0.1% NH₄HCO₃). Pure fractions were evaporated to dryness to afford the title compound (2.00 g, 76%) as a yellow solid.

¹H NMR (300 MHz, DMSO-d6) 2.32-2.49 (2H, m), 3.54-3.92 (4H, m), 4.30 (1H, d), 5.02 (1H, d), 5.52 (2H, s), 6.03-6.43 (2H, m), 7.31-7.41 (1H, m), 7.51-7.63 (3H, m), 10.71 (1H, d); m/z MH⁺ 448

Example 9: (S)-2-((5-Amino-6-fluoro-1H-pyrrolo[3,2-b]pyridin-2-yl)methyl)-5-fluoro-1'-((1-(fluoromethyl)cyclopropyl)methyl)spiro[isoindoline-1,3'-pyrrolidine]-2',3-dione

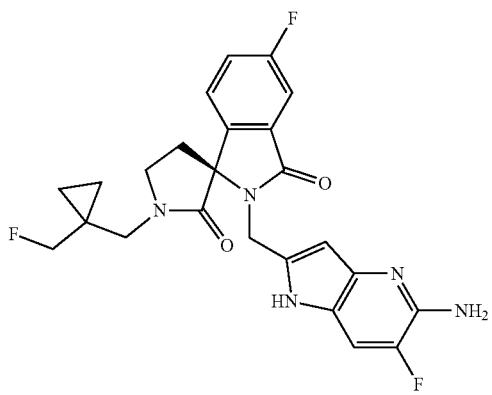 [SMILES: Nc1nc2cc(CN3C(=O)c4cc(F)ccc4[C@]34CCN(CC3(CF)CC3)C4=O)[nH]c2cc1F]

The title compound (70 mg, 17%, yellow solid) was made according to General method C using methyl (S)-2-((5-((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate and (1-(fluoromethyl)cyclopropyl)methanamine hydrochloride.

$^1$H NMR (300 MHz, DMSO-d6, 23° C.) 0.65 (4H, s), 2.41 (2H, t), 3.12-3.23 (1H, m), 3.47 (1H, d), 3.55 (1H, s), 3.81 (1H, t), 4.07-4.40 (3H, m), 5.02 (1H, d), 5.52 (2H, s), 6.08 (1H, s), 7.36 (1H, d), 7.46-7.67 (3H, m), 10.70 (1H, s); m/z MH$^+$ 470

Example 10: (S)-2-((5-Amino-6-fluoro-1H-pyrrolo[3,2-b]pyridin-2-yl)methyl)-5-fluoro-1'-methylspiro[isoindoline-1,3'-pyrrolidine]-2',3-dione Step 1; rac-6-Fluoro-2-[(4-methoxyphenyl)methyl]-1'-methyl-spiro[isoindoline-3,3'-pyrrolidine]-1,2'-dione

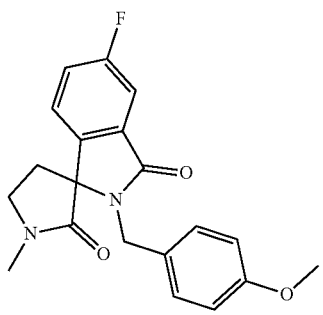 [SMILES: COc1ccc(CN2C(=O)c3cc(F)ccc3C23CCN(C)C3=O)cc1]

Sodium acetate (19.88 g, 242.4 mmol) was added in one portion to rac-methyl 5-fluoro-2-[(4-methoxyphenyl)methyl]-3-oxo-1-(2-oxoethyl)isoindoline-1-carboxylate (30.00 g, 80.78 mmol) and methylamine hydrochloride (16.36 g, 242.4 mmol) in 1,2-dichloroethane (400 mL) at rt. After 1 hour sodium triacetoxyborohydride (51.40 g, 242.4 mmol) was added and the reaction mixture was stirred at rt for 16 hours. The reaction mixture was poured into saturated NaHCO$_3$ (1 L) and extracted with DCM (3×750 mL). The organic phase was dried over Na$_2$SO$_4$, filtered and the solvent was removed in vacuo. The crude product was purified by flash silica chromatography, elution gradient 0 to 60% EtOAc in petroleum ether (60-90° C.). Pure fractions were evaporated to dryness to afford the title compound (10.00 g, 35%) as a white solid.

$^1$H NMR (300 MHz, DMSO-d6) 2.29-2.40 (2H, m), 2.72-2.86 (3H, m), 3.28-3.36 (2H, m), 3.72 (3H, d), 4.20 (1H, d), 4.80 (1H, d), 6.78-6.91 (2H, m), 7.18-7.31 (2H, m), 7.43-7.58 (2H, m), 7.60-7.67 (1H, m); m/z MH$^+$ 355

Step 2; (S)-5-Fluoro-1'-methylspiro[isoindoline-1,3'-pyrrolidine]-2',3-dione

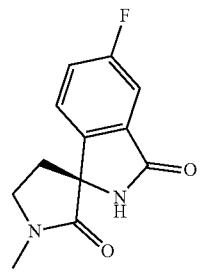 [SMILES: CN1CC[C@@]2(NC(=O)c3cc(F)ccc32)C1=O]

Ceric ammonium nitrate (30.90 g, 56.44 mmol) was added to rac-6-fluoro-2-[(4-methoxyphenyl)methyl]-1'-methyl-spiro[isoindoline-3,3'-pyrrolidine]-1,2'-dione (10.00 g, 28.22 mmol) in MeCN (80 mL) and water (40 mL) at rt. The reaction mixture was stirred at rt for 16 hours. The reaction mixture was poured into water (250 mL) and extracted with EtOAc (250 mL). The organic phase was dried over MgSO$_4$, filtered and the solvent was removed in vacuo. The crude product was purified by flash silica chromatography, elution gradient 0 to 10% MeOH in DCM. Pure fractions were evaporated to dryness to afford the title compound (5.60 g, 85%) as a yellow oil. The enantiomeric mixture was purified by chiral HPLC, Column: CHIRAL ART Cellulose-SB, 4.6*100 mm,3.0 um; Mobile Phase A:, Mobile Phase B:MEOH(0.1% DEA); Flow rate:2 mL/min; Gradient:10% B; 220 nm. The fractions containing the desired compound were evaporated to dryness to afford the title compound (2.90 g, 52%) as a yellow solid.

(Presumed stereochemical assignment of this intermediate based on biological activity of bioactive compounds made using this enantiomer of the intermediate (compared to those made using the other enantiomer), together with Xray structural evidence that the S enantiomer is preferred and more active than the R enantiomer).

$^1$H NMR (300 MHz, DMSO-d6) 2.29-2.51 (2H, m), 2.87 (3H, s), 3.47-3.60 (1H, m), 3.64-3.78 (1H, m), 7.38-7.51 (2H, m), 7.53-7.64 (1H, m), 9.03 (1H, s); m/z MH$^+$ 235

Step 3; (S)-2-((5-Chloro-6-fluoro-1-((2-(trimethylsilyl)ethoxy)methyl)-1H-pyrrolo[3,2-b]pyridin-2-yl)methyl)-5-fluoro-1'-methylspiro[isoindoline-1,3'-pyrrolidine]-2',3-dione

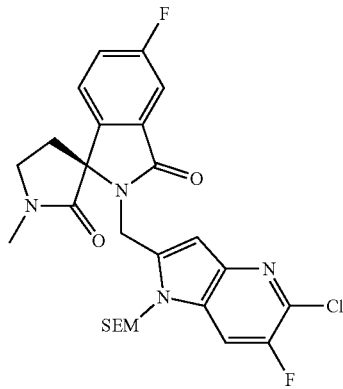 [SMILES: CN1CC[C@@]2(C1=O)c1ccc(F)cc1C(=O)N2Cc1cc2nc(Cl)c(F)cc2n1COCC[Si](C)(C)C]

Sodium hydride (60% in mineral oil) (0.13 g, 3.30 mmol) was added to (S)-5-fluoro-1'-methylspiro[isoindoline-1,3'-pyrrolidine]-2',3-dione (0.595 g, 2.54 mmol) in DMF (15 mL) at 0° C. After 1 hour 2-(bromomethyl)-5-chloro-6-fluoro-1-((2-(trimethylsilyl)ethoxy)methyl)-1H-pyrrolo[3,2-b]pyridine (1.00 g, 2.54 mmol) was added and the reaction mixture was stirred at rt for 2 hours. The reaction mixture was quenched with saturated NH$_4$Cl (100 mL) and extracted with EtOAc (100 mL). The organic phase was dried over Na$_2$SO$_4$, filtered and the solvent was removed in vacuo. The crude product was purified by flash silica chromatography, elution gradient 0 to 40% EtOAc in petroleum ether (60-90° C.). Pure fractions were evaporated to dryness to afford the title compound (1.18 g, 85%) as a yellow oil.

$^1$H NMR (300 MHz, DMSO-d6) −0.11 (9H, d), 0.65-0.85 (2H, m), 2.32-2.45 (1H, m), 2.63 (3H, s), 2.89 (1H, s), 3.36-3.53 (3H, m), 3.66-3.81 (1H, m), 4.75 (1H, d), 5.07 (1H, d), 5.52 (1H, d), 5.56-5.69 (1H, m), 6.64 (1H, s), 7.44-7.56 (1H, m), 7.53-7.68 (2H, m), 8.28 (1H, d); m/z MH$^+$ 547

Step 4; (S)-2-((5-((Diphenylmethylene)amino)-6-fluoro-1-((2-(trimethylsilyl)ethoxy)methyl)-1H-pyrrolo[3,2-b]pyridin-2-yl)methyl)-5-fluoro-1'-methylspiro[isoindoline-1,3'-pyrrolidine]-2',3-dione

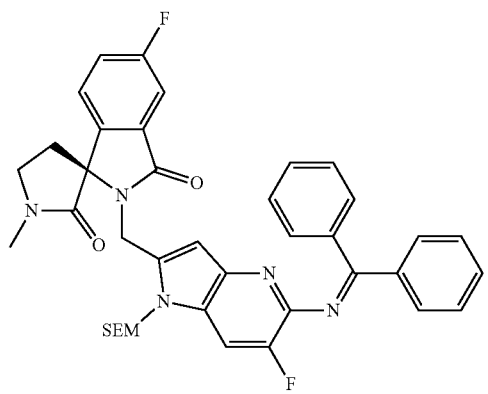 [SMILES: CN1CC[C@@]2(C1=O)c1ccc(F)cc1C(=O)N2Cc1cc2nc(N=C(c3ccccc3)c3ccccc3)c(F)cc2n1COCC[Si](C)(C)C]

Tris(dibenzylideneacetone)dipalladium(0) (0.092 g, 0.10 mmol) was added to (S)-2-((5-chloro-6-fluoro-1-((2-(trimethylsilyl)ethoxy)methyl)-1H-pyrrolo[3,2-b]pyridin-2-yl)methyl)-5-fluoro-1'-methylspiro[isoindoline-1,3'-pyrrolidine]-2',3-dione (1.10 g, 2.01 mmol), diphenylmethanimine (0.44 g, 2.41 mmol), sodium t-butoxide (0.39 g, 4.02 mmol) and 2-di-t-butylphosphino-2',4',6'-tri-i-propyl-1,1'-biphenyl (0.085 g, 0.20 mmol) in toluene (15 mL) under nitrogen at rt. The reaction mixture was stirred at 60° C. for 2 hours. The reaction mixture was cooled and the solvent was removed in vacuo. The crude product was purified by flash silica chromatography, elution gradient 0 to 100% EtOAc in petroleum ether (60-90° C.). Pure fractions were evaporated to dryness to afford the title compound (1.26 g, 91%) as a white solid.

$^1$H NMR (300 MHz, DMSO-d6) −0.12 (9H, s), 0.63-0.80 (2H, m), 2.43 (3H, s), 2.51 (2H, s), 3.34 (3H, s), 3.62-3.76 (1H, m), 4.80 (1H, d), 4.94 (1H, d), 5.36 (1H, d), 5.45 (1H, d), 6.46 (1H, s), 7.08-7.18 (2H, m), 7.21-7.32 (3H, m), 7.43-7.66 (6H, m), 7.66-7.76 (2H, m), 7.83 (1H, d); m/z MH$^+$ 692

Step 5; (S)-2-((5-Amino-6-fluoro-1H-pyrrolo[3,2-b]pyridin-2-yl)methyl)-5-fluoro-1'-methylspiro[isoindoline-1,3'-pyrrolidine]-2',3-dione

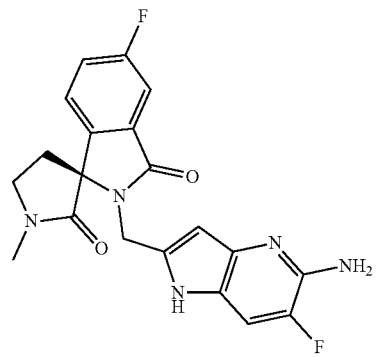 [SMILES: CN1CC[C@@]2(C1=O)c1ccc(F)cc1C(=O)N2Cc1cc2nc(N)c(F)cc2[nH]1]

2,2,2-trifluoroacetic acid (20 mL) was added to (S)-2-((5-((diphenylmethylene)amino)-6-fluoro-1-((2-(trimethylsilyl)ethoxy)methyl)-1H-pyrrolo[3,2-b]pyridin-2-yl)methyl)-5-fluoro-1'-methylspiro[isoindoline-1,3'-pyrrolidine]-2',3-dione (1.20 g, 1.73 mmol) at rt. The reaction mixture was stirred at rt for 1 hour. The solvent was removed in vacuo and the residue was basified with NaHCO$_3$. The reaction mixture was diluted with EtOAc (50 mL), and washed sequentially with water (2×50 mL). The organic phase was dried over Na$_2$SO$_4$, filtered and solvent was removed in vacuo. The crude product was purified by preparative HPLC. Fractions containing the desired compound were evaporated to dryness to afford the title compound (30 mg, 44%) as a white solid.

$^1$H NMR (300 MHz, DMSO-d6) 2.32-2.47 (2H, m), 2.84 (3H, s), 3.40-3.54 (1H, m), 3.66-3.81 (1H, m), 4.30 (1H, d), 4.97 (1H, d), 5.58 (2H, s), 6.12 (1H, d), 7.39 (1H, d), 7.46-7.59 (2H, m), 7.64-7.71 (1H, m), 10.71 (1H, s); m/z MH$^+$ 398

Example 11: (S)-2-((5-Amino-6-fluoro-1H-pyrrolo[3,2-b]pyridin-2-yl)methyl)-1'-(2-(difluoromethoxy)ethyl)-5-fluorospiro[isoindoline-1,3'-pyrrolidine]-2',3-dione

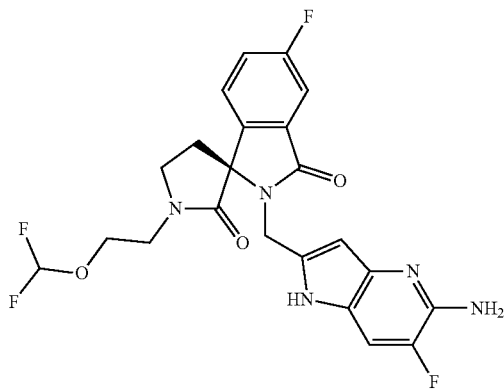 [SMILES: Nc1nc2cc(CN3C(=O)c4cc(F)ccc4[C@]34CCN(CCOC(F)F)C4=O)[nH]c2cc1F]

The title compound (14 mg, 38%, cream solid) was made according to General method B using methyl (S)-2-((5-((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate and 2-(difluoromethoxy)ethan-1-amine hydrochloride.

$^1$H NMR (400 MHz, DMSO-d6, 27° C.) 2.36-2.45 (2H, m), 3.44-3.66 (3H, m), 3.75-3.85 (1H, m), 3.94-4.08 (2H, m), 4.27 (1H, d), 5.01 (1H, d), 5.49 (2H, s), 6.10 (1H, d), 6.75 (1H, t), 7.36 (1H, d), 7.51 (1H, td), 7.55-7.62 (2H, m), 10.67 (1H, s); m/z MH$^+$ 478

Example 12: (S)-2-((5-Amino-6-fluoro-1H-pyrrolo[3,2-b]pyridin-2-yl)methyl)-5-fluoro-1'-((3-fluoropyridin-2-yl)methyl)spiro[isoindoline-1,3'-pyrrolidine]-2',3-dione

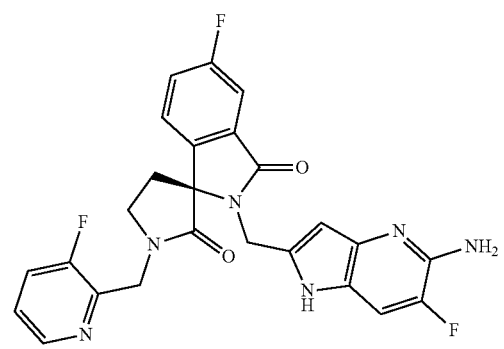 [SMILES: Nc1nc2cc(CN3C(=O)c4cc(F)ccc4[C@]34CCN(Cc3ncccc3F)C4=O)[nH]c2cc1F]

The title compound (16 mg, 40%, yellow solid) was made according to General method C using methyl (S)-2-((5-((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate and (3-fluoropyridin-2-yl)methanamine hydrochloride.

$^1$H NMR (300 MHz, DMSO-d6, 22° C.) 2.38 (2H, t), 3.43-3.56 (1H, m), 3.77 (1H, q), 4.36 (1H, d), 4.6-4.81 (2H, m), 5.06 (1H, d), 5.49 (2H, s), 6.04-6.11 (1H, m), 7.34 (1H, d), 7.48-7.61 (3H, m), 7.70-7.83 (2H, m), 8.44-8.53 (1H, m), 10.69 (1H, d); m/z MH$^+$ 493

Example 13: (S)-2-((5-Amino-6-fluoro-1H-pyrrolo[3,2-b]pyridin-2-yl)methyl)-5-fluoro-1'-(isoxazol-5-ylmethyl)spiro[isoindoline-1,3'-pyrrolidine]-2',3-dione

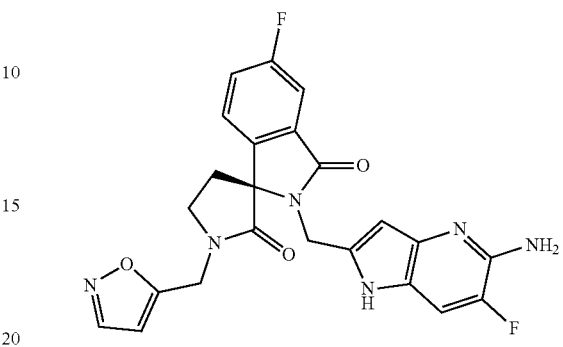

The title compound (23 mg, 40%, white solid) was made according to General method D using methyl (S)-2-((5-((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate and isoxazol-5-ylmethanamine hydrochloride.

$^1$H NMR (300 MHz, DMSO-d6) 2.39-2.47 (2H, m), 3.50 (1H, d), 3.67-3.81 (1H, m), 4.27 (1H, d), 4.59-4.79 (2H, m), 5.02 (1H, d), 5.50 (2H, s), 6.06 (1H, s), 6.51 (1H, d), 7.30-7.40 (1H, m), 7.46-7.64 (3H, m), 8.59 (1H, d), 10.70 (1H, s); m/z MH$^+$ 465

Example 14: (S)-2-((5-Amino-6-fluoro-1H-pyrrolo[3,2-b]pyridin-2-yl)methyl)-5-fluoro-1'-((5-(trifluoromethyl)pyridazin-3-yl)methyl)spiro[isoindoline-1,3'-pyrrolidine]-2',3-dione

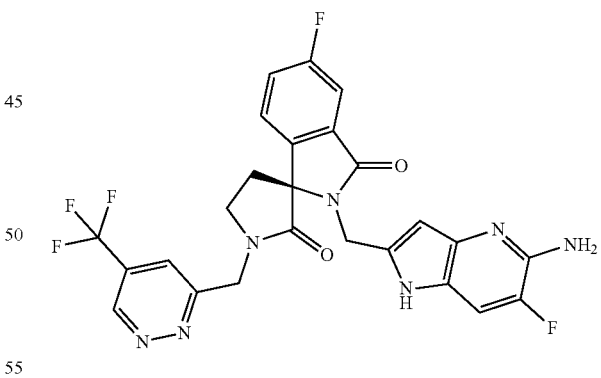

The title compound (19 mg, 23%, white solid) was made according to General method D using methyl (S)-2-((5-((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate and (5-(trifluoromethyl)pyridazin-3-yl)methanamine.

$^1$H NMR (400 MHz, DMSO-d6) 2.44 (2H, d), 3.56-3.66 (1H, m), 3.82-3.93 (1H, m), 4.41 (1H, d), 4.87-5.13 (3H, m), 5.49 (2H, s), 6.17 (1H, d), 7.35 (1H, d), 7.48-7.56 (1H, m), 7.56-7.63 (1H, m), 7.72-7.80 (1H, m), 8.12 (1H, t), 9.70 (1H, d), 10.68 (1H, d); m/z MH$^+$ 544

Example 15: (S)-2-((5-Amino-6-fluoro-1H-pyrrolo[3,2-b]pyridin-2-yl)methyl)-5-fluoro-1'-((1-methyl-1H-indazol-5-yl)methyl)spiro[isoindoline-1,3'-pyrrolidine]-2',3-dione

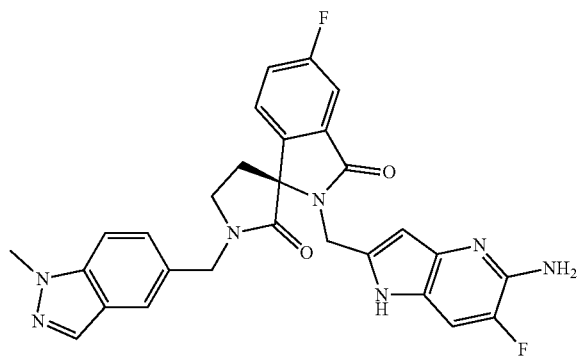 [SMILES: Cn1ncc2cc(CN3CC[C@@]4(C3=O)c3ccc(F)cc3C(=O)N4Cc3cc4nc(N)c(F)cc4[nH]3)ccc21]

The title compound (42 mg, 51%, white solid) was made according to General method D using methyl (S)-2-((5-((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate and (1-methyl-1H-indazol-5-yl)methanamine.

$^1$H NMR (300 MHz, DMSO-d6) 2.35 (2H, t), 3.33 (1H, s), 3.51—3.65 (1H, m), 4.07 (3H, s), 4.30 (1H, d), 4.47-4.66 (2H, m), 5.05 (1H, d), 5.51 (2H, s), 6.02 (1H, d), 7.20-7.29 (1H, m), 7.35 (1H, d), 7.40-7.60 (2H, m), 7.56-7.71 (3H, m), 8.08 (1H, s), 10.71 (1H, s); m/z MH$^+$ 528

Example 16: (S)-2-((5-Amino-6-fluoro-1H-pyrrolo[3,2-b]pyridin-2-yl)methyl)-1'-(benzo[d]oxazol-2-ylmethyl)-5-fluorospiro[isoindoline-1,3'-pyrrolidine]-2',3-dione

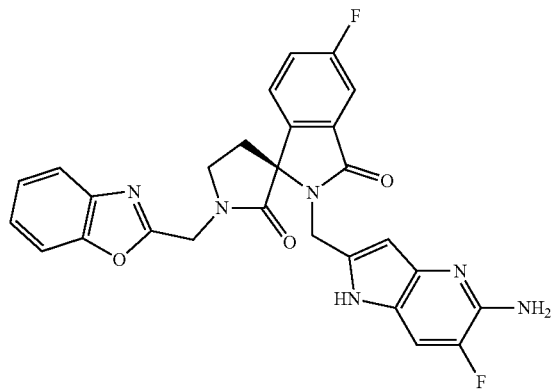 [SMILES: Nc1nc2cc(CN3C(=O)c4cc(F)ccc4[C@]34CCN(Cc3nc5ccccc5o3)C4=O)[nH]c2cc1F]

The title compound (20 mg, 52%, beige solid) was made according to General method C using methyl (S-2-((5-((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate and benzo[d]oxazol-2-5 ylmethanamine hydrochloride.

$^1$H NMR (400 MHz, DMSO-d6, 27° C.) 2.43-2.49 (2H, m), 3.67 (1H, ddd), 3.84-3.98 (1H, m), 4.40 (1H, d), 4.85 (1H, d), 4.94 (1H, d), 5.10 (1H, d), 5.49 (2H, s), 6.16 (1H, d), 7.31-7.40 (1H, m), 7.39-7.48 (2H, m), 7.61 (2H, ddq), 7.75-7.85 (3H, m), 10.72 (1H, d); m/z MH$^+$ 515

Example 17: (S)-2-((5-Amino-6-fluoro-1H-pyrrolo[3,2-b]pyridin-2-yl)methyl)-5-fluoro-1'-(2-(4-fluorophenoxy)ethyl)spiro[isoindoline-1,3'-pyrrolidine]-2',3-dione

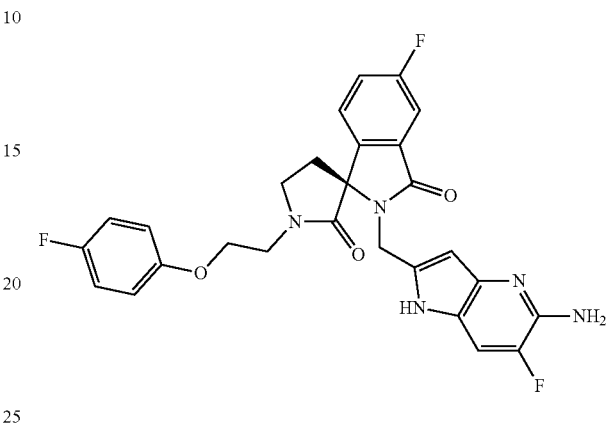

The title compound (32 mg, 69%, white solid) was made according to General method C using methyl (5)-2-((5-((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate and 2-(4-fluorophenoxy)ethan-1-amine.

$^1$H NMR (400 MHz, DMSO-d6, 27° C.) 2.35-2.48 (2H, m), 3.52-3.67 (2H, m), 3.72 (1H, ddd), 3.78-3.88 (1H, m), 4.13 (2H, tt), 4.30 (1H, d), 5.01 (1H, d), 5.49 (2H, s), 6.05 (1H, d), 6.93-7.04 (2H, m), 7.11-7.20(2H, m), 7.32-7.38 (1H, m), 7.39-7.49 (1H, m), 7.57 (2H, td), 10.66 (1H, d); m/z MH$^+$ 522

Example 18: (S)-2-((5-Amino-6-fluoro-1H-pyrrolo[3,2-b]pyridin-2-yl)methyl)-5-fluoro-1'-(2-(4-methylthiazol-5-yl)ethyl)spiro[isoindoline-1,3'-pyrrolidine]-2',3-dione

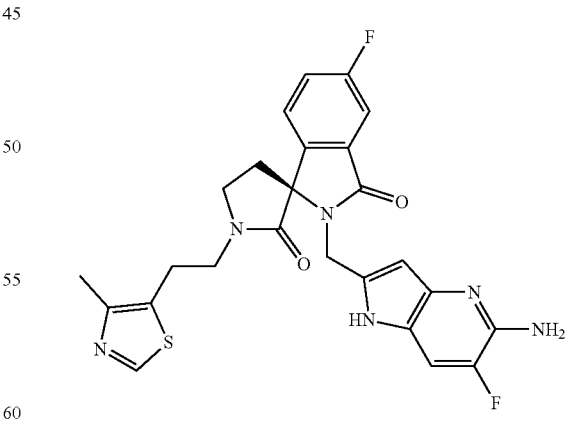

The title compound (27 mg, 69%, white solid) was made according to General method D using methyl (S)-2-((5-((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate and 2-(4-methylthiazol-5-yl)ethan-1-amine.

¹H NMR (400 MHz, DMSO-d6, 27° C.) 2.31-2.43 (5H, m), 3.05 (2H, t), 3.49 (3H, dq), 3.66-3.8 (1H, m), 4.17 (1H, d), 4.95 (1H, d), 5.48 (2H, s), 6.09 (1H, d), 7.36 (1H, d), 7.38-7.52 (2H, m), 7.57 (1H, dd), 8.86 (1H, s), 10.64 (1H, s); m/z MH⁺ 509

Example 19: (S)-2-((5-Amino-6-fluoro-1H-pyrrolo[3,2-b]pyridin-2-yl)methyl)-5-fluoro-1'-((R*)-1-(1-methylcyclopropyl)ethyl)spiro[isoindoline-1,3'-pyrrolidine]-2',3-dione Isomer 2

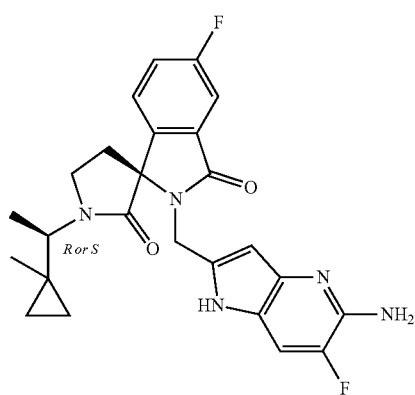

A mixture of the 2 diastereoisomers was made according to General method D using methyl (S)-2-((5-((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate and rac-1-(1-methylcyclopropyl)ethan-1-amine hydrochloride. The diastereoisomers were separated by chiral column: CHIRALPAK IF, 2*25 cm, 5 μm; Mobile Phase A: Hex:DCM=3:1 (0.5% 2M NH₃—MeOH)—HPLC, Mobile Phase B: IPA—HPLC; Flow rate: 20 mL/min; Gradient: 50% B to 50% B in 42 min; Wave Length: 220/254 nm; RT1(min): 26.51; RT2(min): 34.77. Fractions containing the second eluting isomer 2 were evaporated to dryness to afford the title compound (28 mg, 13%, 95% ee) as a white solid.

(Note example 19 has an unknown stereochemical configuration at the methylcyclopropyl position, with fixed assumed S stereochemical configuration at the quaternary centre given intermediate used has assumed S stereochemical configuration)

¹H NMR (400 MHz, DMSO-d6) 0.21-0.33 (2H, m), 0.40 (1H, d), 0.55-0.62 (1H, m), 0.99-1.06 (6H, m), 2.31-2.46 (2H, m), 3.53 (1H, t), 3.66-3.77 (1H, m), 3.80-3.90 (1H, m), 4.19-4.28 (1H, m), 4.99 (1H, d), 5.49 (2H, s), 6.08 (1H, s), 7.31-7.39 (1H, m), 7.49-7.58 (1H, m), 7.54-7.61 (2H, m), 10.71 (1H, s); m/z MH⁺ 466

Example 20: (S)-2-((5-Amino-6-fluoro-1H-pyrrolo[3,2-b]pyridin-2-yl)methyl)-1'-(3-cyclopropylprop-2-yn-1-yl)-5-fluorospiro[isoindoline-1,3'-pyrrolidine]-2',3-dione Step 1; tert-Butyl (S)-(2(1'-(3-cyclopropylprop-2-yn-1-yl)-5-fluoro-2',3-dioxospiro[isoindoline-1,3'-pyrrolidin]-2-yl)methyl)-6-fluoro-1-((2-(trimethylsilyl)ethoxy)methyl)-1H-pyrrolo[3,2-b]pyridin-5-yl)carbamate

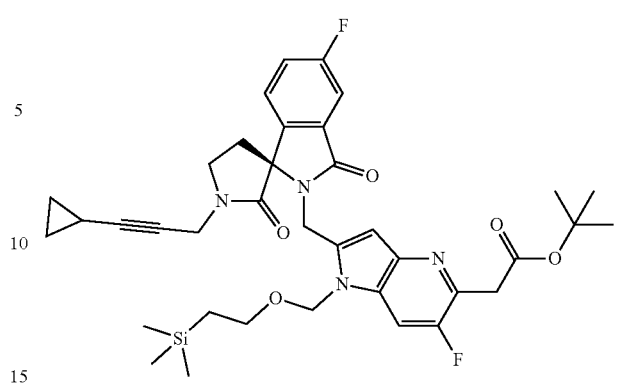

Methyl (S)-2-((5-((tert-butoxycarbonyl)amino)-6-fluoro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate (100 mg, 0.16 mmol) and 3-cyclopropylprop-2-yn-1-amine hydrochloride (30 mg, 0.23 mmol) were placed in a flask with 1,2-dichloroethane (2 mL). Triethylamine (32.4 μl, 0.23 mmol) was added and the reaction mixture was stirred at rt for 15 minutes. Sodium triacetoxyborohydride (66 mg, 0.31 mmol) was added and the reaction mixture was stirred at rt for 6 hours. The reaction mixture was diluted with DCM (25 mL) and washed with saturated NaHCO₃ (25 mL). The organic phase was passed through a phase separating filter paper and the solvent was removed in vacuo. The crude product was purified by flash silica chromatography, elution gradient 0 to 100% EtOAc in heptane. Pure fractions were combined and the solvent was removed in vacuo to afford the title compound (63 mg, 59%) as a beige foam.

¹H NMR (400 MHz, DMSO-d6, 27° C.) −0.13 (9H, s), 0.64-0.67 (2H, m), 0.68-0.77 (2H, m), 0.77-0.83 (2H, m), 1.35 (1H, ddt), 1.42 (9H, s), 2.39 (2H, t), 3.37-3.52 (3H, m), 3.69-3.80 (1H, m), 3.86-4.00 (2H, m), 4.52 (1H, d), 5.19 (1H, d), 5.49-5.59 (2H, m), 6.52 (1H, s), 7.50-7.62 (3H, m), 8.02 (1H, d), 9.15 (1H, s); m/z MH⁺ 692

Step 2; (S)-2-((5-Amino-6-fluoro-1H-pyrrolo[3,2-b]pyridin-2-yl)methyl)-1'-(3-cyclopropylprop-2-yn-1-yl)-5-fluorospiro[isoindoline-1,3'-pyrrolidine]-2',3-dione

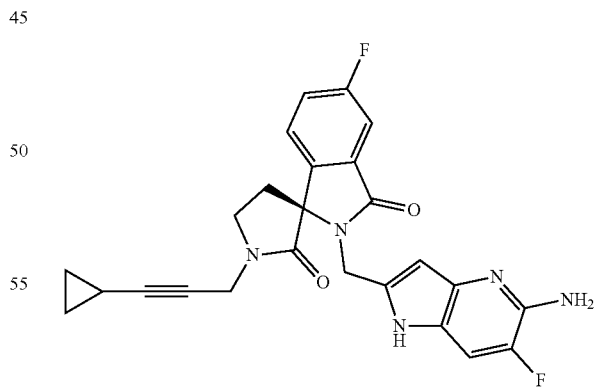

tert-Butyl (S)-(2-((1'-(3-cyclopropylprop-2-yn-1-yl)-5-fluoro-2',3-dioxospiro[isoindoline-1,3'-pyrrolidin]-2-yl)methyl)-6-fluoro-1-((2-(trimethylsilyl)ethoxy)methyl)-1H-pyrrolo[3,2-b]pyridin-5-yl)carbamate (40 mg, 0.06 mmol) was placed in a flask with formic acid (250 μL, 0.06 mmol) and the solution was left at rt for 72 hours. The crude product was purified by preparative HPLC. Fractions containing the desired compound were evaporated to dryness to afford the title compound (10 mg, 35%) as a colourless dry film (m/z MH+ 492). The intermediate was dissolved in DMF (0.50 mL). Ethane-1,2-diamine (12 mg, 0.20 mmol) was added and the reaction mixture was stirred at rt for 1 hour. The crude product was purified by preparative HPLC. Fractions containing the desired compound were evaporated to dryness to afford the title compound (4 mg, 45%) as a colourless dry film.

$^1$H NMR (400 MHz, CD$_3$CN, 27° C.) 0.63-0.69 (2H, m), 0.78-0.84 (2H, m), 1.31 (1H, dddd), 2.39 (1H, ddd), 2.53-2.61 (1H, m), 3.64 (1H, td), 3.78 (1H, dt), 3.97 (1H, dd), 4.13 (1H, dd), 4.45 (1H, d), 4.86 (2H, d), 6.23 (1H, d), 7.34-7.41 (2H, m), 7.45 (1H, dd), 7.49 (1H, dd), 8.10 (1H, s), 9.44 (1H, s); m/z MH+ 462

Example 21: (S)-2-((5-Amino-6-fluoro-1H-pyrrolo[3,2-b]pyridin-2-yl)methyl)-4-chloro-1'-(4-fluorobenzyl)spiro[isoindoline-1,3'-pyrrolidine]-2',3-dione Step 1; Methyl 2-chloro-6-(2-methoxy-2-oxoethyl)benzoate

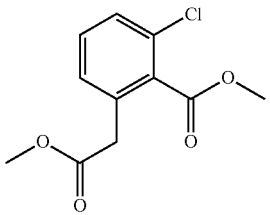

1,1'-Bis(diphenylphosphino)ferrocenedichloropalladium(II) DCM adduct (1.55 g, 1.90 mmol) was added to methyl 2-(2-bromo-3-chlorophenyl)acetate (CAS No. 1021089-12-2) (5.00 g, 18.97 mmol) and TEA (7.93 mL, 56.92 mmol) in MeOH (80 mL) at rt under carbon monoxide. The reaction mixture was stirred at 130° C. for 16 hours. The reaction mixture was allowed to cool and the solvent was removed in vacuo. The crude product was purified by flash silica chromatography, elution gradient 0 to 20% EtOAc in petroleum ether (60-90° C.). Pure fractions were evaporated to dryness to afford the title compound (2.36 g, 51%) as a colourless oil.

$^1$H NMR (400 MHz, DMSO-d6) 3.61 (3H, d), 3.73 (2H, s), 3.85 (3H, d), 7.34-7.43 (1H, m), 7.44-7.54 (2H, m); m/z MH+ not observed.

Step 2; rac-Methyl 2-(1-bromo-2-methoxy-2-oxoethyl)-6-chlorobenzoate

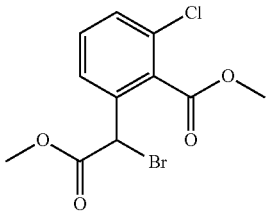

2,2'-Azobis(2-methylpropionitrile) (0.63 g, 3.82 mmol) was added to methyl 5-chloro-2-(2-methoxy-2-oxoethyl)benzoate (2.32 g, 9.54 mmol) and NBS (3.40 g, 19.09 mmol) in CCl$_4$ (50 mL) at rt. The reaction mixture was stirred at 80° C. for 16 hours. The reaction mixture was allowed to cool and the solvent was removed in vacuo. The crude product was purified by flash silica chromatography, elution gradient 0 to 20% EtOAc in petroleum ether (60-90° C.). Pure fractions were evaporated to dryness to afford the title compound (1.75 g, 57%) as a colourless oil.

$^1$H NMR (300 MHz, DMSO-d6) 3.66 (3H, d), 3.90 (3H, s), 5.90 (1H, s), 7.59 (3H, d); m/z MH+ 321

Step 3; rac-Methyl 7-chloro-2-(4-methoxybenzyl)-3-oxoisoindoline-1-carboxylate

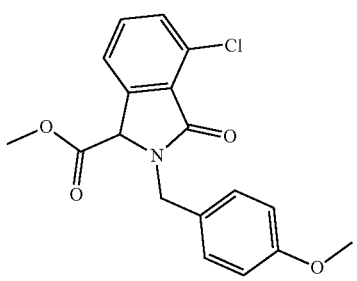

4-Methoxybenzylamine (0.77 g, 5.73 mmol) was added to rac-methyl 2-(1-bromo-2-methoxy-2-oxoethyl)-6-chlorobenzoate (1.75 g, 5.45 mmol) and sodium bicarbonate (1.83 g, 21.82 mmol) in MeCN (28 mL). The reaction mixture was stirred at 60° C. for 3 hours. The reaction mixture was allowed to cool and the solvent was removed in vacuo. The crude product was purified by flash silica chromatography, elution gradient 0 to 40% EtOAc in petroleum ether (60-90° C.). Pure fractions were evaporated to dryness to afford the title compound (1.29 g, 68%) as a yellow solid.

$^1$H NMR (300 MHz, DMSO-d6) 3.63-3.76 (6H, m), 4.29 (1H, d), 4.99 (1H, d), 5.18 (1H, s), 6.85-6.96 (2H, m), 7.17-7.26 (2H, m), 7.49-7.69 (3H, m); m/z MH+ 346

Step 4; rac-Methyl 1-allyl-4-chloro-2-(4-methoxybenzyl)-3-oxoisoindoline-1-carboxylate

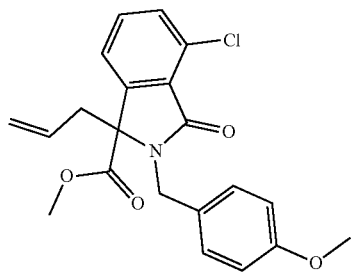 [SMILES: C=CCC1(C(=O)OC)c2cccc(Cl)c2C(=O)N1Cc1ccc(OC)cc1]

1,1,3,3-Tetramethylguanidine (0.67 mL, 5.38 mmol) was added dropwise to rac-methyl 7-chloro-2-(4-methoxybenzyl)-3-oxoisoindoline-1-carboxylate (1.24 g, 3.59 mmol), allyl acetate (0.58 mL, 5.38 mmol), tris(dibenzylideneacetone)dipalladium(0) (0.08 g, 0.09 mmol) and N,N'-((1R,2R)-cyclohexane-1,2-diyl)bis(2-(diphenylphosphaneyl)benzamide) (0.12 g, 0.18 mmol) in THF (16 mL) at 5° C. under nitrogen. The resulting solution was stirred at 5° C. for 10 minutes. The reaction mixture was poured into water (300 mL) and extracted with EtOAc (2×300 mL). The organic phase was dried over Na$_2$SO$_4$, filtered and the solvent was removed in vacuo. The crude product was purified by flash silica chromatography, elution gradient 0 to 30% EtOAc in petroleum ether (60-90° C.). Pure fractions were evaporated to dryness to afford the title compound (1.31 g, 94%) as a white solid.

¹H NMR (400 MHz, DMSO-d6) 3.05-3.14 (1H, m), 3.14-3.22 (1H, m), 3.24 (3H, s), 3.73 (3H, s), 4.49 (1H, d), 4.71 (1H, d), 4.76-4.89 (2H, m), 4.86-4.97 (1H, m), 6.84-6.93 (2H, m), 7.30-7.38 (2H, m), 7.52-7.59 (2H, m), 7.59-7.67 (1H, m); m/z MH⁺ 386

Step 5; rac-Methyl 4-chloro-2-(4-methoxybenzyl)-3-oxo-1-(2-oxoethyl)isoindoline-1-carboxylate

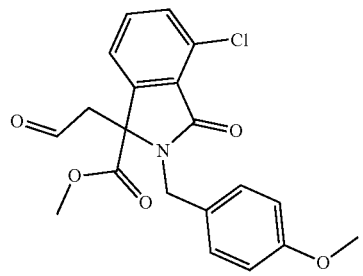 [SMILES: COC(=O)C1(CC=O)c2cccc(Cl)c2C(=O)N1Cc1ccc(OC)cc1]

Potassium osmate(VI) dihydrate (0.02 g, 0.07 mmol) was added to rac-methyl 1-allyl-4-chloro-2-(4-methoxybenzyl)-3-oxoisoindoline-1-carboxylate (1.28 g, 3.32 mmol), 2,6-lutidine (0.71 g, 6.63 mmol) and sodium periodate (2.13 g, 9.95 mmol) in dioxane (15 mL) and water (5 mL). The reaction mixture was stirred at rt for 16 hours. The reaction mixture was extracted with EtOAc (100 mL). The organic phase was dried over Na₂SO₄, filtered and the solvent was removed in vacuo. The crude product was purified by flash silica chromatography, elution gradient 0 to 40% EtOAc in petroleum ether (60-90° C.). Pure fractions were evaporated to dryness to afford the title compound (1.01 g, 78%) as a white solid.

¹H NMR (300 MHz, DMSO-d6) 3.37 (3H, s), 3.49 (1H, s), 3.53 (1H, s), 3.70 (3H, s), 4.54 (1H, d), 4.68 (1H, d), 6.78-6.89 (2H, m), 7.17-7.27 (2H, m), 7.53-7.68 (3H, m), 9.05 (1H, s); m/z MH⁺ 388

Step 6; rac-4-chloro-1'-(4-fluorobenzyl)-2-(4-methoxybenzyl)spiro[isoindoline-1,3'-pyrrolidine]-2',3-dione

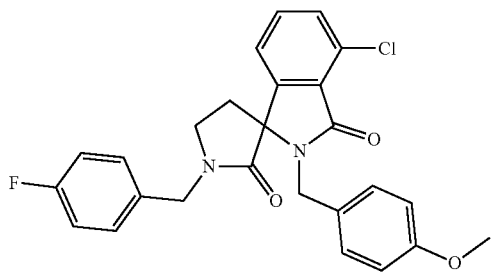 [SMILES: COc1ccc(CN2C(=O)c3c(Cl)cccc3C23CCN(Cc2ccc(F)cc2)C3=O)cc1]

4-fluorobenzylamine (0.650 g, 5.19 mmol) was added to rac-methyl 4-chloro-2-(4-methoxybenzyl)-3-oxo-1-(2-oxoethyl)isoindoline-1-carboxylate (1.01 g, 2.60 mmol) in 1,2-dichloroethane (16 mL). After 1 hour sodium triacetoxyborohydride (1.10 g, 5.19 mmol) was added and the reaction mixture was stirred at rt for 16 hours. The reaction mixture was quenched with saturated NH₄Cl (10 mL) and extracted with EtOAc (3×25 mL). The organic phase was dried over Na₂SO₄, filtered and the solvent was removed in vacuo. The crude product was purified by flash silica chromatography, elution gradient 0 to 70% EtOAc in petroleum ether (60-90° C.). Pure fractions were evaporated to dryness to afford the title compound (1.00 g, 83%) as a white solid.

¹H NMR (300 MHz, DMSO-d6) 2.24-2.42 (2H, m), 3.35-3.40 (1H, m), 3.49-3.66 (1H, m), 3.70 (3H, s), 4.11 (1H, d), 4.40 (2H, s), 4.82 (1H, d), 6.80-6.90 (2H, m), 7.05-7.35 (6H, m), 7.35-7.42 (1H, m), 7.51-7.60 (1H, m), 7.55-7.66 (1H, m); m/z MH⁺ 465

Step 7; rac-4-chloro-1'-(4-fluorobenzyl)spiro[isoindoline-1,3'-pyrrolidine]-2',3-dione

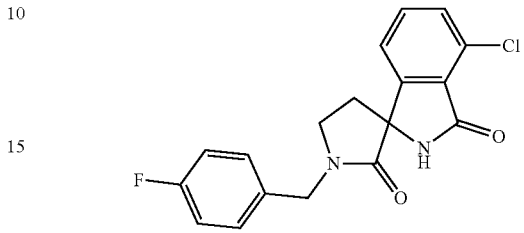

2,2,2-trifluoroacetic acid (13 mL) was added to rac-4-chloro-1'-(4-fluorobenzyl)-2-(4-methoxybenzyl)spiro[isoindoline-1,3'-pyrrolidine]-2',3-dione (0.96 g, 2.06 mmol) at rt. The reaction mixture was stirred at 80° C. for 2 hours. The reaction mixture was neutralised with saturated NaHCO₃ and diluted with water (20 mL) and EtOAc (3×50 mL). The organic phase was dried over Na₂SO₄, filtered and the solvent was removed in vacuo. The crude product was purified by flash silica chromatography, elution gradient 0 to 100% EtOAc in petroleum ether (60-90° C.). Pure fractions were evaporated to dryness to afford the title compound (0.61 g, 86%) as a white solid.

¹H NMR (300 MHz, DMSO-d6) 2.29-2.50 (2H, m), 3.39-3.52 (1H, m), 3.53-3.65 (1H, m), 4.46 (2H, s), 7.14-7.26 (2H, m), 7.27-7.39 (3H, m), 7.46-7.53 (1H, m), 7.57 (1H, t), 9.09 (1H, s); m/z MH⁺ 345

Step 8; rac-4-chloro-2-((5-chloro-6-fluoro-1-((2-(trimethylsilyl)ethoxy)methyl)-1H-pyrrolo[3,2-b]pyridin-2-yl)methyl)-1'-(4-fluorobenzyl)spiro[isoindoline-1,3'-pyrrolidine]-2',3-dione

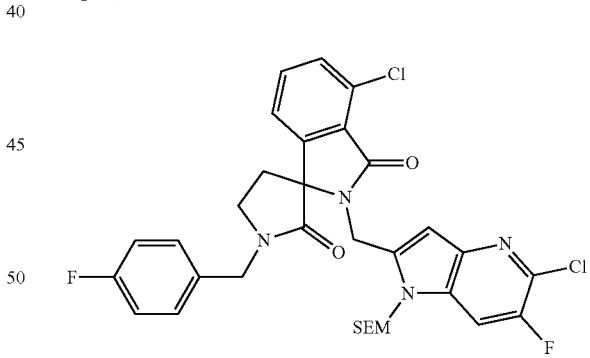

Sodium hydride (60% in mineral oil) (0.10 g, 2.57 mmol) was added to rac-4-chloro-1'-(4-fluorobenzyl)spiro[isoindoline-1,3'-pyrrolidine]-2',3-dione (0.59 g, 1.71 mmol) in THF (12 mL) at 0° C. The reaction mixture was stirred at rt for 1 hour. 5-Chloro-2-(bromomethyl)-6-fluoro-1-((2-(trimethylsilyl)ethoxy)methyl)-1H-pyrrolo[3,2-b]pyridine (0.88 g, 2.23 mmol) was added and the reaction mixture was stirred at rt for 6 hours. The reaction mixture was quenched with saturated NH₄Cl (2 mL) and the solvent was removed in vacuo. The crude product was purified by flash silica chromatography, elution gradient 0 to 50% EtOAc in petroleum ether (60-90° C.). Pure fractions were evaporated to dryness to afford the title compound (0.71 g, 63%) as a yellow solid.

¹H NMR (300 MHz, DMSO-d6) −0.15 (9H, s), 0.55-0.79 (2H, m), 2.19-2.42 (1H, m), 2.50 (1H, s), 3.31-3.39 (1H, m), 3.40-3.52 (2H, m), 3.53-3.68 (1H, m), 4.20-4.38 (2H, m), 4.70 (1H, d), 5.08 (1H, d), 5.52 (1H, d), 5.61 (1H, d), 6.54 (1H, s), 7.09-7.25 (4H, m), 7.34-7.42 (1H, m), 7.53-7.62 (1H, m), 7.57-7.68 (1H, m), 8.29 (1H, d); m/z MH⁺ 658

Step 9; rac-tert-Butyl 2-((4-chloro-1'-(4-fluorobenzyl)-2',3-dioxospiro[isoindoline-1,3'-pyrrolidin]-2-yl)methyl)-6-fluoro-1-((2-(trimethylsilyl)ethoxy)methyl)-1H-pyrrolo[3,2-b]pyridin-5-yl)carbamate

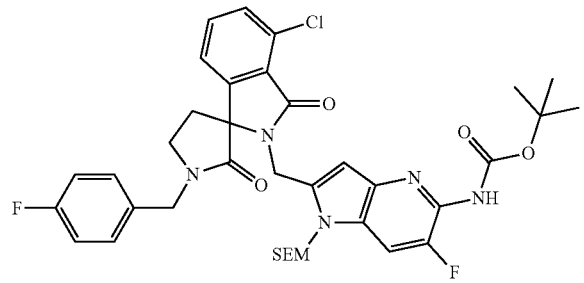 [SMILES: CC(C)(C)OC(=O)Nc1nc2cc(CN3C(=O)c4c(Cl)cccc4C34CCN(Cc3ccc(F)cc3)C4=O)n(COCC[Si](C)(C)C)c2cc1F]

rac-4-Chloro-2-((5-chloro-6-fluoro-1-((2-(trimethylsilyl)ethoxy)methyl)-1H-pyrrolo[3,2-b]pyridin-2-yl)methyl)-1'-(4-fluorobenzyl)spiro[isoindoline-1,3'-pyrrolidine]-2',3-dione (400 mg, 0.61 mmol) was added to tris(dibenzylideneacetone)dipalladium(0) (111 mg, 0.12 mmol), tert-butyl carbamate (64 mg, 0.55 mmol), 9,9-Dimethyl-4,5-bis(diphenylphosphino)xanthene (70 mg, 0.12 mmol) and caesium carbonate (396 mg, 1.22 mmol) in dioxane (4.5 mL) under nitrogen at rt. The reaction mixture was stirred at 80° C. for 4 hours. The solvent was removed in vacuo and the crude product was purified by flash silica chromatography, elution gradient 0 to 40% EtOAc in DCM. Pure fractions were evaporated to dryness to afford the title compound (0.18 g, 40%) as a yellow solid.

¹H NMR (300 MHz, DMSO-d6) −0.15 (9H, s), 0.67 (2H, s), 1.40 (9H, s), 2.22-2.39 (2H, m), 3.58 (2H, d), 4.14-4.40 (3H, m), 4.67 (1H, d), 5.07 (1H, s), 5.36-5.61 (2H, m), 6.43 (1H, s), 7.14-7.30 (4H, m), 7.40 (1H, d), 7.45-7.69 (3H, m), 8.01 (1H, d), 9.20 (1H, s); m/z MH⁺ 738

Step 10: (S)-2-((5-Amino-6-fluoro-1H-pyrrolo[3,2-b]pyridin-2-yl)methyl)-4-chloro-1'-(4-fluorobenzyl)spiro[isoindoline-1,3'-pyrrolidine]-2',3-dione

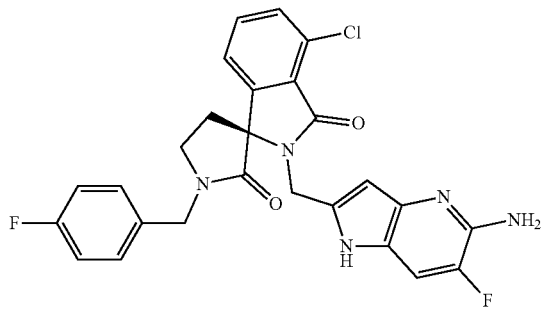 [SMILES: Nc1nc2cc(CN3C(=O)c4c(Cl)cccc4[C@]34CCN(Cc3ccc(F)cc3)C4=O)[nH]c2cc1F]

rac-tert-Butyl 2-((4-chloro-1'-(4-fluorobenzyl)-2',3-dioxospiro[isoindoline-1,3'-pyrrolidin]-2-yl)methyl)-6-fluoro-1-((2-(trimethylsilyl)ethoxy)methyl)-1H-pyrrolo[3,2-b]pyridin-5-yl)carbamate (172 mg, 0.23 mmol) was stirred in 2,2,2-trifluoroacetic acid (2.5 mL) under nitrogen at rt for 1 hour. The crude product was purified by ion exchange chromatography using an SCX column. The desired products were eluted from the column using 7M NH₃/MeOH and pure fractions were evaporated to dryness to afford rac-2-((5-amino-6-fluoro-1H-pyrrolo[3,2-b]pyridin-2-yl)methyl)-4-chloro-1'-(4-fluorobenzyl)spiro[isoindoline-1,3'-pyrrolidine]-2',3-dione. The enantiomers were separated by chiral column: CHIRALPAK IF, 2*25 cm, 5 um; Mobile Phase A:Hex:DCM=3:1 (0.5% 2M NH₃—MeOH)—HPLC, Mobile Phase B:EtOH; Flow rate:15 mL/min; Gradient:50 B to 50 B in 30 min; 254/220 nm; RT1:7.28; RT2:23.02; Fractions containing the desired compound were evaporated to dryness to afford the title compound (31 mg, 27%) as a yellow solid.

(Presumed stereochemical assignment of this compound based on biological activity vs other enantiomer, together with Xray structural evidence that the S enantiomer is preferred and more active than the R enantiomer).

¹H NMR (300 MHz, DMSO-d6) 2.38 (2H, t), 3.39 (1H, d), 3.53-3.67 (1H, m), 4.28 (1H, d), 4.45 (2H, s), 5.01 (1H, d), 5.55 (2H, s), 6.02 (1H, s), 7.17-7.45 (6H, m), 7.53-7.71 (2H, m), 10.72 (1H, d); m/z MH⁺ 508.

Example 22: (S)-2'-((5-Amino-6-fluoro-1H-pyrrolo[3,2-b]pyridin-2-yl)methyl)-1-(4-fluorobenzyl)spiro[pyrrolidine-3,1'-pyrrolo[3,4-c]pyridine]-2,3'(2'H)-dione Step 1; rac-3-(((5-Chloro-6-fluoro-1-((2-(trimethylsilyl)ethoxy)methyl)-1H-pyrrolo[3,2-b]pyridin-2-yl)methyl)amino)-1-(4-fluorobenzyl)pyrrolidin-2-one

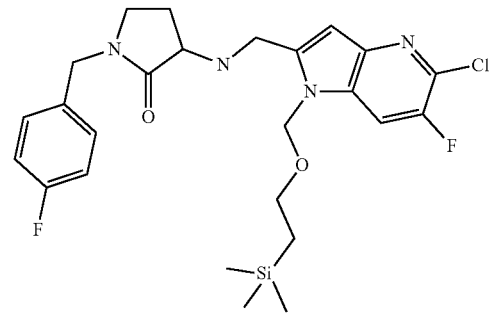 [SMILES: C[Si](C)(C)CCOCn1c(CNC2CCN(Cc3ccc(F)cc3)C2=O)cc2nc(Cl)c(F)cc21]

A solution of 3-amino-1-(4-fluorobenzyl)pyrrolidin-2-one (167 mg, 0.80 mmol) in DCM (5 mL) was added to a stirred solution of 5-chloro-6-fluoro-1-((2-(trimethylsilyl)ethoxy)methyl)-1H-pyrrolo[3,2-b]pyridine-2-carbaldehyde (264 mg, 0.80 mmol) and the mixture was stirred for 2 hours. Sodium borohydride (46 mg, 1.22 mmol) was added followed by MeOH (5 mL). The reaction mixture was stirred for 15 minutes and more sodium borohydride (46 mg, 1.22 mmol) was added. The reaction mixture was stirred for additional 15 minutes and quenched with saturated NaHCO₃ (5 mL) and extracted with DCM (5×10 mL). The organic phase was separated using a phase separating cartridge and the solvent was removed in vacuo. The crude product was purified by flash silica chromatography, elution gradient 0 to 100% EtOAc in heptane to afford the title compound (318 mg, 76%) as a gum.

¹H NMR (400 MHz, CDCl₃, 30° C.) −0.05 (9H, s), 0.84-0.95 (2H, m), 1.69 (1H, dq), 2.20 (1H, dddd), 3.16 (2H, ddd), 3.49 (3H, ddd), 4.10 (1H, d), 4.23 (1H, d), 4.42 (2H, s), 5.58 (2H, d), 6.58 (1H, s), 6.97-7.05 (2H, m), 7.19 (2H, ddd), 7.53 (1H, dd); m/z MH⁺ 521.

Step 2; rac-N-((5-Chloro-6-fluoro-1-((2-(trimethylsilyl)ethoxy)methyl)-1H-pyrrolo[3,2-b]pyridin-2-yl)methyl)-N-(1-(4-fluorobenzyl)-2-oxopyrrolidin-3-yl)nicotinamide

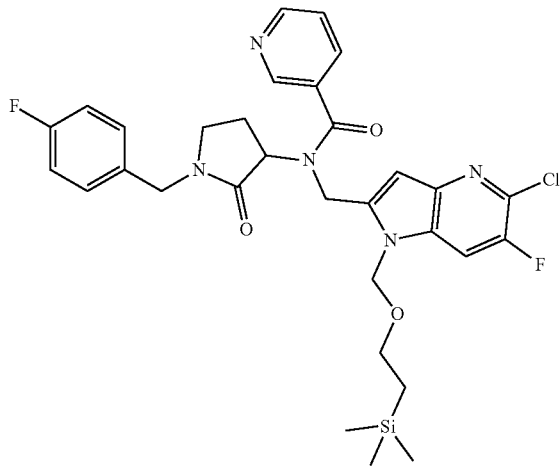 [SMILES: C[Si](C)(C)CCOCn1c(CN(C(=O)c2cccnc2)C2CCN(Cc3ccc(F)cc3)C2=O)cc2nc(Cl)c(F)cc21]

Nicotinoyl chloride hydrochloride (72 mg, 0.40 mmol) was added to a stirred solution of rac-3-(((5-chloro-6-fluoro-1-((2-(trimethylsilyl)ethoxy)methyl)-1H-pyrrolo[3,2-b]pyridin-2-yl)methyl)amino)-1-(4-fluorobenzyl)pyrrolidin-2-one (97 mg, 0.19 mmol) and N-ethyl-N-isopropylpropan-2-amine (200 μl, 1.12 mmol) in DCM (3 mL). The reaction mixture was stirred for 30 minutes and concentrated in vacuo. The crude product was purified by preparative HPLC to afford the title compound (114 mg, 97%) as a gum.

$^1$H NMR (400 MHz, DMSO-d6, 90° C.) −0.10 (9H, s), 0.71 (2H, t), 2.22 (1H, s), 2.29-2.38 (1H, m), 3.19 (2H, t), 3.39 (2H, t), 4.29 (1H, d), 4.44 (1H, d), 4.52 (1H, t), 4.70 (1H, d), 4.99 (1H, d), 5.45-5.57 (2H, m), 6.92 (1H, s), 7.04-7.14 (2H, m), 7.29 (2H, dd), 7.43 (1H, dd), 7.90 (1H, d), 8.17 (1H, d), 8.64 (1H, dd), 8.69-8.71 (1H, m); m/z MH$^+$ 626.

Step 3; rac-2'-((5-Chloro-6-fluoro-1-((2-(trimethylsilyl)ethoxy)methyl)-1H-pyrrolo[3,2-b]pyridin-2-yl)methyl)-1-(4-fluorobenzyl)spiro[pyrrolidine-3,1'-pyrrolo[3,4-c]pyridine]-2,3'(2'H)-dione.

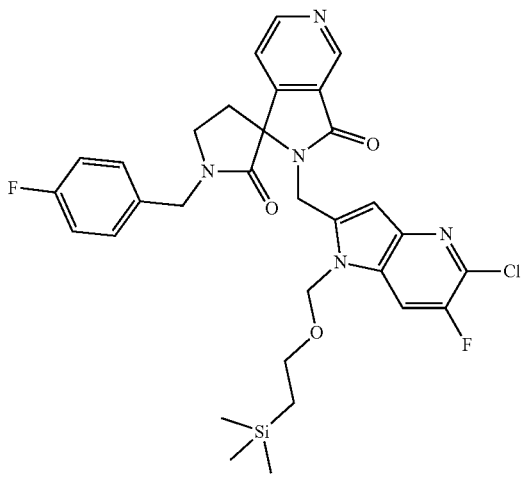 [SMILES: C[Si](C)(C)CCOCn1c(CN2C(=O)c3cnccc3C23CCN(Cc2ccc(F)cc2)C3=O)cc2nc(Cl)c(F)cc21]

A solution of potassium bis(trimethylsilyl)amide 1M in THF (401 μl, 0.40 mmol) was added dropwise to a stirred solution of rac-N-((5-chloro-6-fluoro-1-((2-(trimethylsilyl)ethoxy)methyl)-1H-pyrrolo[3,2-b]pyridin-2-yl)methyl)-N-(1-(4-fluorobenzyl)-2-oxopyrrolidin-3-yl)nicotinamide (114 mg, 0.18 mmol) in THF (5 mL) at −78° C. The reaction mixture was stirred at −78° C. for 30 minutes, slowly warmed to −520° C. (~60 minutes) and quenched with formic acid (40 μl, 1.04 mmol). The reaction mixture was concentrated in vacuo and redissolved in DCM (5 mL). Manganese(IV) oxide (237 mg, 2.73 mmol) was added and the reaction mixture was stirred at rt for 1.5 hours. The reaction mixture was filtered through a pad of Celite® and the filtrate was concentrated in vacuo. The crude product was purified by preparative HPLC to afford the title compound (23 mg, 20%) as a gum.

$^1$H NMR (400 MHz, CDCl$_3$, 30° C.) −0.00 (9H, s), 0.82 (1H, ddd), 0.91 (1H, ddd), 2.30 (1H, ddd), 2.57 (1H, ddd), 3.43 (1H, td), 3.52 (1H, dt), 3.61 (2H, dddd), 4.03 (1H, d), 4.48 (1H, d), 5.08 (1H, d), 5.15 (1H, d), 5.52 (1H, d), 5.58 (1H, d), 6.53-6.59 (1H, m), 7.07 (1H, dd), 7.1-7.23 (4H, m), 7.66 (1H, dd), 8.82 (1H, d), 9.23 (1H, d); m/z MH$^+$ 624.

Step 4; rac-2'-((5-((Diphenylmethylene)amino)-6-fluoro-1-((2-(trimethylsilyl)ethoxy)methyl)-1H-pyrrolo[3,2-12]pyridin-2-yl)methyl)-1-(4-fluorobenzyl)spiro[pyrrolidine-3,1'-pyrrolo[3,4-c]pyridine]-2,3'(2'H)-dione

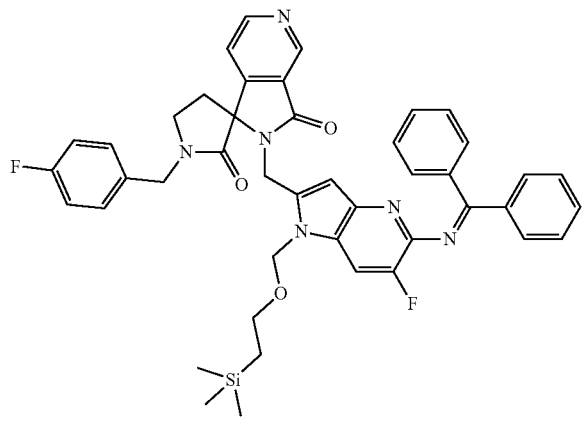 [SMILES: C[Si](C)(C)CCOCn1c(CN2C(=O)c3cnccc3C23CCN(Cc2ccc(F)cc2)C3=O)cc2nc(N=C(c3ccccc3)c3ccccc3)c(F)cc21]

Tris(dibenzylideneacetone)dipalladium(0) (10 mg, 0.01 mmol) was added to a degassed solution of rac-2'-((5-chloro-6-fluoro-1-((2-(trimethylsilyl)ethoxy)methyl)-1H-pyrrolo[3,2-b]pyridin-2-yl)methyl)-1-(4-fluorobenzyl)spiro[pyrrolidine-3,1'-pyrrolo[3,4-c]pyridine]-2,3'(2'H)-dione (48 mg, 0.08 mmol), diphenylmethanimine (42 mg, 0.23 mmol), tBuXPhos (10 mg, 0.02 mmol) and sodium 2-methylpropan-2-olate (30 mg, 0.31 mmol) in toluene (3 mL). The reaction mixture was sealed into a microwave tube and heated at 70° C. for 1 hour in a heating block. The crude product was purified by 25 preparative HPLC to afford the title compound (24 mg, 40%).

$^1$H NMR (400 MHz, CDCl$_3$, 30° C.) −0.10 (9H, s), 0.66-0.84 (2H, m), 2.19 (1H, ddd), 2.44 (1H, ddd), 3.30 (1H, td), 3.33-3.43 (1H, m), 3.43-3.55 (2H, m), 3.79 (1H, d), 4.39 (1H, d), 5.00 (2H, s), 5.33 (1H, d), 5.41 (1H, d), 6.39 (1H, s), 6.96 (1H, dd), 7.04-7.12 (2H, m), 7.15 (5H, td), 7.20-7.25 (2H, m), 7.28-7.33 (1H, m), 7.36-7.45 (2H, m), 7.46-7.53 (1H, m), 7.83 (2H, d), 8.73 (1H, d), 9.15 (1H, d); m/z MH$^+$ 769.

Step 5; (S)-2'-((5-Amino-6-fluoro-1H-pyrrolo[3,2-b]pyridin-2-yl)methyl)-1-(4-fluorobenzyl)spiro[pyrrolidine-3,1'-pyrrolo[3,4-c]pyridine]-2,3'(2'H)-dione

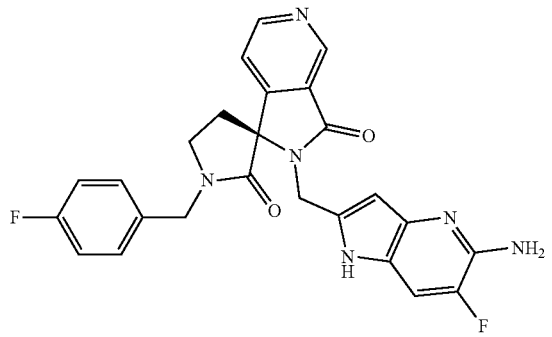 [SMILES: Nc1nc2cc(CN3C(=O)c4cnccc4[C@]34CCN(Cc3ccc(F)cc3)C4=O)[nH]c2cc1F]

A solution of rac-2'-((5-(((diphenylmethylene)amino)-6-fluoro-1-((2-(trimethylsilyl)ethoxy)methyl)-1H-pyrrolo[3,2-b]pyridin-2-yl)methyl)-1-(4-fluorobenzyl)spiro[pyrrolidine-3,1'-pyrrolo[3,4-c]pyridine]-2,3'(2'H)-dione (33 mg, 0.04 mmol) in 2,2,2-trifluoroacetic acid (0.5 mL) and water (0.05 mL) was stirred at 70° C. for 20 minutes and concentrated in vacuo. The residue was redissolved in MeCN (2 mL) and 30% aq. NH$_3$ (0.5 mL) was added. The reaction mixture was stirred in the microwave reactor at 70° C. for 30 minutes, cooled and purified by preparative HPLC to afford the racemic product (20 15 mg, 100%). Both enantiomers were separated using the SFC conditions: column: Phenomenex Lux iC5, 21.2×250 mm, 5 micron, mobile phase: 50% MeOH+0.1% NH$_3$/50% scCO$_2$, flow rate: 60 mL/min; BPR: 120 bar, column temperature: 40 20 C., UV max 220 nm (retention times: Isomer 1—11.9 minutes and Isomer 2—14.4 minutes) to afford Isomer 1 (10 mg, >99 pure, >99% ee) and Isomer 2 (10 mg, >99 pure, >99% ee).

Isomer 1 (example 22)—(S)-2'-((5-Amino-6-fluoro-1H-pyrrolo[3,2-b]pyridin-2-yl)methyl)-1-(4-fluorobenzyl)spiro[pyrrolidine-3,1'-pyrrolo[3,4-c]pyridine]-2,3'(2'H)-dione (Presumed stereochemical assignment of example 22 based on biological activity vs other enantiomer, together with Xray structural evidence that the S enantiomer is preferred and more active than the R enantiomer).

$^1$H NMR (400 MHz, CDCl$_3$, 30° C.) 2.29 (1H, ddd), 2.65 (1H, dt), 3.44-3.60 (2H, m), 4.33 (1H, d), 4.37 (1H, d), 4.40 (2H, s), 4.71 (1H, d), 5.03 (1H, d), 6.24 (1H, d), 7.01 (1H, dd), 7.06-7.14 (2H, m), 7.21-7.29 (3H, m), 8.74 (1H, d), 9.12 (1H, d), 9.15 (1H, s); m/z MH$^+$ 475.

Isomer 2—(R)-2'-((5-Amino-6-fluoro-1H-pyrrolo[3,2-b]pyridin-2-yl)methyl)-1-(4-fluorobenzyl)spiro[pyrrolidine-3,1'-pyrrolo[3,4-c]pyridine]-2,3'(2'H)-dione $^1$H NMR (400 MHz, CDCl$_3$, 30° C.) 2.29 (1H, ddd), 2.65 (1H, dt), 3.44-3.60 (2H, m), 4.33 (1H, d), 4.37 (1H, d), 4.40 (2H, s), 4.71 (1H, d), 5.03 (1H, d), 6.24 (1H, d), 7.01 (1H, dd), 7.06-7.14 (2H, m), 7.21-7.29 (3H, m), 8.74 (1H, d), 9.12 (1H, d), 9.15 (1H, s); m/z MH$^+$ 475.

Example 23: (S)-2-((5-Amino-6-fluoro-1H-pyrrolo[3,2-b]pyridin-2-yl)methyl)-5-fluoro-1',7-dimethyl-spiro[isoindoline-1,3'-pyrrolidine]-2',3-dione Step 1; rac-5-fluoro-2-(4-methoxybenzyl)-1',7-dimethyl-spiro[isoindoline-1,3'-pyrrolidine]-2',3-dione

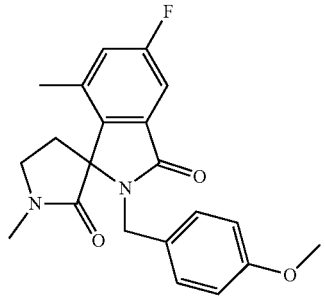

Pd118 (63 mg, 0.09 mmol) was added to rac-7-bromo-5-fluoro-2-(4-methoxybenzyl)-1'-methylspiro[isoindoline-1,3'-pyrrolidine]-2',3-dione (400 mg, 0.92 mmol), 2,4,6-trimethyl-1,3,5,2,4,6-trioxatriborinane (232 mg, 1.85 mmol) and potassium phosphate, tribasic (392 mg, 1.85 mmol) in dioxane (5 mL) under nitrogen at rt. The reaction mixture was stirred at 90° C. for 4 hours, cooled and the solvent was removed in vacuo. The crude product was purified by flash silica chromatography, elution gradient 0 to 100% EtOAc in petroleum ether (60-90° C.). Pure fractions were evaporated to dryness to afford the title compound (30 mg, 88%) as a yellow solid.

$^1$H NMR (400 MHz, DMSO-d6) 2.20 (3H, s), 2.71 (3H, s), 3.33 (2H, s), 3.46-3.60 (2H, m), 3.72 (3H, s), 4.42 (1H, d), 4.59 (1H, d), 6.82-6.90 (2H, m), 7.18-7.27 (2H, m), 7.28-7.39 (2H, m); m/z MH$^+$ 369.

Step 2; rac-5-fluoro-1',7-dimethylspiro[isoindoline-1,3'-pyrrolidine]-2',3-dione

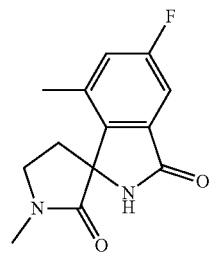 [SMILES: Cc1cc(F)cc2c1C1(CCN(C)C1=O)NC2=O]

Ammonium cerium(IV) nitrate (446 mg, 0.81 mmol) was added to rac-5-fluoro-2-(4-methoxybenzyl)-1',7-dimethyl-spiro[isoindoline-1,3'-pyrrolidine]-2',3-dione (300 mg, 0.81 mmol) in water (1.50 mL) and MeCN (3 mL) at rt. The reaction mixture was stirred at rt for 1 hour and the solvent was removed in vacuo. The crude product was purified by flash silica chromatography, elution gradient 0 to 100% EtOAc in petroleum ether (60-90° C.). Pure fractions were evaporated to dryness to afford the title compound (120 mg, 59%) as a yellow solid.

$^1$H NMR (400 MHz, DMSO-d6) 2.22 (3H, s), 2.49 (1H, d), 2.51 (1H, d), 2.86 (3H, s), 3.53-3.65 (2H, m), 7.21-7.33 (2H, m), 9.16 (1H, s); m/z MH$^+$ 249

Step 4; (S)-2-((5-Amino-6-fluoro-1H-pyrrolo[3,2-b]pyridin-2-yl)methyl)-5-fluoro-1',7-dimethylspiro[isoindoline-1,3'-pyrrolidine]-2',3-dione

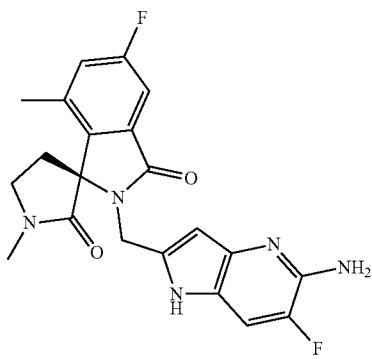 [SMILES: Cc1cc(F)cc2c1[C@]1(CCN(C)C1=O)N(Cc1cc3nc(N)c(F)cc3[nH]1)C2=O]

rac-5-Fluoro-1',7-dimethylspiro[isoindoline-1,3'-pyrrolidine]-2',3-dione (120 mg, 0.48 mmol) was added to 5-chloro-2-(chloromethyl)-6-fluoro-1-((2-(trimethylsilyl)ethoxy)methyl)-1H-pyrrolo[3,2-b]pyridine (169 mg, 0.48 mmol) and caesium carbonate (315 mg, 0.97 mmol) in DMF (3 mL) under nitrogen at rt. The reaction mixture was stirred at 60° C. for 16 hours, cooled and the solvent was removed in vacuo. The crude product was purified by flash silica chromatography, elution gradient 0 to 4% EtOAc in petroleum ether (60-90° C.). Fractions were evaporated to dryness to afford rac-2-((5-chloro-6-fluoro-1-((2-(trimethylsilyl)ethoxy)methyl)-1H-pyrrolo[3,2-b]pyridin-2-yl)methyl)-5-fluoro-1',7-dimethylspiro[isoindoline-1,3'-pyrrolidine]-2',3-dione (100 mg, 37%) as an impure yellow solid.

EPhos Pd G4 (13 mg, 0.01 mmol) was added to rac-2-((5-chloro-6-fluoro-1-((2-(trimethylsilyl)ethoxy)methyl)-1H-pyrrolo[3,2-b]pyridin-2-yl)methyl)-5-fluoro-1',7-dimethylspiro[isoindoline-1,3'-pyrrolidine]-2',3-dione (80 mg, 0.14 mmol), tert-butyl carbamate (17 mg, 0.14 mmol), caesium carbonate (93 mg, 0.29 mmol) and EPhos (8 mg, 0.01 mmol) in 1,4-dioxane (2 mL) under nitrogen. The reaction mixture was stirred at 80° C. for 1 hour. The reaction mixture was filtered through Celit® and the solvent was removed in vacuo. 2,2,2-trifluoroacetic acid (2 mL) was added and the reaction mixture was stirred at rt for 1 hour. The crude product was purified by ion exchange chromatography, using an SCX column. The racemic product was eluted from the column using 7M NH₃/MeOH, fractions were combined and the solvent was removed in vacuo. The enantiomers were separated by chiral column: CHIRALPAK ID, 2*25 cm, 5 um; Mobile Phase A:MTBE (0.5% 2M NH₃—MeOH)—HPLC, Mobile Phase B:EtOH—HPLC; Flow rate:18 mL/min; Gradient:30 B to 30 B in 10 min; 220/254 nm. The fractions containing the desired compound were evaporated to dryness to afford the title compound (4 mg, 7%) as a white solid.

(Presumed stereochemical assignment of this compound based on biological activity vs other enantiomer, together with Xray structural evidence that the S enantiomer is preferred and more active than the R enantiomer).

$^1$H NMR (400 MHz, DMSO-d6) 2.21 (4H, s), 2.59-2.71 (1H, m), 2.74 (3H, s), 3.48-3.65 (2H, m), 4.58 (1H, d), 4.78 (1H, d), 6.28 (1H, d), 6.80 (2H, broad), 7.30-7.41 (2H, m), 7.76 (1H, d), 11.34 (1H, s); m/z MH⁺ 412

Example 24: (S)-2-((5-Amino-6-fluoro-1H-pyrrolo[3,2-b]pyridin-2-yl)methyl)-5-fluoro-7-methoxy-1'-methylspiro[isoindoline-1,3'-pyrrolidine]-2',3-dione Step 1; rac-5-fluoro-7-methoxy-1'-methylspiro[isoindoline-1,3'-pyrrolidine]-2',3-dione

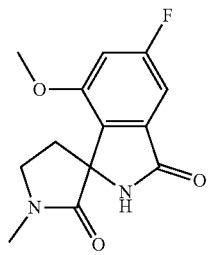 [SMILES: COc1cc(F)cc2c1C1(CCN(C)C1=O)NC2=O]

Rockphos Pd G3 (0.19 g, 0.23 mmol) was added to rac-7-bromo-5-fluoro-2-(4-methoxybenzyl)-1'-methylspiro[isoindoline-1,3'-pyrrolidine]-2',3-dione (1.00 g, 2.31 mmol) and caesium carbonate (1.50 g, 4.62 mmol) in MeOH (10 mL) under nitrogen. The reaction mixture was stirred at 80° C. for 1 hour, cooled and the solvent was removed in vacuo. The crude product was purified by flash C18-flash chromatography, elution gradient 0 to 60% MeOH in water (0.1% FA). Pure fractions were evaporated to dryness to afford rac-(R)-5-fluoro-7-methoxy-2-(4-methoxybenzyl)-1'-methylspiro[isoindoline-1,3'-pyrrolidine]-2',3-dione (0.22 g, 25%) as an impure white solid. Ceric ammonium nitrate (0.86 g, 1.56 mmol) was added to the intermediate (0.20 g, 0.52 mmol) in water (1 mL) and MeCN (2 mL) at rt. The reaction mixture was stirred at rt for 1 hour and the solvent was removed in vacuo. The crude product was purified by flash silica chromatography, elution gradient 0 to 100% EtOAc in petroleum ether (60-90° C.). Pure fractions were evaporated to dryness to afford the title compound (0.13 g, 95%) as a yellow solid.

$^1$H NMR (400 MHz, DMSO-d6) 2.23-2.35 (1H, m), 2.52-2.59 (1H, m), 2.83 (3H, s), 3.44-3.61 (2H, m), 3.85 (3H, s), 6.96-7.03 (1H, m), 7.10-7.18 (1H, m), 9.05 (1H, s); m/z MH⁺ 265

Step 2; rac-2-((5-chloro-6-fluoro-1-((2-(trimethylsilyl)ethoxy)methyl)-1H-pyrrolo[3,2-b]pyridin-2-yl)methyl)-5-fluoro-7-methoxy-1'-methylspiro[isoindoline-1,3'-pyrrolidine]-2',3-dione

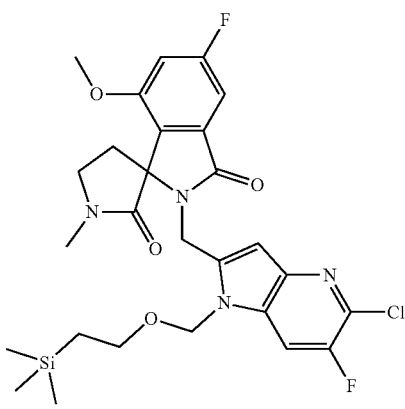 [SMILES: COc1cc(F)cc2c1C1(CCN(C)C1=O)N(Cc1cc3nc(Cl)c(F)cc3n1COCC[Si](C)(C)C)C2=O]

Sodium hydride (60% in mineral oil) (36 mg, 0.91 mmol) was added to rac-5-fluoro-7-methoxy-1'-methylspiro[isoindoline-1,3'-pyrrolidine]-2',3-dione (200 mg, 0.76 mmol) in THF (3 mL) under nitrogen at rt. The reaction mixture was stirred at rt for 20 minutes. 2-(Bromomethyl)-5-chloro-6-fluoro-1-((2-(trimethylsilyl)ethoxy)methyl)-1H-pyrrolo[3,2-b]pyridine (298 mg, 0.76 mmol) was then added and the reaction mixture was stirred at rt for 1 hour. The reaction mixture was quenched with saturated NH₄Cl and extracted with EtOAc (25 mL). The organic phase was dried over Na₂SO₄, filtered and the solvent was removed in vacuo. The crude product was purified by flash silica chromatography, elution gradient 0 to 60% EtOAc in petroleum ether (60-90° C.). Pure fractions were evaporated to dryness to afford the title compound (200 mg, 46%) as a yellow solid.

¹H NMR (400 MHz, DMSO-d6) −0.11 (9H, s), 0.67-0.77 (2H, m), 2.34-2.46 (2H, m), 2.70 (3H, s), 3.27-3.47 (1H, m), 3.43-3.50 (1H, m), 3.47-3.60 (2H, m), 3.84 (3H, s), 4.71-4.84 (1H, m), 4.95-5.11 (1H, m), 5.45-5.56 (1H, m), 5.58 (1H, t), 6.65 (1H, d), 7.12-7.16 (1H, m), 7.45-7.67 (1H, m), 8.25-8.32 (1H, m); m/z MH⁺ 577

Step 3; rac-tert-butyl (6-fluoro-2-((5-fluoro-7-methoxy-1'-methyl-2',3-dioxospiro[isoindoline-1,3'-pyrrolidin]-2-yl)methyl)-1-((2-(trimethylsilyl)ethoxy)methyl)-1H-pyrrolo[3,2-b]pyridin-5-yl)carbamate

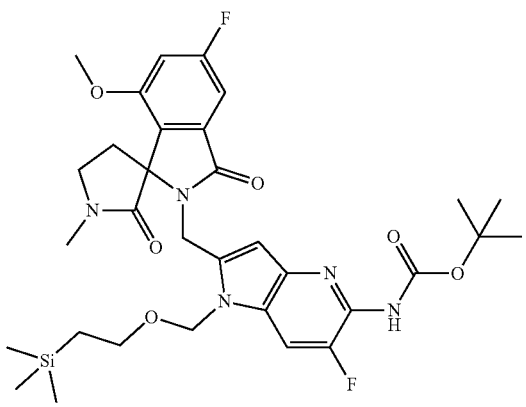 [SMILES: COc1cc(F)cc2c1C1(CCN(C)C1=O)N(Cc1cc3nc(NC(=O)OC(C)(C)C)c(F)cc3n1COCC[Si](C)(C)C)C2=O]

EPhos Pd (28 mg, 0.03 mmol) was added to rac-2-((5-chloro-6-fluoro-1-((2-(trimethylsilyl)ethoxy)methyl)-1H-pyrrolo[3,2-b]pyridin-2-yl)methyl)-5-fluoro-7-methoxy-1'-methylspiro[isoindoline-1,3'-pyrrolidine]-2',3-dione (200 mg, 0.30 mmol), tert-butyl carbamate (36 mg, 0.30 mmol), caesium carbonate (297 mg, 0.91 mmol) and EPhos (16 mg, 0.03 mmol) in 1,4-dioxane (3 mL) under nitrogen. The reaction mixture was stirred at 80° C. for 1 hour, cooled and the solvent was removed in vacuo. The crude product was purified by flash silica chromatography, elution gradient 0 to 60% EtOAc in petroleum ether (60-90° C.). Fractions were evaporated to dryness to afford the crude title compound (150 mg, 75%) as a yellow solid. MH⁺ 658.

Step 4; (S)-2-((5-Amino-6-fluoro-1H-pyrrolo[3,2-b]pyridin-2-yl)methyl)-5-fluoro-7-methoxy-1'-methylspiro[isoindoline-1,3'-pyrrolidine]-2',3-dione

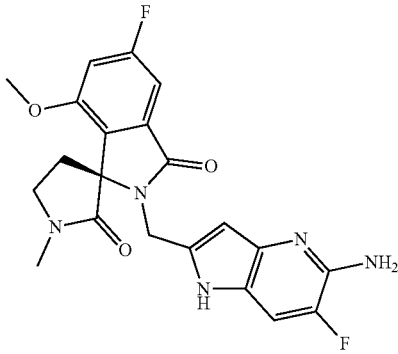 [SMILES: COc1cc(F)cc2c1[C@]1(CCN(C)C1=O)N(Cc1cc3nc(N)c(F)cc3[nH]1)C2=O]

2,2,2-trifluoroacetic acid (2 mL) was added to rac-tert-butyl (6-fluoro-2-((5-fluoro-7-methoxy-1'-methyl-2',3-dioxospiro[isoindoline-1,3'-pyrrolidin]-2-yl)methyl)-1-((2-(trimethylsilyl)ethoxy)methyl)-1H-pyrrolo[3,2-b]pyridin-5-yl)carbamate (150 mg, 0.23 mmol). The reaction mixture was stirred at rt for 1 hour and the solvent was removed in vacuo. The crude product was purified by ion exchange chromatography, using an SCX column. The desired product was eluted from the column using 7M NH₃/MeOH, fractions were combined and the solvent was removed in vacuo. The enantiomers were separated by chiral column: CHIRALPAK ID, 2*25 cm, 5 μm; Mobile Phase A: Hex: DCM=3:1 (0.5% 2M NH₃—MeOH)—HPLC, Mobile Phase B: EtOH—HPLC; Flow rate: 15 mL/min; Gradient: 50% B to 50% B in 47 min; Wave Length: 220/254 nm. The fractions containing the desired compound were evaporated to dryness to afford the title compound (23 mg, 24%) as a white solid.

(Presumed stereochemical assignment of this compound based on biological activity vs other enantiomer, together with Xray structural evidence that the S enantiomer is preferred and more active than the R enantiomer).

¹H NMR (400 MHz, DMSO-d6) 2.19-2.31 (1H, m), 2.38-2.49 (1H, m), 2.78 (3H, s), 3.37-3.47 (1H, m), 3.48-3.58 (1H, m), 3.86 (3H, s), 4.28 (1H, d), 4.89 (1H, d), 5.49 (2H, s), 6.11 (1H, d), 7.08-7.15 (1H, m), 7.15-7.23 (1H, m), 7.36 (1H, d), 10.65 (1H, d); m/z MH⁺ 428

Example 25: (S)-2'-((5-Amino-6-fluoro-1H-pyrrolo[3,2-b]pyridin-2-yl)methyl)-1-(4-fluorobenzyl)spiro[pyrrolidine-3,3'-pyrrolo[3,4-c]pyridine]-1',2(2'H)-dione Step 1; rac-1-(4-Fluorobenzyl)-3-((4-methoxybenzyl)amino)pyrrolidin-2-one

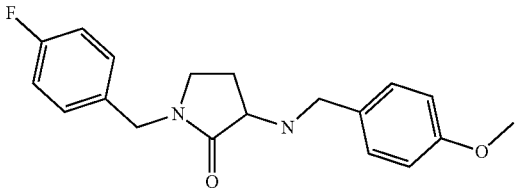

4-Methoxybenzaldehyde (251 μl, 2.06 mmol) was added to a stirred solution of 3-amino-1-(4-fluorobenzyl)pyrrolidin-2-one (430 mg, 2.06 mmol) in DCM (5 mL) and the reaction mixture was stirred at rt for 2 hours. Sodium borohydride (138 mg, 3.65 mmol) was added followed by MeOH (5 mL). The reaction mixture was stirred for 45 minutes, quenched with saturated NaHCO₃ (15 mL) and extracted with DCM (3×50 mL). The organic phase was separated using a phase separating cartridge and the solvent was removed in vacuo. The crude product was purified by flash silica chromatography, elution gradient 0 to 100% EtOAc in heptane, then elution gradient 0 to 20% MeOH in EtOAc to afford the title compound (0.64 g, 94%) as a colourless gum.

¹H NMR (400 MHz, CDCl₃, 30° C.) 1.78 (1H, dq), 2.22 (1H, dddd), 3.07-3.23 (2H, m), 3.45 (1H, t), 3.80 (1H, d), 3.80 (3H, s), 3.84 (1H, d), 4.34-4.50 (2H, m), 6.83-6.88 (2H, m), 6.96-7.04 (2H, m), 7.19 (2H, ddd), 7.24-7.29 (2H, m); m/z MH⁺ 329.

Step 2; rac-N-(1-(4-Fluorobenzyl)-2-oxopyrrolidin-3-yl)-N-(4-methoxybenzyl)isonicotinamide

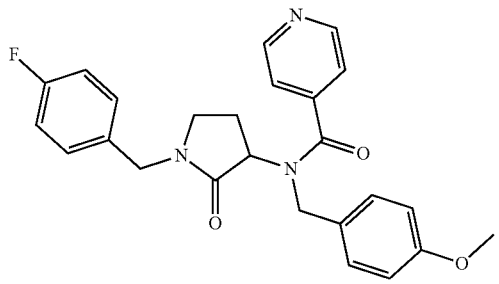 [SMILES: COc1ccc(CN(C(=O)c2ccncc2)C2CCN(Cc3ccc(F)cc3)C2=O)cc1]

Isonicotinoyl chloride hydrochloride (136 mg, 0.76 mmol) was added to a stirred solution of 1-(4-fluorobenzyl)-3-((4-methoxybenzyl)amino)pyrrolidin-2-one (125 mg, 0.38 mmol) and DIPEA (332 μl, 1.90 mmol) in DCM (3 mL). The reaction mixture was stirred for 15 minutes and concentrated in vacuo. The crude product was purified by preparative HPLC to afford the title compound (159 mg, 96%) as a solid.

$^1$H NMR (400 MHz, DMSO-d6, 90° C.) 2.02-2.12 (1H, m), 2.11-2.22 (2H, m), 3.11-3.22 (2H, m), 3.76 (3H, s), 4.29 (1H, d), 4.32-4.41 (1H, m), 4.45 (1H, d), 4.60 (1H, s), 6.89 (2H, d), 7.11 (2H, t), 7.24 (2H, d), 7.26-7.34 (2H, m), 7.38 (2H, d), 8.65 (2H, d); m/z MH$^+$ 434.

Step 3; rac-1-(4-Fluorobenzyl)-2'-(4-methoxybenzyl) spiro[pyrrolidine-3,3'-pyrrolo[3,4-c]pyridine]-1',2(2'H)-dione

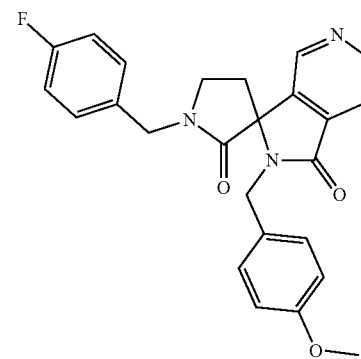

A solution of potassium bis(trimethylsilyl)amide (1M in THF) (807 μl, 0.81 mmol) was added dropwise to a stirred solution of rac-N-(1-(4-fluorobenzyl)-2-oxopyrrolidin-3-yl)-N-(4-methoxybenzyl)isonicotinamide (140 mg, 0.32 mmol) in THF (3 mL) at −78 ° C. The reaction mixture was stirred at −78° C. for 30 minutes and warmed up to −20° C. over 4 hours. The reaction mixture was kept at −20° C. for 2 days. The reaction mixture was quenched with formic acid (50 μl, 1.30 mmol) and concentrated in vacuo. The residue was dissolved in DCM (3 mL). Manganese(IV) oxide (440 mg, 5.06 mmol) was added and the reaction mixture was stirred for 1 hour. The inorganic solid was filtered off and the filtrate was concentrated in vacuo. The crude product was purified by preparative HPLC to afford the title compound (26 mg, 19%) as a gum.

$^1$H NMR (400 MHz, CDCl$_3$, 27° C.) 2.24 (1H, ddd), 2.34 (1H, ddd), 3.24-3.34 (1H, m), 3.49 (1H, dt), 3.78 (3H, s), 4.06 (1H, d), 4.41 (1H, d), 4.61 (1H, d), 5.25 (1H, d), 6.75-6.85 (2H, m), 7.06-7.17 (4H, m), 7.25-7.3 (2H, m), 7.81 (1H, dd), 8.52 (1H, d), 8.81 (1H, d); m/z MH$^+$ 432.

Step 4; rac-1-(4-Fluorobenzyl)spiro[pyrrolidine-3,3'-pyrrolo[3,4-c]pyridine]-1',2(2'H)-dione

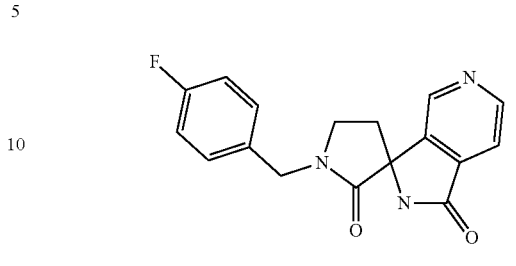

Ammonium cerium(IV) nitrate (182 mg, 0.33 mmol) was added to a stirred solution of rac-1-(4-fluorobenzyl)-2'-(4-methoxybenzyl)spiro[pyrrolidine-3,3'-pyrrolo[3,4-c]pyridine]-1',2(2'H)-dione (26 mg, 0.06 mmol) in MeCN (1 mL) and water (0.5 mL). The reaction mixture was stirred at rt for 45 minutes and purified by preparative HPLC to afford the title compound (14 mg, 75%) as a white solid.

$^1$H NMR (400 MHz, MeOD-d$_4$, 27° C.) 2.56 (1H, ddd), 2.65 (1H, ddd), 3.60 (1H, ddd), 3.74 (1H, dt), 4.55 (1H, d), 4.61 (1H, d), 7.09-7.16 (2H, m), 7.33-7.40 (2H, m), 7.79 (1H, dd), 8.67 (1H, d), 8.79 (1H, d); m/z MH$^+$ 312.

Step 5; rac-2'4(5-Chloro-6-fluoro-1-((2-(trimethylsilyl)ethoxy)methyl)-1H-pyrrolo[3,2-b]pyridin-2-yl)methyl)-1-(4-fluorobenzyl)spiro[pyrrolidine-3,3'-pyrrolo[3,4-c]pyridine]-1',2(2'H)-dione

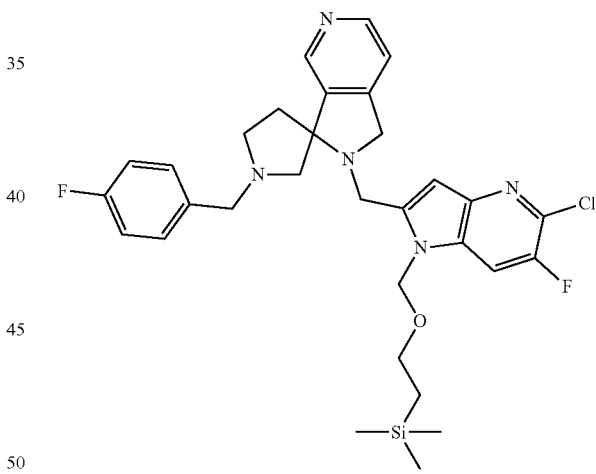

A mixture of rac-1-(4-fluorobenzyl)spiro[pyrrolidine-3,3'-pyrrolo[3,4-c]pyridine]-1',2(2'H)-dione (14 mg, 0.04 mmol), 5-chloro-2-(chloromethyl)-6-fluoro-1-((2-(trimethylsilyl)ethoxy)methyl)-1H-pyrrolo[3,2-b]pyridine (27 mg, 0.08 mmol), caesium carbonate (51 mg, 0.16 mmol) and DMA (1 mL) was stirred at 85° C. for 3 hours and cooled to rt. The reaction mixture was filtered and the filtrate was purified by preparative HPLC to afford the title compound (23 mg, 80%) as a gum.

$^1$H NMR (400 MHz, CDCl$_3$, 27° C.) −0.07 (9H, s), 0.75 (1H, ddd), 0.84 (1H, ddd), 2.28 (1H, ddd), 2.55 (1H, ddd), 3.37 (1H, td), 3.45-3.60 (3H, m), 4.00 (1H, d), 4.42 (1H, d), 5.03 (1H, d), 5.10 (1H, d), 5.44 (1H, d), 5.50 (1H, d), 6.51 (1H, s), 7.03-7.14 (4H, m), 7.59 (1H, dd), 7.81 (1H, dd), 8.43-8.52 (1H, m), 8.83 (1H, d); m/z MH$^+$ 624.

Step 6; (S)-2'-((5-Amino-6-fluoro-1H-pyrrolo[3,2-b]pyridin-2-yl)methyl)-1-(4-fluorobenzyl)spiro[pyrrolidine-3,3'-pyrrolo[3,4-c]pyridine]-1',2(2'H)-dione

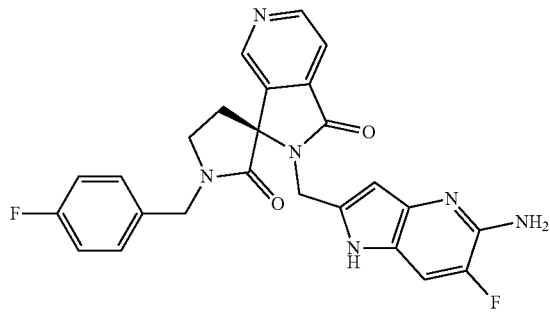 [SMILES: Nc1nc2cc(CN3C(=O)c4ccncc4[C@]34CCN(Cc3ccc(F)cc3)C4=O)[nH]c2cc1F]

Tris(dibenzylideneacetone)dipalladium(0) (5 mg, 5.41 µmol) was added to a degassed solution of rac-2'-((5-chloro-6-fluoro-1-((2-(trimethylsilyl)ethoxy)methyl)-1H-pyrrolo[3,2-b]pyridin-2-yl)methyl)-1-(4-fluorobenzyl)spiro[pyrrolidine-3,3'-pyrrolo[3,4-c]pyridine]-1',2(2'H)-dione (22 mg, 0.04 mmol), diphenylmethanimine (20 mg, 0.11 mmol), tBuXPhos (5 mg, 10.81 µmol) and sodium 2-methylpropan-2-olate (14 mg, 0.15 mmol) in toluene (2 mL). The reaction mixture was sealed into a microwave tube and heated at 80° C. in a heating block for 1 hour. After cooling to rt the reaction mixture was quenched with 1 drop of formic acid and concentrated in vacuo. The residue was redissolved in 2,2,2-trifluoroacetic acid (0.5 mL) and water (0.05 mL). The reaction mixture was stirred at 40° C. for 30 minutes and concentrated in vacuo. MeCN (1 mL) was added followed by 30% aq. NH₃ (0.5 mL). The mixture was sealed and stirred at 70° C. for 30 minutes. The crude mixture was purified by preparative HPLC to afford rac-2'((5-amino-6-fluoro-1H-pyrrolo[3,2-b]pyridin-2-yl)methyl)-1-(4-fluorobenzyl)spiro[pyrrolidine-3,3'-pyrrolo[3,4-c]pyridine]-1',2(2'H)-dione (13 mg, 78%) as a gum. The enantiomers were separated using the SFC conditions: column: YMC Amylose C, 20×250 mm, 5 micron, mobile phase: 45% MeOH+0.1% NH₃/55% scCO₂: 60 mL/min; BPR: 120 bar, column temperature: 40° C., UV max 210 nm (retention times: Isomer 1—3.3 minutes and Isomer 2—11.8 minutes) to afford Isomer 1 (6 mg, >99 pure, >99% ee) and Isomer 2 (5 mg, >99 pure, >99% ee).

Isomer 1—(R)-2'-((5-Amino-6-fluoro-1H-pyrrolo[3,2-b]pyridin-2-yl)methyl)-1-(4-fluorobenzyl)spiro[pyrrolidine-3,3'-pyrrolo[3,4-c]pyridine]-1',2(2'H)-dione $^1$H NMR (400 MHz, CDCl₃, 27° C.) 2.33 (1H, ddd), 2.71 (1H, dt), 3.48-3.66 (2H, m), 4.34 (1H, d), 4.40 (2H, s), 4.40 (1H, d), 4.76 (1H, d), 5.03 (1H, d), 6.27 (1H, d), 7.06-7.14 (2H, m), 7.26 (3H, s), 7.78 (1H, dd), 8.49 (1H, d), 8.82 (1H, d), 9.11 (1H, s); m/z MH⁺ 475.

Isomer 2 (example 25)—(S)-2'-((5-Amino-6-fluoro-1H-pyrrolo[3,2-b]pyridin-2-yl)methyl)-1-(4-fluorobenzyl)spiro[pyrrolidine-3,3'-pyrrolo[3,4-c]pyridine]-1',2(2'H)-dione (Presumed stereochemical assignment of this compound based on biological activity vs other enantiomer, together with Xray structural evidence that the S enantiomer is preferred and more active than the R enantiomer).

$^1$H NMR (400 MHz, CDCl₃, 27° C.) 2.33 (1H, ddd), 2.71 (1H, dt), 3.48-3.66 (2H, m), 4.34 (1H, d), 4.40 (2H, s), 4.40 (1H, d), 4.76 (1H, d), 5.03 (1H, d), 6.27 (1H, d), 7.06-7.14 (2H, m), 7.26 (3H, s), 7.78 (1H, dd), 8.49 (1H, d), 8.82 (1H, d), 9.11 (1H, s); m/z MH⁺ 475

Example 26: (S)-5-Amino-2-((5-fluoro-1'-((1-methylcyclopropyl)methyl)-2',3-dioxospiro[isoindoline-1,3'-pyrrolidin]-2-yl)methyl)-1H-pyrrolo[3,2-b]pyridine-7-carbonitrile Step 1: Methyl (S)-1-allyl-2-((5-bromo-7-chloro-1-((2-(trimethylsilyl)ethoxy)methyl)-1H-pyrrolo[3,2-b]pyridin-2-yl)methyl)-5-fluoro-3-oxoisoindoline-1-carboxylate

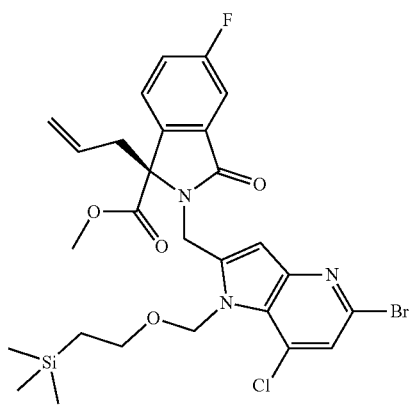 [SMILES: C=CC[C@@]1(C(=O)OC)c2ccc(F)cc2C(=O)N1Cc1cc2nc(Br)cc(Cl)c2n1COCC[Si](C)(C)C]

Sodium hydride (60% in mineral oil) (0.29 g, 7.26 mmol) was added to methyl (S)-1-allyl-5-fluoro-3-oxoisoindoline-1-carboxylate (1.73 g, 6.93 mmol) in DMF (20 mL) at 0° C. The reaction mixture was stirred at rt for 30 minutes. 5-Bromo-2-(bromomethyl)-7-chloro-1-((2-(trimethylsilyl)ethoxy)methyl)-1H-pyrrolo[3,2-b]pyridine (3.00 g, 6.60 mmol) was added and the reaction mixture was stirred at rt for 1 hour. The reaction mixture was quenched with saturated NH₄Cl (50 mL) and extracted with EtOAc (2×100 mL). The organic phase was dried over Na₂SO₄, filtered and the solvent was removed in vacuo. The crude product was purified by flash silica chromatography, elution gradient 0 to 50% EtOAc in petroleum ether (60-90° C.). Pure fractions were evaporated to dryness to afford the title compound (3.85 g, 94%) as a yellow solid.

$^1$H NMR (300 MHz, DMSO-d6) −0.09 (9H, s), 0.77-0.88 (2H, m), 3.08 (3H, s), 3.12-3.32 (2H, m), 3.52-3.65 (2H, m), 4.77 (1H, d), 4.83-5.12 (3H, m), 5.25 (1H, d), 5.67 (1H, d), 5.92 (1H, d), 6.85 (1H, s), 7.41-7.70 (4H, m); m/z MH⁺ 622

Step 2: Methyl (S)-1-allyl-2-((5-((tert-butoxycarbonyl)amino)-7-chloro-1-((2-(trimethylsilyl)ethoxy)methyl)-1H-pyrrolo[3,2-b]pyridin-2-yl)methyl)-5-fluoro-3-oxoisoindoline-1-carboxylate

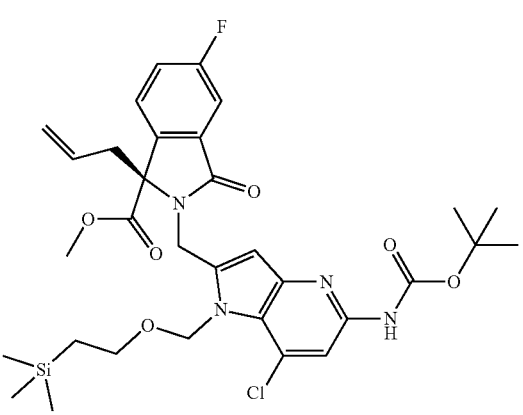

Methyl (S)-1-allyl-2-((5-bromo-7-chloro-1-((2-(trimethylsilyl)ethoxy)methyl)-1H-pyrrolo[3,2-b]pyridin-2-yl)methyl)-5-fluoro-3-oxoisoindoline-1-carboxylate (3.80 g, 6.10 mmol) was added to tris(dibenzylideneacetone)dipalladium(0) (1.12 g, 1.22 mmol), tert-butyl carbamate (0.71 g, 6.10 mmol), 9,9-Dimethyl-4,5-bis(diphenylphosphino)xanthene (0.71 g, 1.22 mmol) and caesium carbonate (3.97 g, 12.20 mmol) in dioxane (20 mL) under nitrogen at rt. The reaction mixture was stirred at 80° C. for 4 hours, cooled and the solvent was removed in vacuo. The crude product was purified by flash silica chromatography, elution gradient 0 to 30% EtOAc in petroleum ether (60-90° C.). Pure fractions were evaporated to dryness to afford the title compound (3.00 g, 75%) as a yellow solid.

$^1$H NMR (300 MHz, DMSO-d6) −0.06 (9H, d), 0.84-0.89 (2H, m), 1.48 (9H, s), 3.01-3.10 (3H, m), 3.13-3.33 (2H, m), 3.54-3.71 (2H, m), 4.67-4.81 (1H, m), 4.84-5.15 (3H, m), 5.28 (1H, d), 5.63 (1H, d), 5.90 (1H, d), 6.69 (1H, s), 7.47-7.59 (1H, m), 7.59-7.71 (2H, m), 7.76 (1H, s), 9.84 (1H, s); m/z MH$^+$ 659

Step 3: Methyl (S)-2-((5-((tert-butoxycarbonyl)amino)-7-chloro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate

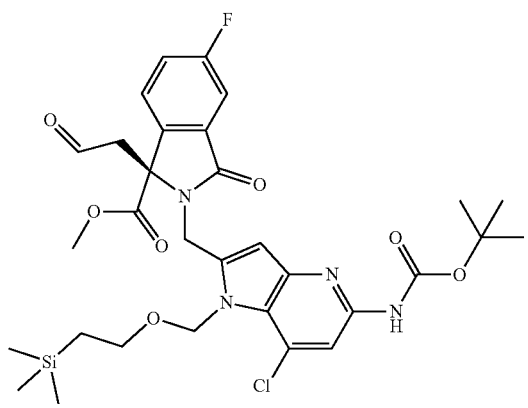 [SMILES: COC(=O)[C@]1(CC=O)c2ccc(F)cc2C(=O)N1Cc1cc2nc(NC(=O)OC(C)(C)C)cc(Cl)c2n1COCC[Si](C)(C)C]

Potassium dioxidodioxoosmium dihydrate (0.08 g, 0.20 mmol) were added to methyl (S)-1-allyl-2-((5-((tert-butoxycarbonyl)amino)-7-chloro-1-((2-(trimethylsilyl)ethoxy)methyl)-1H-pyrrolo[3,2-b]pyridin-2-yl)methyl)-5-fluoro-3-oxoisoindoline-1-carboxylate (2.70 g, 4.10 mmol), sodium periodate (3.50 g, 16.38 mmol) and 2,6-dimethylpyridine (0.88 g, 8.19 mmol) in dioxane (75 mL) and water (25 mL) at rt. The reaction mixture was stirred at rt for 16 hours. The reaction mixture was poured into water (150 mL) and extracted with EtOAc (2×200 mL). The organic phases were combined, washed with saturated brine, dried over MgSO$_4$ and the solvent was removed in vacuo. The crude product was purified by flash silica chromatography, elution gradient 0 to 60% EtOAc in petroleum ether (60-90° C.). Pure fractions were evaporated to dryness to afford the title compound (1.80 g, 66%) as a yellow foam.

$^1$H NMR (400 MHz, CDCl$_3$) −0.03 (9H, s), 0.72-0.92 (2H, m), 1.54 (9H, s), 3.27-3.41 (2H, m), 3.54-3.61 (5H, m), 4.96 (1H, d), 5.22-5.38 (1H, m), 5.71 (1H, d), 5.89 (1H, d), 6.38 (1H, s), 7.29-7.37 (2H, m), 7.48-7.55 (1H, m), 7.57-7.64 (1H, m), 7.95 (1H, s), 9.20 (1H, d); m/z MH$^+$ 661

Step 4: tert-Butyl (S)-(7-chloro-2-((5-fluoro-1'-((1-methylcyclopropyl)methyl)-2',3-dioxospiro[isoindoline-1,3'-pyrrolidin]-2-yl)methyl)-1-((2-(trimethylsilyl)ethoxy)methyl)-1H-pyrrolo[3,2-b]pyridin-5-yl)carbamate

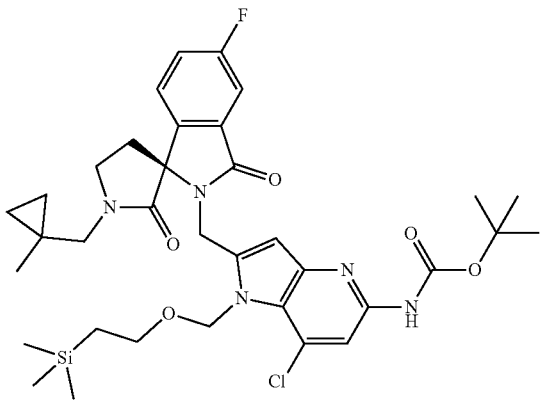 [SMILES: CC1(CN2CC[C@@]3(C2=O)c2ccc(F)cc2C(=O)N3Cc2cc3nc(NC(=O)OC(C)(C)C)cc(Cl)c3n2COCC[Si](C)(C)C)CC1]

Sodium acetate (112 mg, 1.36 mmol) was added to methyl (S)-2-((5-((tert-butoxycarbonyl)amino)-7-chloro-1-((2-(trimethylsilyl)ethoxy)methyl)-1H-pyrrolo[3,2-b]pyridin-2-yl)methyl)-5-fluoro-3-oxo-1-(2-oxoethyl)isoindoline-1-carboxylate (450 mg, 0.68 mmol) and (1-methylcyclopropyl)methanamine hydrochloride (99 mg, 0.82 mmol) in 1,2-dichloroethane (10 mL) at rt. After 1 hour sodium triacetoxyborohydride (288 mg, 1.36 mmol) was added and the reaction mixture was stirred at rt for 16 hours. The solvent was removed and the solvent was removed in vacuo. The crude product was purified by flash silica chromatography, elution gradient 0 to 100% EtOAc in petroleum ether (60-90° C.). Pure fractions were evaporated to dryness to afford the title compound (0.42 g, 88%) as a pale yellow solid.

$^1$H NMR (300 MHz, DMSO-d6) −0.10 (9H, s), 0.24-0.46 (4H, m), 0.60-0.82 (2H, m), 0.90 (3H, s), 1.47 (9H, s), 2.35-2.49 (2H, m), 2.76 (1H, d), 3.19 (1H, d), 3.42-3.63 (3H, m), 3.83 (1H, q), 4.62 (1H, d), 5.18 (1H, d), 5.61 (1H, d), 5.74-5.88 (1H, m), 6.48 (1H, s), 7.42-7.83 (4H, m), 9.77 (1H, s); m/z MH$^+$ 698

Step 5: (S)-5-Amino-2-((5-fluoro-1'-((1-methylcyclopropyl)methyl)-2',3-dioxospiro[isoindoline-1,3'-pyrrolidir]-2-yl)methyl)-1H-pyrrolo[3,2-b]pyridine-7-carbonitrile

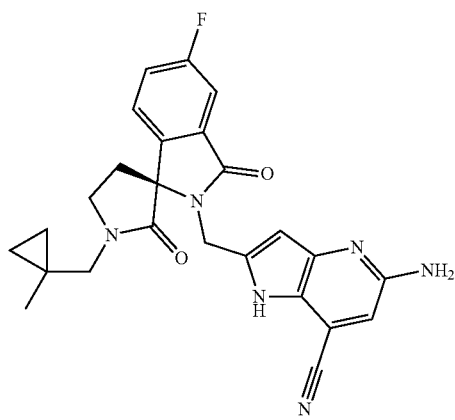 [SMILES: CC1(CN2CC[C@@]3(C2=O)c2ccc(F)cc2C(=O)N3Cc2cc3nc(N)cc(C#N)c3[nH]2)CC1]

Tris(dibenzylideneacetone)dipalladium(0) (108 mg, 0.12 mmol) was added to tert-butyl (S)-(7-chloro-2-((5-fluoro-1'-((1-methylcyclopropyl)methyl)-2',3-dioxospiro[isoindoline-1,3'-pyrrolidir]-2-yl)methyl)-1-((2-(trimethylsilyl)ethoxy)methyl)-1H-pyrrolo[3,2-b]pyridin-5-yl)carbamate (410 mg, 0.59 mmol), 1,1'-bis(diphenylphosphino)ferrocene (130 mg, 0.23 mmol), zinc cyanide (69 mg, 0.59 mmol) and zinc (8 mg, 0.12 mmol) in dioxane (0.5 mL) under nitrogen at rt. The reaction mixture was stirred at 100° C. for 4 hours, cooled, filtered through a Celite® pad and the solvent was removed in vacuo. The crude product was purified by flash silica chromatography, elution gradient 0 to 100% EtOAc in petroleum ether (60-90° C.). Pure fractions were evaporated to dryness to afford tert-butyl (S)-(7-cyano-2-((5-fluoro-1'-((1-methylcyclopropyl)methyl)-2',3-dioxospiro[isoindoline-1,3'-pyrrolidin]-2-yl)methyl)-1-((2-(trimethylsilyl)ethoxy)methyl)-1H-pyrrolo[3,2-b]pyridin-5-yl)carbamate as brown gum. 2,2,2-trifluoroacetic acid (10 mL, 129.80 mmol) was added and the reaction mixture was stirred at rt for 1 hour. The solvent was removed in vacuo and the crude product was purified by ion exchange chromatography, using an SCX column. The desired product was eluted from the column using 7M NH$_3$/MeOH and pure fractions were evaporated to dryness to afford crude product. The crude product was purified by preparative HPLC. Fractions containing the desired compound were evaporated to dryness to afford the title compound (85 mg, 32%) as a pale yellow solid.

$^1$H NMR (400 MHz, DMSO-d6) 0.25-0.55 (4H, m), 0.97 (3H, s), 2.37-2.50 (2H, m), 2.93 (1H, d), 3.36 (1H, d), 3.48-3.58 (1H, m), 3.79-3.90 (1H, m), 4.30 (1H, d), 5.03 (1H, d), 5.78 (2H, s), 6.13 (1H, s), 6.59 (1H, s), 7.39-7.79 (3H, m), 11.60 (1H, s); m/z MH$^+$ 459

Example 27: (S)-2-((5-Amino-6-chloro-1H-pyrrolo[3,2-b]pyridin-2-yl)methyl)-5-fluoro-1'-(2-(trifluoromethoxy)ethyl)spiro[isoindoline-1,3'-pyrrolidine]-2',3-dione Step 1: (S)-5-fluoro-1'-(2-(trifluoromethoxy)ethyl)spiro[isoindoline-1,3'-pyrrolidine]-2',3-dione

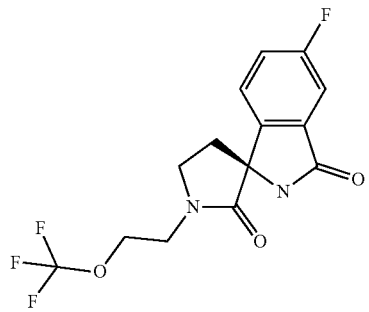 [SMILES: O=C1N[C@@]2(CCN(CCOC(F)(F)F)C2=O)c2ccc(F)cc21]

2-(Trifluoromethoxy)ethan-1-amine (2.92 g, 22.62 mmol) was added to methyl (S)-5-fluoro-2-(4-methoxybenzyl)-3-oxo-1-(2-oxoethyl)isoindoline-1-carboxylate (8.00 g, 21.54 mmol) in 1,2-dichloroethane (80 mL). After 1 hour sodium triacetoxyborohydride (10.96 g, 51.70 mmol) was added and the reaction mixture was stirred at rt for 16 hours. The solvent was removed in vacuo. The crude product was purified by flash silica chromatography, elution gradient 0 to 60% petroleum ether in EtOAc. Pure fractions were evaporated to dryness to afford rac-(R)-5-fluoro-2-(4-methoxybenzyl)-1'-(2-(trifluoromethoxy)ethyl)spiro[isoindoline-1,3'-pyrrolidine]-2',3-dione (9.50 g, 97%). The material was added to ammonium cerium(IV) nitrate (23.02 g, 42.00 mmol) in MeCN (70 mL) and water (35 mL) at rt. The reaction mixture was stirred at rt for 2 hours. The reaction mixture was diluted with water (70 mL) and extracted with EtOAc (3×200 mL). The organic phase was dried over Na$_2$SO$_4$ and the solvent was removed in vacuo. The crude product was purified by flash silica chromatography, elution gradient 0 to 60% EtOAc in petroleum ether (60-90° C.). and elution gradient 0 to 25% MeOH in DCM. The racemic crude product was purified by preparative chiral HPLC. Pure fractions were evaporated to dryness to afford the title compound (4.50 g, 65%) as a yellow solid.

$^1$H NMR (400 MHz, DMSO-d6) 2.36-2.50 (2H, m), 3.50-3.61 (1H, m), 3.58-3.68 (1H, m), 3.68-3.84 (2H, m), 4.21-4.34 (2H, m), 7.41-7.55 (3H, m), 9.10 (1H, s); m/z MH$^+$ 333

Step 2: ((S)-2-((5-chloro-1-tosyl-1H-pyrrolo[3,2-b]pyridin-2-yl)methyl)-5-fluoro-1'-(2-(trifluoromethoxy)ethyl)spiro[isoindoline-1,3'-pyrrolidine]-2',3-dione

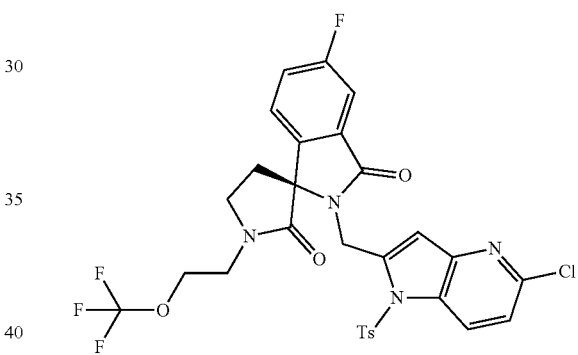

Sodium hydride (60% in mineral oil) (66 mg, 1.66 mmol) was added to (S)-5-fluoro-1'-(2-(trifluoromethoxy)ethyl)spiro[isoindoline-1,3'-pyrrolidine]-2',3-dione (460 mg, 1.39 mmol) in THF (15 mL) at 0° C. and the reaction mixture was stirred at rt for 1 hour. 2-(Bromomethyl)-5-chloro-1-tosyl-1H-pyrrolo[3,2-b]pyridine (720 mg, 1.80 mmol) was added and the reaction mixture was stirred at rt for 3 hours. The reaction mixture was quenched with saturated NH$_4$Cl, basified with saturated NaHCO$_3$ (25 mL) and extracted with EtOAc (3×25 mL). The organic phase was dried over Na$_2$SO$_4$ and the solvent was removed in vacuo. The crude product was purified by flash silica chromatography, elution gradient 0 to 40% EtOAc in DCM. Pure fractions were evaporated to dryness to afford the title compound (0.45 g, 50%) as a yellow solid.

$^1$H NMR (400 MHz, DMSO-d6) 2.38 (3H, s), 2.52-2.63 (2H, m), 3.49-3.61 (2H, m), 3.73-3.84 (1H, m), 3.84-3.95 (1H, m), 4.20-4.34 (2H, m), 4.68 (1H, d), 5.24 (1H, d), 6.73 (1H, s), 7.40 (1H, d), 7.43-7.50 (2H, m), 7.51-7.67 (3H, m), 7.86-7.93 (2H, m), 8.38-8.44 (1H, m); m/z MH$^+$ 651

Step 3: tert-Butyl (S)-(2-((5-fluoro-2',3-dioxo-1'-(2-(trifluoromethoxy)ethyl)spiro[isoindoline-1,3'-pyrrolidin]-2-yl)methyl)-1-tosyl-1H-pyrrolo[3,2-b]pyridin-5-yl)carbamate

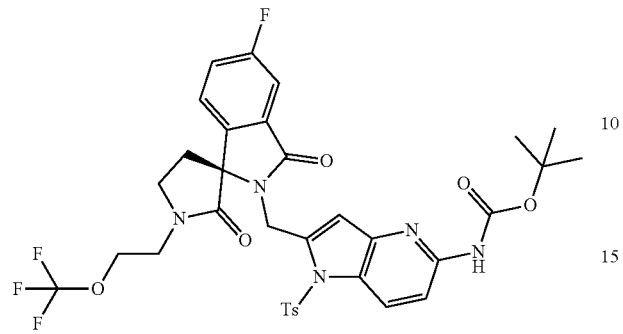

XPhos Pd G2 (53 mg, 0.07 mmol) was added to (S)-2-((5-chloro-1-tosyl-1H-pyrrolo[3,2-b]pyridin-2-yl)methyl)-5-fluoro-1'-(2-(trifluoromethoxy)ethyl)spiro[isoindoline-1,3'-pyrrolidine]-2',3-dione (443 mg, 0.68 mmol), dicyclohexyl(2',4',6'-triisopropyl-[1,1'-biphenyl]-2-yl)phosphane (32 mg, 0.07 mmol), caesium carbonate (443 mg, 1.36 mmol) and tert-butyl carbamate (239 mg, 2.04 mmol) in 1,4-dioxane (0.5 mL) under nitrogen at rt. The reaction mixture was stirred at 90° C. for 6 hours, cooled and the solvent was removed in vacuo. The crude product was purified by flash silica chromatography, elution gradient 0 to 30% EtOAc in DCM. Pure fractions were evaporated to dryness to afford the title compound (0.26 g, 51%) as a yellow solid.

$^1$H NMR (400 MHz, DMSO-d6) 1.46 (9H, s), 1.99 (1H, s), 2.36 (3H, s), 3.51-3.58 (2H, m), 3.74-3.90 (2H, m), 4.04 (1H, q), 4.24-4.30 (2H, m), 4.63 (1H, d), 5.23 (1H, d), 6.51 (1H, s), 7.43 (2H, d), 7.53-7.63 (3H, m), 7.78 (1H, d), 7.82-7.86 (2H, m), 8.30 (1H, d), 9.74 (1H, s); m/z MH$^+$ 732

Step 4: (S)-2-((5-Amino-1-tosyl-1H-pyrrolo[3,2-b]pyridin-2-yl)methyl)-5-fluoro-1'-(2-(trifluoromethoxy)ethyl)spiro[isoindoline-1,3'-pyrrolidine]-2',3-dione

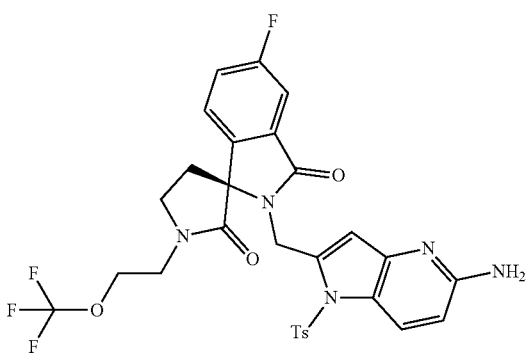 [SMILES: Cc1ccc(S(=O)(=O)n2c(CN3C(=O)c4cc(F)ccc4[C@]34CCN(CCOC(F)(F)F)C4=O)cc3nc(N)ccc32)cc1]

tert-Butyl (S)-(2-((5-fluoro-2',3-dioxo-1'-(2-(trifluoromethoxy)ethyl)spiro[isoindoline-1,3'-pyrrolidin]-2-yl)methyl)-1-tosyl-1H-pyrrolo[3,2-b]pyridin-5-yl)carbamate (246 mg, 0.34 mmol) was dissolved in DCM (5 mL) and 2,2,2-trifluoroacetic acid (5 mL). The reaction mixture was stirred at rt for 2 hours and the solvent was removed in vacuo. The crude product was purified by ion exchange chromatography, using an SCX column. The desired product was eluted from the column using 7M NH$_3$/MeOH and fractions were evaporated to dryness. The crude product was purified by flash C18-flash chromatography, elution gradient 0 to 100% MeOH in water (0.1% NH$_4$HCO$_3$). Pure fractions were evaporated to dryness to afford the title compound (0.13 g, 62%) as a white solid. m/z MH$^+$ 632.

Step 5: (S)-2-((5-Amino-6-chloro-1-tosyl-1H-pyrrolo[3,2-b]pyridin-2-yl)methyl)-5-fluoro-1'-(2-(trifluoromethoxy)ethyl)spiro[isoindoline-1,3'-pyrrolidine]-2',3-dione

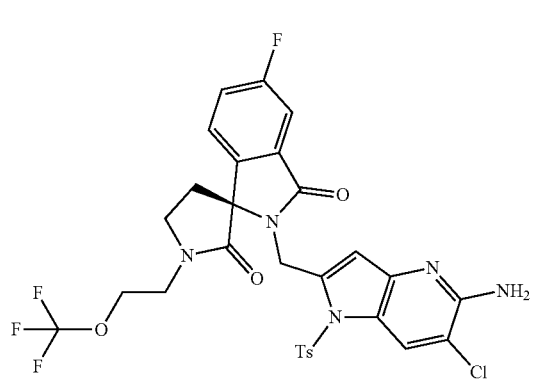 [SMILES: Cc1ccc(S(=O)(=O)n2c(CN3C(=O)c4cc(F)ccc4[C@]34CCN(CCOC(F)(F)F)C4=O)cc3nc(N)c(Cl)cc32)cc1]

N-Chlorosuccinimide (19 mg, 0.14 mmol) was added to (S)-2-((5-amino-1-tosyl-1H-pyrrolo[3,2-b] pyridin-2-yl)methyl)-5-fluoro-1'-(2-(trifluoromethoxy)ethyl)spiro[isoindoline-1,3'-pyrrolidine]-2',3-dione (93 mg, 0.14 mmol) in DMF (5 mL) at rt. The reaction mixture was stirred at rt for 12 hours. The solvent was removed in vacuo. The residue was diluted with EtOAc (50 mL) and washed sequentially with water (2×50 mL) and saturated brine (20 mL). The organic phase was dried over Na$_2$SO$_4$, filtered and the solvent was removed in vacuo. The crude product was purified by flash silica chromatography, elution gradient 0 to 30% DCM in EtOAc. Pure fractions were evaporated to dryness to afford the title compound (60 mg, 64%) as a white solid.

$^1$H NMR (400 MHz, DMSO-d6) 1.23 (2H, s), 2.37 (3H, s), 3.50-3.57 (2H, m), 3.75-3.91 (2H, m), 4.25 (2H, dd), 4.53 (1H, d), 5.17 (1H, d), 6.24 (2H, s), 6.34 (1H, s), 7.44 (2H, d), 7.57-7.60 (2H, m), 7.80 (2H, d), 8.07 (1H, d) (1H under DMSO signal); m/z MH$^+$ 666

Step 6; (S)-2-((5-Amino-6-chloro-1H-pyrrolo[3,2-b]pyridin-2-yl)methyl)-5-fluoro-1'-(2-(trifluoromethoxy)ethyl)spiro[isoindoline-1,3'-pyrrolidine]-2',3-dione

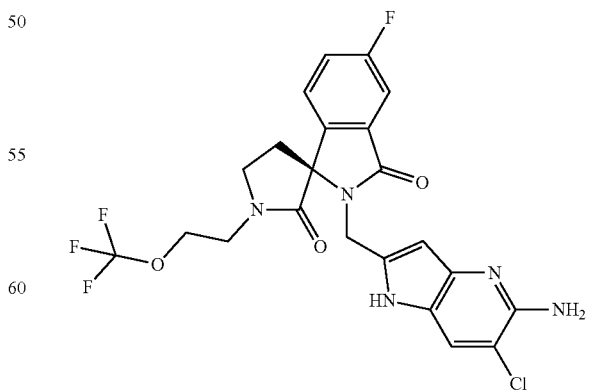

Tetrabutylammonium fluoride trihydrate (78 mg, 0.25 mmol) was added to (S)-2-((5-amino-6-chloro-1-tosyl-1H- pyrrolo[3,2-b]pyridin-2-yl)methyl)-5-fluoro-1'-(2-(trifluoromethoxy)ethyl)spiro[isoindoline-1,3'-pyrrolidine]-2',3-dione (55 mg, 0.08 mmol) in MeCN (1 mL) at rt. The reaction mixture was stirred at 80° C. for 2 hours, cooled and the solvent was removed in vacuo. The crude product was purified by flash C18-flash chromatography, elution gradient 0 to 100% MeCN in water (0.1% NH$_4$HCO$_3$). Fractions were evaporated to dryness and the impure product was purified by preparative HPLC. Fractions containing the desired compound were evaporated to dryness to afford the title compound (5 mg, 12%) as a white solid.

$^1$H NMR (300 MHz, DMSO-d6) 2.40 (2H, d), 3.47-3.74 (4H, m), 3.76-3.88 (1H, m), 4.20-4.35 (3H, m), 5.01 (1H, d), 5.73 (1H, s), 6.10 (1H, s), 7.46-7.64 (4H, m), 10.84 (1H, s); m/z MH$^+$ 512

Example 28: (S)-2-((6-Amino-4-methyl-1H-pyrrolo[2,3-b]pyridin-2-yl)methyl)-5-fluoro-1'-(2,4,5-trifluorobenzyl)spiro[isoindoline-1,3'-pyrrolidine]-2',3-dione Step 1; (S)-5-Fluoro-1'-(2,4,5-trifluorobenzyl)spiro[isoindoline-1,3'-pyrrolidine]-2',3-dione

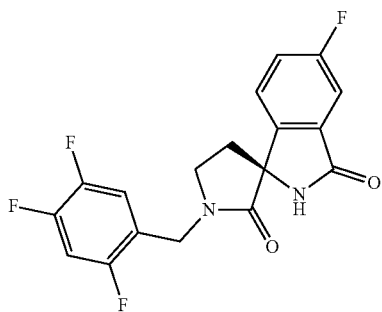 [SMILES: O=C1N[C@@]2(CCN(Cc3cc(F)c(F)cc3F)C2=O)c2ccc(F)cc21]

Methyl (S)-5-fluoro-2-(4-methoxybenzyl)-3-oxo-1-(2-oxoethyl)isoindoline-1-carboxylate (1.50 g, 4.04 mmol) and 2,4,5-trifluorobenzylamine (0.78 g, 4.85 mmol) were placed in a flask with 1,2-dichloroethane (30 mL). Acetic acid (0.46 mL, 8.08 mmol) was added followed by sodium triacetoxyborohydride (1.71 g, 8.08 mmol). The reaction mixture was stirred at 40° C. for 2 hours, cooled, diluted with DCM (100 mL) and washed with saturated NaHCO$_3$ (100 mL). The organic phase was passed through a phase separating filter paper and the solvent was removed in vacuo to afford crude (S)-5-fluoro-2-(4-methoxybenzyl)-1'-(2,4,5-trifluorobenzyl)spiro[isoindoline-1,3'-pyrrolidine]-2',3-dione as a white foam (1.96 g, 4.04 mmol). Crude (S)-5-fluoro-2-(4-methoxybenzyl)-1'-(2,4,5-trifluorobenzyl)spiro[isoindoline-1,3'-pyrrolidine]-2',3-dione (1.96 g, 4.04 mmol) was placed in a flask with MeCN (30 mL) and water (15 mL). Ammonium cerium(IV) nitrate (6.64 g, 12.12 mmol) was added and the reaction mixture was stirred at rt for 30 minutes. The reaction mixture was partitioned between DCM (100 mL) and water (100 mL). The organic phase was passed through a phase separating filter paper and the solvent was removed in vacuo. The crude product was purified by flash silica chromatography, elution gradient 0 to 100% EtOAc in heptane. Pure fractions were evaporated to dryness to the title compound (1.06 g, 72%) as an off-white crystalline solid.

$^1$H NMR (400 MHz, DMSO-d6, 30° C.) 2.41 (1H, ddd), 2.52-2.56 (1H, m), 3.53 (1H, td), 3.66 (1H, dt), 4.52 (2H, s), 7.45 (3H, qt), 7.50-7.57 (1H, m), 7.61 (1H, ddd), 9.11 (1H, s); m/z MH$^+$ 365.

Step 2; (S)-2-((6-Chloro-4-methyl-1-((2-(trimethylsilyl)ethoxy)methyl)-1H-pyrrolo[2,3-b]pyridin-2-yl)methyl)-5-fluoro-1'-(2,4,5-trifluorobenzyl)spiro[isoindoline-1,3'-pyrrolidine]-2',3-dione

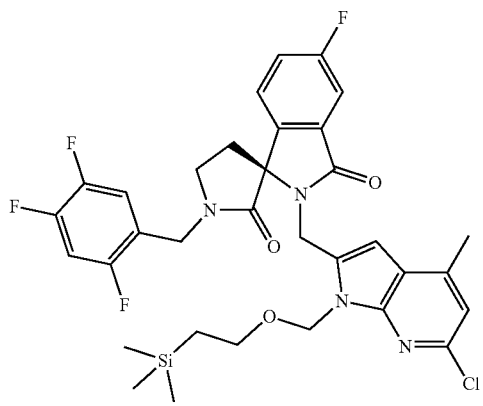 [SMILES: Cc1cc(Cl)nc2c1cc(CN1C(=O)c3cc(F)ccc3[C@]13CCN(Cc1cc(F)c(F)cc1F)C3=O)n2COCC[Si](C)(C)C]

(S)-5-Fluoro-1'-(2,4,5-trifluorobenzyl)spiro[isoindoline-1,3'-pyrrolidine]-2',3-dione (200 mg, 0.55 mmol) was placed in a flask with dry DMF (2 mL). Caesium carbonate (537 mg, 1.65 mmol) was added followed by 6-chloro-2-(chloromethyl)-4-methyl-1-((2-(trimethylsilyl)ethoxy)methyl)-1H-pyrrolo[2,3-b]pyridine (209 mg, 0.60 mmol), dissolved in dry DMF (2 mL), and the reaction mixture was stirred at 110° C. for 1 hour. The reaction mixture was quenched with saturated NH$_4$Cl (50 mL) and extracted into EtOAc (50 mL). The organic phase was washed with water (2×50 mL), brine (50 mL), passed through a phase separator and the solvent was removed in vacuo. The crude product was purified by flash silica chromatography, elution gradient 0 to 100% EtOAc in heptane. Pure fractions were evaporated to dryness to afford the title compound (320 mg, 87%) as a pale yellow oil.

$^1$H NMR (400 MHz, DMSO-d6, 30° C.) −0.12 (9H, s), 0.71 (2H, dddd), 2.43 (5H, s), 3.35 (1H, ddd), 3.43 (2H, dtd), 3.62-3.73 (1H, m), 4.36 (2H, s), 4.57 (1H, d), 5.16 (1H, d), 5.50 (1H, d), 5.62 (1H, d), 6.45 (1H, s), 7.02 (1H, d), 7.37-7.45 (1H, m), 7.49-7.63 (4H, m); m/z MH$^+$ 673

Step 3; tert-Butyl (S)-(2-((5-fluoro-2',3-dioxo-1'-(2,4,5-trifluorobenzyl)spiro[isoindoline-1,3'-pyrrolidin]-2-yl)methyl)-4-methyl-1-((2-(trimethylsilyl)ethoxy)methyl)-1H-pyrrolo[2,3-b]pyridin-6-yl)carbamate

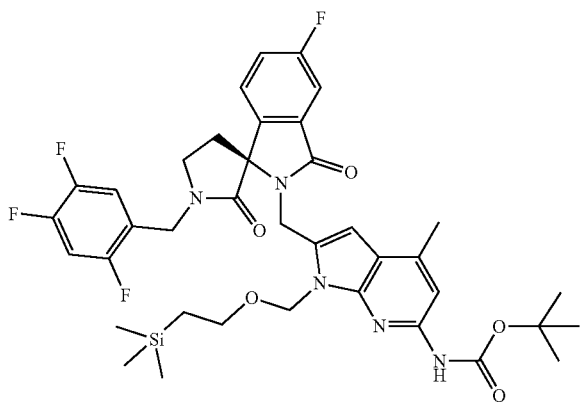 [SMILES: Cc1cc(NC(=O)OC(C)(C)C)nc2c1cc(CN1C(=O)c3cc(F)ccc3[C@]13CCN(Cc1cc(F)c(F)cc1F)C3=O)n2COCC[Si](C)(C)C]

(S)-2-((6-Chloro-4-methyl-1-((2-(trimethylsilyl)ethoxy)methyl)-1H-pyrrolo[2,3-b]pyridin-2-yl)methyl)-5-fluoro-1'-(2,4,5-trifluorobenzyl)spiro[isoindoline-1,3'-pyrrolidine]-2',3-dione (350 mg, 0.52 mmol), tert-butyl carbamate (305 mg, 2.60 mmol) and caesium carbonate (508 mg, 1.56 mmol) were placed in a flask with 1,4-dioxane (2 mL). The reaction was degassed for 15 minutes, XPhos Pd G2 (40.9 mg, 0.05 mmol) was added and the reaction mixture was heated at 100° C. for 1 hour. The reaction mixture was allowed to cool, diluted with EtOAc (20 mL), washed with water (20 mL) and brine (20 mL). The organic phase was passed through a phase separating filter and the solvent was removed in vacuo. The crude product was purified by flash silica chromatography, elution gradient 0 to 100% EtOAc in heptane. Pure fractions were evaporated to dryness to afford the title compound (330 mg, 84%) as a pale yellow oil.

¹H NMR (400 MHz, DMSO-d6, 30° C.) −0.13 (9H, s), 0.54-0.65 (1H, m), 0.71 (1H, dt), 1.27-1.31 (1H, m), 1.46 (9H, s), 2.37 (4H, d), 3.32 (1H, d), 3.37-3.43 (2H, m), 3.60-3.71 (1H, m), 4.29-4.41 (2H, m), 4.50 (1H, d), 5.17 (1H, d), 5.43 (1H, d), 5.57 (1H, d), 6.28 (1H, s), 7.36-7.40 (1H, m), 7.41-7.47 (1H, m), 7.48-7.67 (4H, m), 9.36 (1H, s); m/z MH⁺ 754

Step 4: (S)-2-((6-Amino-4-methyl-1H-pyrrolo[2,3-b]pyridin-2-yl)methyl)-5-fluoro-1'-(2,4,5-trifluorobenzyl)spiro[isoindoline-1,3'-pyrrolidine]-2',3-dione

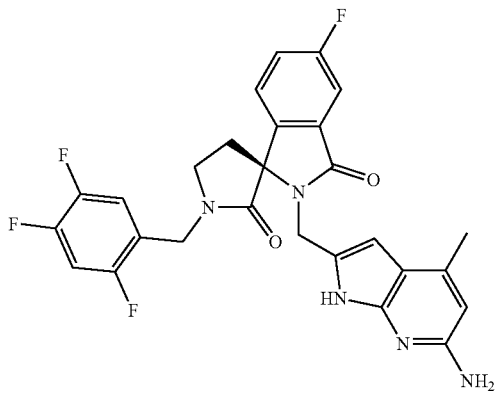 [SMILES: Cc1cc(N)nc2[nH]c(CN3C(=O)c4cc(F)ccc4[C@]34CCN(Cc3cc(F)c(F)cc3F)C4=O)cc12]

tert-Butyl (S)-(2-((5-fluoro-2',3-dioxo-1'-(2,4,5-trifluorobenzyl)spiro[isoindoline-1,3'-pyrrolidin]-2-yl)methyl)-4-methyl-1-((2-(trimethylsilyl)ethoxy)methyl)-1H-pyrrolo[2,3-b]pyridin-6-yl)carbamate (330 mg, 0.44 mmol) was placed in a flask with 2,2,2-trifluoroacetic acid (1997 mg, 17.51 mmol). The reaction mixture was stirred at rt for 1 hour. The 2,2,2-trifluoroacetic acid was removed in vacuo and the residue was dissolved in MeCN (4 mL). Ammonium hydroxide (28-30% in water) (2045 µl, 52.53 mmol) was added and the reaction mixture was stirred at 40° C. for 4 hours and then left at rt overnight. The crude product was purified by preparative HPLC. Fractions containing the desired compound were evaporated to dryness to afford the title compound (14 mg, 61%) as a cream solid.

¹H NMR (400 MHz, DMSO-d6, 30° C.) 2.22 (3H, d), 2.35-2.42 (2H, m), 3.31-3.38 (1H, m), 3.59-3.69 (1H, m), 4.14 (1H, d), 4.51 (2H, q), 4.97-5.09 (1H, m), 5.41 (2H, s), 5.97 (1H, d), 6.04 (1H, d), 7.45-7.53 (2H, m), 7.56 (2H, dt), 7.64 (1H, ddd), 10.66 (1H, d); m/z MH⁺ 524

Example 29: (1S,5'S)-2-((5-Amino-6-fluoro-1H-pyrrolo[3,2-b]pyridin-2-yl)methyl)-5-fluoro-1',5'-20 dimethylspiro[isoindoline-1,3'-pyrrolidine]-2',3-dione Step 1; rac-Methyl 5-fluoro-2-(4-methoxybenzyl)-1-(2-methylallyl)-3-oxoisoindoline-1-carboxylate

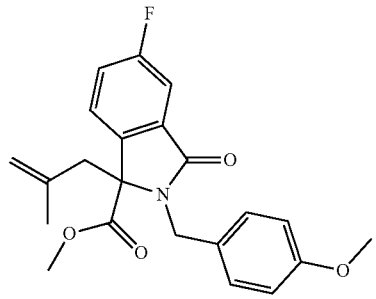 [SMILES: C=C(C)CC1(C(=O)OC)c2ccc(F)cc2C(=O)N1Cc1ccc(OC)cc1]

3-Bromo-2-methylprop-1-ene (350 µl, 3.45 mmol) was added to a stirred mixture of rac-methyl 5-fluoro-2-(4-methoxybenzyl)-3-oxoisoindoline-1-carboxylate (508 mg, 1.54 mmol), potassium carbonate (682 mg, 4.94 mmol) and the reaction mixture was stirred at 70° C. for 90 minutes and then at rt for 36 hours. The reaction mixture was quenched with saturated NH₄Cl (10 mL) and water (10 mL) then extracted with DCM (3×15 mL). The organic phase was passed through a phase separating cartridge and the solvent was removed in vacuo. The crude product was purified by flash silica chromatography, elution gradient 0 to 60% EtOAc in heptane. Pure fractions were evaporated to dryness to afford the title compound (0.53 g, 89%) as a waxy solid.

¹H NMR (400 MHz, CDCl₃, 30° C.) 1.17-1.23 (3H, m), 3.07 (3H, s), 3.09 (1H, d), 3.17 (1H, d), 3.77 (3H, s), 4.26 (1H, d), 4.45-4.53 (1H, m), 4.67 (1H, p), 5.13 (1H, d), 6.80-6.85 (2H, m), 7.22 (1H, td), 7.28-7.35 (3H, m), 7.54 (1H, dd); m/z MH⁺ 384

Step 2; rac-methyl 5-Fluoro-2-(4-methoxybenzyl)-3-oxo-1-(2-oxopropyl)isoindoline-1-carboxylate

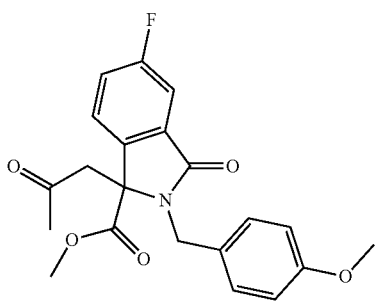 [SMILES: COC(=O)C1(CC(C)=O)c2ccc(F)cc2C(=O)N1Cc1ccc(OC)cc1]

A solution of rac-methyl 5-fluoro-2-(4-methoxybenzyl)-1-(2-methylallyl)-3-oxoisoindoline-1-carboxylate (515 mg, 1.34 mmol) in DCM (5 mL) was added to a solution of sodium periodate (1149 mg, 5.37 mmol) in water (5 mL). Ruthenium(III) chloride hydrate (7 mg, 0.03 mmol) was added and the mixture was stirred at rt for 18 hours. The reaction mixture was carefully quenched with a solution of sodium metabisulfite (10% aqueous, 15 mL) and extracted into DCM (10 mL). The organic phase was passed through a phase separating cartridge and the solvent was removed in vacuo. The crude product was purified by flash silica chromatography, elution gradient 0 to 60% EtOAc in heptane. Pure fractions were evaporated to dryness to afford the title compound (0.38 g, 74%) as a solid.

¹H NMR (400 MHz, CDCl₃, 30° C.) 1.52 (3H, s), 2.82 (1H, d), 3.37 (1H, d), 3.68 (3H, s), 3.76 (3H, s), 4.37 (1H, d), 5.27 (1H, d), 6.73-6.85 (2H, m), 7.11 (2H, d), 7.25 (1H, td), 7.52 (1H, dd), 7.57 (1H, dd); m/z MH⁺ 386

Step 3; rel-(1S,5'S)-5-Fluoro-2-(4-methoxybenzyl)-1',5'-dimethylspiro[isoindoline-1,3'-pyrrolidine]-2',3-dione

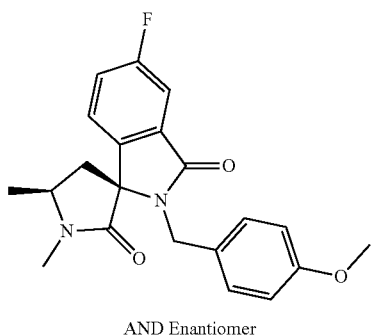

AND Enantiomer

Sodium triacetoxyborohydride (458 mg, 2.16 mmol) was added to a stirred solution of methyl 5-fluoro-2-(4-methoxybenzyl)-3-oxo-1-(2-oxopropyl)isoindoline-1-carboxylate (380 mg, 0.99 mmol), sodium acetate (404 mg, 4.93 mmol) and methanamine hydrochloride (333 mg, 4.93 mmol) in a microwave tube. The microwave tube was sealed and the reaction mixture was heated to 70° C. for 13 hours in a microwave reactor and cooled to rt. The reaction mixture was quenched with saturated NaHCO₃ (5 mL) and extracted with DCM (3×10 mL). The organic phase was passed through a phase separating cartridge and the solvent was removed in vacuo. The crude product was purified by preparative HPLC to afford rel-(1S,5'S)-5-fluoro-2-(4-methoxybenzyl)-1',5'-dimethylspiro[isoindoline-1,3'-pyrrolidine]-2',3-dione (32 mg, 9%) as a white solid, rel-(1R,5'S)-5-fluoro-2-(4-methoxybenzyl)-1',5'-dimethylspiro[isoindoline-1,3'-pyrrolidine]-2',3-dione (43 mg, 12%) as a white solid.

(Note: relative stereochemical assignments for these compounds was determined by 2D NMR experiments)

rel-(1S,5'S)-5-Fluoro-2-(4-methoxybenzyl)-1',5'-dimethylspiro[isoindoline-1,3'-pyrrolidine]-2',3-dione

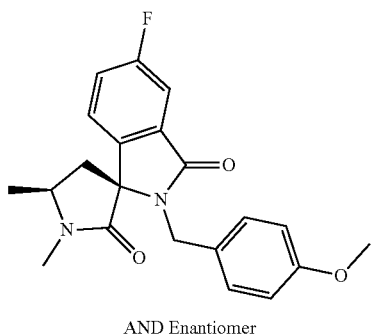

AND Enantiomer

¹H NMR (400 MHz, CDCl₃, 30° C.) 1.25 (3H, d), 1.93 (1H, dd), 2.28 (1H, dd), 2.96 (3H, s), 3.79 (3H, s), 3.80-3.89 (1H, m), 3.98 (1H, d), 5.30 (1H, d), 6.81-6.87 (2H, m), 7.13-7.25 (4H, m), 7.56 (1H, ddd); m/z MH⁺ 369.

rel-(1R,5'S)-5-Fluoro-2-(4-methoxybenzyl)-1',5'-dimethylspiro[isoindoline-1,3'-pyrrolidine]-2',3-dione

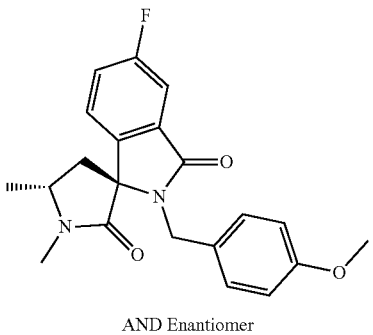

AND Enantiomer

¹H NMR (400 MHz, CDCl₃, 30° C.) 1.33 (3H, d), 2.01 (1H, dd), 2.48 (1H, dd), 2.73 (3H, s), 3.45-3.55 (1H, m), 3.79 (3H, s), 4.37 (1H, d), 4.84 (1H, d), 6.81-6.86 (2H, m), 7.18-7.27 (4H, m), 7.56 (1H, ddd); m/z MH⁺ 369.

Step 4; rel-(1S,5'S)-5-Fluoro-1',5'-dimethylspiro[isoindoline-1,3'-pyrrolidine]-2',3-dione

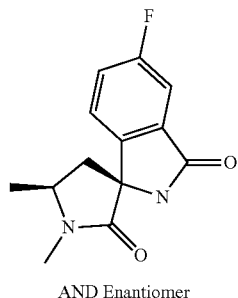 [SMILES: C[C@H]1C[C@@]2(NC(=O)c3cc(F)ccc32)C(=O)N1C]

AND Enantiomer

Ammonium cerium(IV) nitrate (208 mg, 0.38 mmol) was added to a stirred solution of rel-(1S,5'S)-5-fluoro-2-(4-methoxybenzyl)-1',5'-dimethylspiro[isoindoline-1,3'-pyrrolidine]-2',3-dione (28 mg, 0.08 mmol) in MeCN (2 mL) and water (1 mL). The reaction mixture was stirred for 30 minutes and then extracted into DCM (3×10 mL). The organic phase was passed through a phase separating cartridge and the solvent was removed in vacuo. The crude product was purified by flash silica chromatography, elution gradient 0 to 100% EtOAc in heptane to afford the title compound (16 mg, 83%) as a gum.

¹H NMR (400 MHz, CDCl₃, 30° C.) 1.42 (3H, d), 2.11 (1H, dd), 2.70 (1H, dd), 2.96 (3H, s), 3.93 (1H, h), 6.92 (1H, s), 7.21-7.25 (2H, m), 7.47-7.53 (1H, m); m/z MH⁺ 249.

JACS ¹H NMR (400 MHz, CDCl₃, 30° C.) 1.42 (d, J=6.2 Hz, 3H), 2.11 (dd, J=13.5, 7.7 Hz, 1H), 2.70 (dd, J=13.5, 6.7 Hz, 1H), 2.96 (s, 3H), 3.93 (h, J=6.3 Hz, 1H), 6.92 (s, 1H), 7.21-7.25 (m, 2H), 7.47-7.53 (m, 1H).

Step 5; rel-(1S,5'S)-2-((5-Chloro-6-fluoro-1-((2-(trimethylsilyl)ethoxy)methyl)-1H-pyrrolo[3,2-b]pyridin-2-yl)methyl)-5-fluoro-1',5'-dimethylspiro[isoindoline-1,3'-pyrrolidine]-2',3-dione

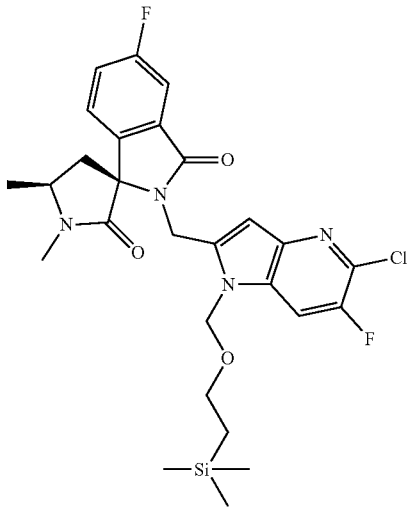

AND Enantiomer

A mixture of rel-(1S,5'S)-5-fluoro-1',5'-dimethylspiro[isoindoline-1,3'-pyrrolidine]-2',3-dione (15.7 mg, 0.06 mmol), 5-chloro-2-(chloromethyl)-6-fluoro-1-((2-(trimethylsilyl)ethoxy)methyl)-1H-pyrrolo[3,2-b]pyridine (38 mg, 0.11 mmol), caesium carbonate (72 mg, 0.22 mmol) and DMA (1 mL) was stirred at 85° C. for 3 hours and then cooled to rt. The reaction mixture was filtered and the filtrate was purified by preparative HPLC to afford the title compound (27 mg, 75%) as a gum.

$^1$H NMR (400 Hz, CDCl$_3$, 30° C.) −0.08 (9H, s), 0.74 (1H, ddd), 0.84 (1H, ddd), 1.28 (3H, d), 1.99-2.06 (1H, m), 2.33 (1H, dd), 2.75 (3H, s), 3.46-3.58 (2H, m), 3.85 (1H, dt), 4.95 (1H, d), 5.11 (1H, d), 5.46 (1H, d), 5.52 (1H, d), 6.52 (1H, s), 7.17 (1H, dd), 7.23 (1H, td), 7.54-7.60 (2H, m); m/z MH$^+$ 561.

Step 6; (1S,5'S)-2-((5-Amino-6-fluoro-1H-pyrrolo[3,2-b]pyridin-2-yl)methyl)-5-fluoro-1',5'-dimethylspiro[isoindoline-1,3'-pyrrolidine]-2',3-dione

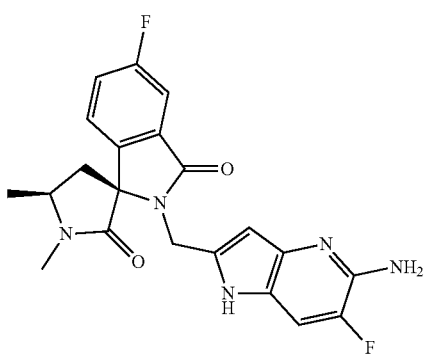 [SMILES: C[C@H]1C[C@@]2(C(=O)N1C)c1ccc(F)cc1C(=O)N2Cc1cc2nc(N)c(F)cc2[nH]1]

Tris(dibenzylideneacetone)dipalladium(0) (6 mg, 6.68 µmol) was added to a degassed solution of rel-(1S,5'S)-2-((5-chloro-6-fluoro-1-((2-(trimethylsilyl)ethoxy)methyl)-1H-pyrrolo[3,2-b]pyridin-2-yl)methyl)-5-fluoro-1',5'-dimethylspiro[isoindoline-1,3'-pyrrolidine]-2',3-dione (25 mg, 0.04 mmol), diphenylmethanimine (16 mg, 0.09 mmol), tBuXPhos (6 mg, 0.01 mmol) and sodium 2-methylpropan-2-olate (17 mg, 0.18 mmol) in toluene (3 mL) in a microwave tube. The reaction mixture heated to 80° C. for 1 hour in a microwave reactor and then stirred at 70° C. in a heating block for 17 hours. The reaction mixture was concentrated in vacuo. 2,2,2-trifluoroacetic acid (0.5 mL) and water (0.05 mL) were added and the reaction mixture was stirred at rt for 2 hours and concentrated in vacuo. The residue was re-dissolved in MeCN (1 mL) and 28-30% ammonia in water was added (1 mL). The reaction mixture was stirred for 3.5 hours, filtered and purified by preparative HPLC to afford the racemic product (8 mg, 41%). The enantiomers were separated using the SFC conditions: column: Phenomenex Lux iC5, 21.2×250 mm, 5 micron, mobile phase: 45% MeOH+0.1% NH$_3$/55% scCO$_2$, flow rate: 60 mL/min; BPR: 120 bar, column temperature: 40° C., UV max 220 nm (retention times: Isomer 1—6.8 minutes and Isomer 2—8.5 minutes) to afford Isomer 1 (1.6 mg, >99 pure, >99% ee) and Isomer 2 (2.5 mg, >99 pure, >99% ee).

Isomer 1—(1R,5'R)-2-((5-Amino-6-fluoro-1H-pyrrolo[3,2-b]pyridin-2-yl)methyl)-5-fluoro-1',5'-dimethylspiro[isoindoline-1,3'-pyrrolidine]-2',3-dione

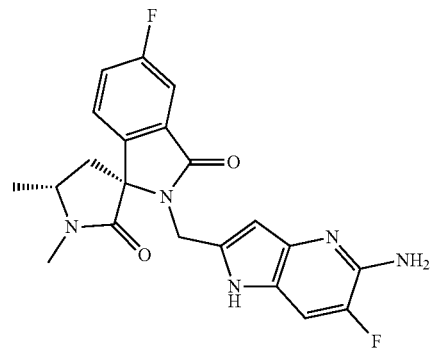 [SMILES: C[C@@H]1C[C@]2(C(=O)N1C)c1ccc(F)cc1C(=O)N2Cc1cc2nc(N)c(F)cc2[nH]1]

$^1$H NMR (400 MHz, CDCl$_3$, 30° C.) 1.45 (3H, d), 2.29 (1H, dd), 2.44 (1H, dd), 3.00 (3H, s), 3.94 (1H, dt), 4.29 (1H, d), 4.37 (2H, s), 5.04 (1H, d), 6.28 (1H, d), 7.17-7.25 (3H, m), 7.53 (1H, dd), 9.34 (1H, s); m/z MH$^+$ 411.

Isomer 2 (example 29)—(1S,5'S)-2-((5-Amino-6-fluoro-1H-pyrrolo[3,2-b]pyridin-2-yl)methyl)-5-fluoro-1',5'-dimethylspiro[isoindoline-1,3'-pyrrolidine]-2',3-dione

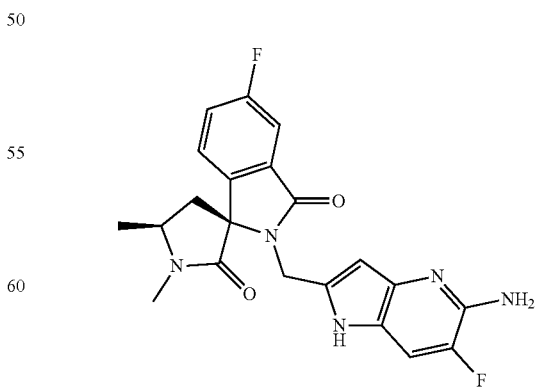

$^1$H NMR (400 MHz, CDCl$_3$, 30° C.) 1.45 (3H, d), 2.29 (1H, dd), 2.44 (1H, dd), 3.00 (3H, s), 3.94 (1H, dt), 4.29 (1H, d), 4.37 (2H, s), 5.04 (1H, d), 6.28 (1H, d), 7.17-7.25 (3H, m), 7.53 (1H, dd), 9.34 (1H, s); m/z MH⁺ 411.

(Presumed stereochemical assignment at the quaternary centre for this compound based on biological activity vs other enantiomer, together with Xray structural evidence that the S enantiomer is preferred and more active than the R enantiomer; relative stereochemical configuration of example 29 already confirmed from NMR analysis of the previous intermediate from step 3).

The invention claimed is:

1. A compound which is (S)-2-((5-Amino-6-fluoro-1H-pyrrolo[3,2-b]pyridin-2-yl)methyl)-1'-(but-2-yn-1-yl)-5-fluorospiro[isoindoline-1,3'-pyrrolidine]-2',3-dione:

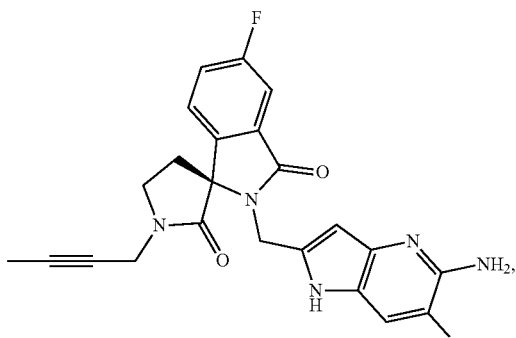

or a pharmaceutically acceptable salt thereof.

2. The compound according to claim 1, which is (S)-2-((5-Amino-6-fluoro-1H-pyrrolo[3,2-b]pyridin-2-yl)methyl)-1'-(but-2-yn-1-yl)-5-fluorospiro[isoindoline-1,3'-pyrrolidine]-2',3-dione:

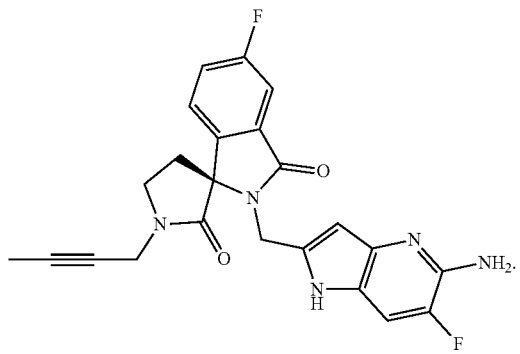 [SMILES: CC#CCN1CC[C@@]2(C1=O)c1ccc(F)cc1C(=O)N2Cc1cc2nc(N)c(F)cc2[nH]1]

3. The pharmaceutically acceptable salt according to claim 1, which is a pharmaceutically acceptable salt of (S)-2-((5-Amino-6-fluoro-1H-pyrrolo[3,2-b]pyridin-2-yl)methyl)-1'-(but-2-yn-1-yl)-5-fluorospiro[isoindoline-1,3'-pyrrolidine]-2',3-dione:

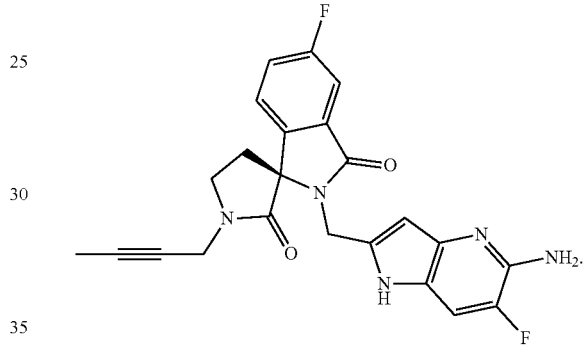

4. A pharmaceutical composition comprising the compound or pharmaceutically acceptable salt thereof according to claim 1.

* * * * *